US007001983B1

(12) United States Patent
Shai et al.

(10) Patent No.: US 7,001,983 B1
(45) Date of Patent: Feb. 21, 2006

(54) ANTIPATHOGENIC SYNTHETIC PEPTIDES AND COMPOSITIONS COMPRISING THEM

(75) Inventors: Yechiel Shai, Yahud (IL); Ziv Oren, Rishon Le-Zion (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/367,714

(22) PCT Filed: Feb. 19, 1998

(86) PCT No.: PCT/IL98/00081

§ 371 (c)(1),
(2), (4) Date: Jan. 14, 2000

(87) PCT Pub. No.: WO98/37090

PCT Pub. Date: Aug. 27, 1998

(30) Foreign Application Priority Data

Feb. 20, 1997 (IL) .................. PCT/IL97/00066

(51) Int. Cl.
*C07K 7/00* (2006.01)
(52) U.S. Cl. ............... 530/327; 530/328; 530/329; 514/14; 514/15; 514/16; 514/17
(58) Field of Classification Search .......... 514/11, 514/2, 14–17; 530/327, 328, 329, 317, 332
See application file for complete search history.

(56) References Cited

U.S. PATENT DOCUMENTS

| | | | |
|---|---|---|---|
| 4,874,850 A | * | 10/1989 | Paradies ................ 536/3 |
| 5,635,479 A | * | 6/1997 | Jacob et al. ............ 514/12 |
| 5,792,831 A | * | 8/1998 | Maloy .................. 530/326 |
| 5,889,148 A | * | 3/1999 | Lee et al. ............. 530/326 |

FOREIGN PATENT DOCUMENTS

WO    97-02286    *    1/1997

OTHER PUBLICATIONS

Lakey, Biochim Biophys Acta 859, 219-226, 1986.*
Wade et al., "Antibacterial peptides designed as analogs or hybrids of cecropins and melittin", *Int. J. Peptides Rcs.*, vol. 40, pp. 429-436, (1992).
Boman et al., "Antibacterial and antimalarial properties of peptides that are cecropin-melotzin hybrids", *FEBS Letters*, vol. 259, No. 1, pp. 103-106, (1989).
Rapaport et al., "pH- and Ionic Strength-Dependent Fusion of Phospholipid Vesicles Induced by Pardaxin Analogues or by Mixture of Charge-Reversed Peptides", *Biochemistry*, vol. 32, pp. 3291-3297, (1993).
Pouny et al, "Interaction of D-Amino Acid Incorporated Analogues of Pardaxin with Membranes", *Biochemistry*, vol. 31, pp. 9482-9489, (1992).

Shai et al., "Diastereomers of Cytolysins, a Novel Class of Potent Antibacterial Peptides", *The Journal of Biological Chemistry*, vol. 271, No. 13, pp. 7305-7308, (1996).
Agawa et al., "Interaction with Phospholipid Bilayers, Ion Chanel Formation, and Antimicrobial Activity of Basic Amphipathic α-Helical Model Peptides of Various Chai Lengths" *The Journal of Biological Chemistry*, vol. 266, No. 30, pp. 20218-20222, (1991).
Altenbach et al. . . . , "The Aggregation State of Spin-Labeled Melittin in Solution and Bound to Phospholipid Membranes: Evidence That Membrane-Bound Melittin Is Monomeric", *PROTEINS: Structure, Function and Genetics*, vol. 3, pp. 230-242, (1988).
Anderson et al., "Melittin Forms Crystal Which are Suitable for High Resolution X-ray Structural Analysis and Which Reveal a Molecular 2-Fold Axis of Symmetry", *The Journal of Biological Chemistry*, vol. 255, No. 6, pp. 2578-2582, (1990).
Anzai et al., "Formation of ion Channels in Planarlipids bilayers membranes by synthetic basic peptides", *Biochem. Biophys. Acta*, vol. 1064, pp. 256-266, (1991).
Barlett, "Phosphorus Assay in Column Chromatography", *J. Biol. Chem.*, vol. 234, pp. 466-468, (1959).
Batenburg et al., "Lipid specific penetration of melittin into phospholipid model membrane", *Biochem. biophy. Acta*, vol. 903, pp. 155-165, (1987).
Batenburg et al., "Melittin-Induced Changes of the Macroscopic Structure of Phosphatidylethanolamines", *Biochemistry*, vol. 27, pp. 2324-2331, (1988).
Batenburg et al., "Interaction of melittin with negative charged phospholipids: consequences for lipid organization", *FEBS Letters*, vol. 223, No. 1, pp. 148-154, (1987).
Bazzo et al., "The structure of melittin A $^1$H-NMR study in methanol", *Eur. J. Biochem.*, vol. 173, pp. 139-146, (1988).

(Continued)

*Primary Examiner*—David Lukton
(74) *Attorney, Agent, or Firm*—Browdy and Neimark

(57) ABSTRACT

Non-hemolytic cytolytic agents selected from peptides, complexes of bundled peptides, mixtures of peptides or random peptide copolymers have a selected cytolytic activity manifested in that they have a cytolytic activity on pathogenic cells, being cells which are non-naturally occurring with the body consisting of microbial pathogenic organisms and malignant cells; and are non-hemolytic, having no cytolytic effect on red blood cells. The peptides may be cyclic derivatives of natural peptides such as pardaxin and mellitin and fragments thereof in which L-amino acid residues are replaced by corresponding D-amino acid residues, or are diastereomers of linear peptides composed of varying ratios of at least positively charged amino acid and at least one hydrophobic amino acid, and in which at one of the amino acid residues is a D-amino acid. Pharmaceutical compositions comprising the non-hemolytic cytolytic agents can be used for the treatment of several diseases caused by pathogens including antibacterial, fungal, viral mycoplamsa and protozoan infections and for the treatment of cancer.

18 Claims, 14 Drawing Sheets

OTHER PUBLICATIONS

Benkrane et al., "Antigenicity and Immunogenicity of Modified Synthetic Peptides Containing D-Amino Acid Rosidues", *The Journal Biological Chemistry*, vol. 268, No. 35, pp. 26279-26285, (1993).

Beschiaschvili et al., "Melittin Binding to Mixed Phosphatidylglycerol/Phosphatidylcholine Membranes", *Biochemistry*, vol. 29, pp. 52-58, (1990).

Bessalle et al., "All-D-magainin: chirality, antimicrobial activity and proteolytic resistance", *FEBS Letters*, vol. 274, Nos. 1 and 2, pp. 151-155, (1990).

Bolen et al., "Quenching of Tryptophan Fluorescence by Brominated Phospholipid", *Biochemistry*, vol. 29, pp. 9638-9643, (1990).

Boman, "Peptide Antibiotics and Their Role in Innate Immunity", *Annu. Rev. Immunol*, vol. 13, pp. 61-92, (1995).

Chen et al., "Synthetic magainin analogues with improved antimicrobial activity", *FEBS Letters*, vol. 236, No. 2, pp. 462-466, (1988).

Cornut et al., "Application to the de novo design of ideally amphipathic Leu, Lys peptides with hemolytic activity higher than that of melittin", *FEBS Letters*, vol. 349, pp. 29-33, (1994).

Dempsey, "The actions of melittin on membranes", *Biochem. Biol. Acta.*, vol. 1031, pp. 143-161, (1990).

Dhople et al., "-Toxin, Unlike Melittin, has only Hemolytic Activity and no Antimicrobial Activity, Rationalization of this Specific Biological Activity", *Bioscience Reports*, vol. 13, No. 4, (1993).

Eisenberg et al., "Analysis of Membrane and surface Protein Sequences with the Hydrophobic Moment Plot", *J. Mol. Biol.*, vol. 179, pp. 125-142, (1984).

Fisher et al., "Calmodulin interacts with amphiphilic peptides composed of all D-amino acids", *Letters to Nature*, vol 368, pp. 651-653, (1994).

Gazit et al., "Mode of Action of the Antibacterial Cecropin B2: A Spectrofluorometric Study", *Biochemistry*, vol. 33, pp. 10681-10692, (1994).

Greenfield et al,, "Computer Circular Dichroism Spectra for the Evaluation of Protein Conformation", vol. 8, pp. 4108-4116, (1968).

Habermann et al., "Sequenzanalyse des Melittins aus den tryptischen und peptischan Spaltstücken", *Hoppe Seyler's Z. Physiol Chem.*, vol. 348, pp. 37-50, (1967).

Katchalski et al., "Synthesis and Chemical Properties of Poly-α- Amino Acids", *Adv. Protein Chem.*, vol. 13, pp. 243-492, (1958).

Kuchinka et al., "Interaction of Melittin with Phoshatidylcholine Membranes Binding Isotherm and Lipid Head-Group Conformation", *Biochemistry*, vol. 28, pp. 4216-4221, (1989).

Li et al., "Effect on electrophoretic mobility and antibacterial spectrum of removal of two residues from synthetic sarcotoxin IA and addition of the same residues to cecropin B", *FEBS Letters*, vol. 231, No. 2, pp. 299-302, (1988).

Loew et al., "Diffusion Potential Cascade. Convenient Defection of Transferable Membrane Pores", *Biochemistry*, vol. 22, pp. 837-844, (1983).

Merrifield et al., "Synthetic of Antibacterial Peptides Cecropin A (1-33)", *Biochemistry*, vol. 21, pp. 5020-5031, (1982).

Mor et al., "Isolation, Amino Acid Sequence, and Synthetic of Dermaseptin, a Novel Antimicrobial Peptide of Amphibian Skin", *Biochemistry*, vol. 30, pp. 8824-8830, (1991).

Okada et al., "Mode of action of a bactericidal protein induced in the haemolymph of *Sarcophage peregrina* (fleshfly) larvae", *Biochem. J.* vol. 222, pp. 119-124, (1984).

Oren et al., "A class of highly potent antibacterial peptides derived from pardaxin a pere-forming peptide isolated from Moses sole fish *Pardachirus marmoratus*", *Eur. J. Biochem.*, vol. 237, pp. 303-310, (1996).

Papahadjopoulos et al., "I. Structural Characteristics of Hydroted Liquid Crystals", *Biochim. Biophy. Acta*, vol. 135, pp. 624-638, (1967).

Perez-Paya et al., "Determination of the secondary structure of selected melittin analogues with different haemolytic activites", *Biochem. J.*, vol. 299, pp. 587-591, (1994).

Rapaport et al., "Aggregation and Organization of Pardaxin in Phospholipid Membranes", *The Journal of Biological Chemistry*, vol. 267, No. 10, pp. 6502-6509 (1992).

Rapaport et al., "Interaction of Fluorescently Labeled Pardaxin and Its Analogues with Lipid Bilayers", *The Journal of Biological Chemistry*, vol. 266, No. 35, pp. 23769-23775, (1991).

Rizzo et al., "Alamethicin Incorporation in Lipid Bilayers: A Thermodynamic Study", *Biochemistry*, vol. 26, pp. 2751-2759, (1987).

Hunter et al., "Fifty years of Antimicrobials: Past Perspectives and Future Trends", *Cambridge University Press*, pp. 67-85, (1995).

Schwarz et al., "Incorporation Kinetics in a membrane, studied with the pore-forming peptide alamethicin", *Biophys. J.*, vol. 52, pp. 685-692, (1987).

Segrest et al., "Amphipathic Helix Motif Classes and Properties", *PROTEINS: Structure, Function, and Genetics*, vol. 8, pp. 103-117, (1990).

Shai, "Molecular recognition between membrane-spanning polypeptides", *TIBS*, vol. 20, pp. 460-464, (1995).

Shai, "Pardaxin: channel formation by a shark repellant peptide from fish", *Toxicology*, vol. 87, pp. 109-129, (1994).

Shai et al., "Sequencing and synthesis of pardaxin, a polypeptide from the Red Sea Moses sole with ionophore activity", *FEBS Letters*, vol. 242, No. 1, pp. 161-166, (1988).

Shai et al., "pH-dependent Pore Formation Properties of Pardaxin Analogues", *The Journal of Biological Chemistry*, vol. 266, No. 33, pp. 22346-22354, (1991).

Shaw, "Lipid Composition as a Guide to the Classification of Bacteria", *Adv. Appl. Microbiol.*, vol. 17, pp. 63-108, (1974).

Sims et al., "Studies on the Mechanism by Which Cyanine Dyes Measure Membrane Potiential in Red Blood Cells and Phosphatidylcholine Vesicles", *Biochemistry*, vol. 13, No. 16, pp. 3315-3330, (1974).

Steiner et al, "Sequences and specificity of two antibacterial proteins involved in insect immunity", *Nature*, vol. 292, pp. 246-248, (1981).

Terwilliger et al., "The Structure of Melittin I. Structure Determination and Partial Refinement", *The Journal of Biological Chemistry*, vol. 257, No. 11, pp. 6010-6015, (1982).

Terwilliger et al., "The Structure of Melittin II. Interpretation of the Structure", *The Journal of Biological Chemistry*, vol. 257, No. 11, pp. 6016-6022, (1982).

Thompson et al., "Melittin-Like Peptides from the Shark-Repelling Defense Secretion of the sole *Pardachirus pavonious*", vol. 233, pp. 341-343, (1986).

Verkleij et al., "The Asymmetric Distribution of Phospholipids in the Human Red Cell Membrane: A Combined Study Using Phospholipases and Freeze-Etch Electron. Microscopy", *Biochem. Biophy. Acta,* vol. 323, pp. 173-193, (1973).

Wade et al., "A-D amino acid-containing channel-forming antibiotic peptides". *Proc. Natl. Acad. Sci.,* vol. 87, pp. 4761-4765, (1990).

Chuen-Shang et al., "Ordered Conformation of Polypeptides and Proteins in Acidic Dodecyl Sulfate Solution" *Biochemistry,* vol. 20, pp. 566-570, (1981).

Zagorski et al., "Solution Structure of Pardaxin P-2", *Biochemistry,* vol. 30, pp. 8009-8017, (1991).

Zahner et al., "The need for New Antibiotics: Possible ways forward", Institute of Biology II, University of Tubingen, pp. 67-84.

* cited by examiner

SEQUENCE LISTING (1) GENERAL INFORMATION:

(iii) NUMBER OF SEQUENCES: 99

(2) INFORMATION FOR SEQ ID NO: 1:

(i) SEQUENCE CHARACTERISTICS:
      (A) LENGTH: 33 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (B) CLONE: peptide 1

(ix) FEATURE:
      (A) NAME/KEY: Modified-site

```
            (B) LOCATION:group(7, 18, 19)
            (D) OTHER INFORMATION:/product= "D-amino acid residues"

(ix) FEATURE:
            (A) NAME/KEY: Modified-site
            (B) LOCATION:33
            (D) OTHER INFORMATION:/product= "OTHER"
                /note= "two aminoethylamino groups are attached at the C-
                terminus"

(xi) SEQUENCE DESCRIPTION: SEQ ID NO: 1:

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu (2) INFORMATION FOR SEQ ID NO: 2:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 2

(ix) FEATURE:
            (A) NAME/KEY: Modified-site
            (B) LOCATION:group(7, 18, 19)
            (D) OTHER INFORMATION:/product= "D-amino acid residues"

(ix) FEATURE:
            (A) NAME/KEY: Modified-site
            (B) LOCATION:22
            (D) OTHER INFORMATION:/product= "OTHER"
                /note= "an aminoethylamino group is attached at the C-
                terminus"

(xi) SEQUENCE DESCRIPTION: SEQ ID NO: 2:

Gly Phe Phe Ala Leu Ile Pro Lys Ile Ile Ser Ser Pro Leu Phe Lys
1               5                   10                  15

Thr Leu Leu Ser Ala Val
            20

(2) INFORMATION FOR SEQ ID NO: 3:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 3

(ix) FEATURE:
            (A) NAME/KEY: Modified-site
            (B) LOCATION:group(7, 18, 19)
            (D) OTHER INFORMATION:/product= "D-amino acid residues"

(xi) SEQUENCE DESCRIPTION: SEQ ID NO: 3:

Gly Phe Phe Ala Leu Ile Pro Lys Ile Ile Ser Ser Pro Leu Phe Lys
1               5                   10                  15

Thr Leu Leu Ser Ala Val
```

20

(2) INFORMATION FOR SEQ ID NO: 4:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 4

(ix) FEATURE:
        (A) NAME/KEY: Modified-site
        (B) LOCATION:group(8, 19, 20)
        (D) OTHER INFORMATION:/product= "D-amino acid residues"

(ix) FEATURE:
        (A) NAME/KEY: Modified-site
        (B) LOCATION:23
        (D) OTHER INFORMATION:/product= "OTHER"
            /note= "an aminoethylamino group is attached at the C-
            terminus"

(xi) SEQUENCE DESCRIPTION: SEQ ID NO: 4:

Lys Gly Phe Phe Ala Leu Ile Pro Lys Ile Ile Ser Ser Pro Leu Phe
1               5                   10                  15

Lys Thr Leu Leu Ser Ala Val
            20

(2) INFORMATION FOR SEQ ID NO: 5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 5

(ix) FEATURE:
        (A) NAME/KEY: Modified-site
        (B) LOCATION:group(9, 20, 21)
        (D) OTHER INFORMATION:/product= "D-amino acid residues"

(ix) FEATURE:
        (A) NAME/KEY: Modified-site
        (B) LOCATION:24
        (D) OTHER INFORMATION:/product= "OTHER"
            /note= "an aminoethylamino group is attached at the C-
            terminus"

(xi) SEQUENCE DESCRIPTION: SEQ ID NO: 5:

Lys Lys Gly Phe Phe Ala Leu Ile Pro Lys Ile Ile Ser Ser Pro Leu
1               5                   10                  15

Phe Lys Thr Leu Leu Ser Ala Val
            20

(2) INFORMATION FOR SEQ ID NO: 6:

(i) SEQUENCE CHARACTERISTICS:
        (A) LENGTH: 24 amino acids
        (B) TYPE: amino acid
        (C) STRANDEDNESS: single
        (D) TOPOLOGY: linear

```
        (ii) MOLECULE TYPE: peptide (vii) IMMEDIATE SOURCE:
            (B) CLONE: peptide 6

(ix) FEATURE:
            (A) NAME/KEY: Modified-site
            (B) LOCATION:group(9, 20, 21)
            (D) OTHER INFORMATION:/product= "D-amino acid residues"

(xi) SEQUENCE DESCRIPTION: SEQ ID NO: 6:

Lys Lys Gly Phe Phe Ala Leu Ile Pro Lys Ile Ile Ser Ser Pro Leu
1               5                   10                  15

Phe Lys Thr Leu Leu Ser Ala Val
            20

(2) INFORMATION FOR SEQ ID NO: 7:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 7

(ix) FEATURE:
            (A) NAME/KEY: Modified-site
            (B) LOCATION:7
            (D) OTHER INFORMATION:/product= "D-AMINO ACID RESIDUE"

(ix) FEATURE:
            (A) NAME/KEY: Modified-site
            (B) LOCATION:11
            (D) OTHER INFORMATION:/product= "OTHER"
                /note= "AN AMINOETHYLAMINO GROUP IS ATTACHED AT THE C-
                TERMINUS"

(xi) SEQUENCE DESCRIPTION: SEQ ID NO: 7:

Gly Phe Phe Ala Leu Ile Pro Lys Ile Ile Ser
1               5                   10

(2) INFORMATION FOR SEQ ID NO: 8:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (v) FRAGMENT TYPE: linear (vii) IMMEDIATE SOURCE:
            (B) CLONE: peptide 8

(ix) FEATURE:
            (A) NAME/KEY: Modified-site
            (B) LOCATION:33
            (D) OTHER INFORMATION:/product= "OTHER"
                /note= "TWO AMINOETHYLAMINO GROUPS ARE ATTACHED AT THE C-
                TERMINUS"

(xi) SEQUENCE DESCRIPTION: SEQ ID NO: 8:

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30
```

Glu (2) INFORMATION FOR SEQ ID NO: 9:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 9

(ix) FEATURE:
        (A) NAME/KEY: Modified-site
        (B) LOCATION:13
        (D) OTHER INFORMATION:/product= "D-AMINO ACID RESIDUE"

(ix) FEATURE:
        (A) NAME/KEY: Modified-site
        (B) LOCATION:33
        (D) OTHER INFORMATION:/product= "OTHER"
            /note= "TWO AMINOETHYLAMINO GROUPS ARE ATTACHED AT THE C-
            TERMINUS"

(xi) SEQUENCE DESCRIPTION: SEQ ID NO: 9:

```
Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu
```

(2) INFORMATION FOR SEQ ID NO: 10:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (v) FRAGMENT TYPE: linear (vii) IMMEDIATE SOURCE:
        (B) CLONE: peptide 10

(ix) FEATURE:
        (A) NAME/KEY: Modified-site
        (B) LOCATION:group(5, 19)
        (D) OTHER INFORMATION:/product= "D-AMINO ACID RESIDUES"

(ix) FEATURE:
        (A) NAME/KEY: Modified-site
        (B) LOCATION:33
        (D) OTHER INFORMATION:/product= "OTHER"
            /note= "TWO AMINOETHYLAMINO GROUPS ARE ATTACHED AT THE C-
            TERMINUS"

(xi) SEQUENCE DESCRIPTION: SEQ ID NO: 10:

```
Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu
```

(2) INFORMATION FOR SEQ ID NO: 11:

```
        (i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (v) FRAGMENT TYPE: linear (vii) IMMEDIATE SOURCE:
            (A) LIBRARY: peptide 11

(ix) FEATURE:
            (A) NAME/KEY: Modified-site
            (B) LOCATION:group(7, 19)
            (D) OTHER INFORMATION:/product= "D-AMINO ACID RESIDUES"

(ix) FEATURE:
            (A) NAME/KEY: Modified-site
            (B) LOCATION:33
            (D) OTHER INFORMATION:/product= "OTHER"
                /note= "TWO AMINOETHYLAMINO GROUPS ARE ATTACHED AT THE C-
                TERMINUS"

(xi) SEQUENCE DESCRIPTION: SEQ ID NO: 11:

Gly Phe Phe Ala Leu Ile Pro Lys Ile Ile Ser Ser Pro Leu Phe Lys
1               5                  10                  15

Thr Leu Leu Ser Ala Val Gly Ser Ala Leu Ser Ser Ser Gly Gly Gln
            20                  25                  30

Glu (2) INFORMATION FOR SEQ ID NO: 12:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 12

(ix) FEATURE:
            (A) NAME/KEY: Modified-site
            (B) LOCATION:7
            (D) OTHER INFORMATION:/product= "D-AMINO ACID RESIDUE"

(ix) FEATURE:
            (A) NAME/KEY: Modified-site
            (B) LOCATION:33
            (D) OTHER INFORMATION:/product= "OTHER"
                /note= "TWO AMINOETHYLAMINO GROUPS ARE ATTACHED AT THE C-
                TERMINUS"

(xi) SEQUENCE DESCRIPTION: SEQ ID NO: 12:

Gly Phe Phe Ala Leu Ile Pro Lys Ile Ile Ser Ser Pro Leu Phe Lys
1               5                  10                  15

Thr Leu Leu Ser Ala Val Gly Ser Ala Leu Ser Ser Ser Gly Gly Gln
            20                  25                  30

Glu (2) INFORMATION FOR SEQ ID NO: 13:

(i) SEQUENCE CHARACTERISTICS:
            (A) LENGTH: 33 amino acids
            (B) TYPE: amino acid
            (C) STRANDEDNESS: single
```

```
        (D) TOPOLOGY: linear (ii) MOLECULE TYPE: peptide (vii) IMMEDIATE SOURCE:
         (B) CLONE: peptide 13

(ix) FEATURE:
         (A) NAME/KEY: Modified-site
         (B) LOCATION:7
         (D) OTHER INFORMATION:/product= "D-AMINO ACID RESIDUE"

(xi) SEQUENCE DESCRIPTION: SEQ ID NO: 13:

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu (2) INFORMATION FOR SEQ ID NO: 14:

(i) SEQUENCE CHARACTERISTICS:
         (A) LENGTH: 33 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: peptide 14

(ix) FEATURE:
         (A) NAME/KEY: Modified-site
         (B) LOCATION:group(18, 19)
         (D) OTHER INFORMATION:/product= "D-AMINO ACID RESIDUES"

(ix) FEATURE:
         (A) NAME/KEY: Modified-site
         (B) LOCATION:33
         (D) OTHER INFORMATION:/product= "OTHER"
             /note= "TWO AMINOETHYLAMINO GROUPS ARE ATTACHED TO THE C-
             TERMINUS"

(xi) SEQUENCE DESCRIPTION: SEQ ID NO: 14:

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu (2) INFORMATION FOR SEQ ID NO: 15:

(i) SEQUENCE CHARACTERISTICS:
         (A) LENGTH: 33 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: peptide 15

(ix) FEATURE:
         (A) NAME/KEY: Modified-site
         (B) LOCATION:group(18, 19)
         (D) OTHER INFORMATION:/product= "D-AMINO ACID RESIDUES"

(xi) SEQUENCE DESCRIPTION: SEQ ID NO: 15:
```

```
Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu (2) INFORMATION FOR SEQ ID NO: 16:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 16

(ix) FEATURE:
        (A) NAME/KEY: Modified-site
        (B) LOCATION:group(7, 18, 19)
        (D) OTHER INFORMATION:/product= "D-AMINO ACID RESIDUES"

(xi) SEQUENCE DESCRIPTION: SEQ ID NO: 16:

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu (2) INFORMATION FOR SEQ ID NO: 17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 17

(ix) FEATURE:
        (A) NAME/KEY: Modified-site
        (B) LOCATION:7
        (D) OTHER INFORMATION:/product= "D-AMINO ACID RESIDUE"

(ix) FEATURE:
        (A) NAME/KEY: Modified-site
        (B) LOCATION:22
        (D) OTHER INFORMATION:/product= "OTHER"
            /note= "AN AMINOETHYLAMINO GROUP IS ATTACHED AT THE C-
            TERMINUS"

(xi) SEQUENCE DESCRIPTION: SEQ ID NO: 17:

Gly Phe Phe Ala Leu Ile Pro Lys Ile Ile Ser Ser Pro Leu Phe Lys
1               5                   10                  15

Thr Leu Leu Ser Ala Val
            20

(2) INFORMATION FOR SEQ ID NO: 18:

(i) SEQUENCE CHARACTERISTICS:
        (A) LENGTH: 26 amino acids
        (B) TYPE: amino acid
        (C) STRANDEDNESS: single
        (D) TOPOLOGY: linear
```

```
        (ii) MOLECULE TYPE: peptide (vii) IMMEDIATE SOURCE:
              (B) CLONE: peptide 18

(ix) FEATURE:
              (A) NAME/KEY: Modified-site
              (B) LOCATION:group(5, 8, 17, 21)
              (D) OTHER INFORMATION:/product= "D-amino acid residues"

(ix) FEATURE:
              (A) NAME/KEY: Modified-site
              (B) LOCATION:26
              (D) OTHER INFORMATION:/product= "OTHER"
                  /note= "the carboxyl group at the C-terminus is replaced
                  by an amino group"

(xi) SEQUENCE DESCRIPTION: SEQ ID NO: 18:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

(2) INFORMATION FOR SEQ ID NO: 19:

(i) SEQUENCE CHARACTERISTICS:
              (A) LENGTH: 26 amino acids
              (B) TYPE: amino acid
              (C) STRANDEDNESS: single
              (D) TOPOLOGY: linear (ii) MOLECULE TYPE: peptide (vii) IMMEDIATE SOURCE:
              (B) CLONE: peptide 19

(ix) FEATURE:
              (A) NAME/KEY: Modified-site
              (B) LOCATION:group(5, 8, 17, 21)
              (D) OTHER INFORMATION:/product= "D-amino acid residues"

(xi) SEQUENCE DESCRIPTION: SEQ ID NO: 19:

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

(2) INFORMATION FOR SEQ ID NO: 20:

(i) SEQUENCE CHARACTERISTICS:
              (A) LENGTH: 22 amino acids
              (B) TYPE: amino acid
              (C) STRANDEDNESS: single
              (D) TOPOLOGY: linear (ii) MOLECULE TYPE: peptide (vii) IMMEDIATE SOURCE:
              (B) CLONE: peptide 20

(ix) FEATURE:
              (A) NAME/KEY: Modified-site
              (B) LOCATION:group(5, 8, 17, 21)
              (D) OTHER INFORMATION:/product= "D-amino acid residues"

(ix) FEATURE:
              (A) NAME/KEY: Modified-site
              (B) LOCATION:22
              (D) OTHER INFORMATION:/product= "OTHER"
                  /note= "an aminoethylamino group is attached at the C-
                  terminus"
```

(xi) SEQUENCE DESCRIPTION: SEQ ID NO: 20:

Gly Ile Gly Ala Val Leu Lys Val Leu Thr Thr Gly Leu Pro Ala Leu
1               5                   10                  15

Ile Ser Trp Ile Lys Arg
            20

(2) INFORMATION FOR SEQ ID NO: 21:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 21

(ix) FEATURE:
        (A) NAME/KEY: Modified-site
        (B) LOCATION:group(2, 5, 14, 18)
        (D) OTHER INFORMATION:/product= "D-amino acid residues"

(ix) FEATURE:
        (A) NAME/KEY: Modified-site
        (B) LOCATION:19
        (D) OTHER INFORMATION:/product= "OTHER"
            /note= "an aminoethylamino group is attached at the C-
            terminus"

(xi) SEQUENCE DESCRIPTION: SEQ ID NO: 21:

Ala Val Leu Lys Val Leu Thr Thr Gly Leu Pro Ala Leu Ile Ser Trp
1               5                   10                  15

Ile Lys Arg (2) INFORMATION FOR SEQ ID NO: 22:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 22

(ix) FEATURE:
        (A) NAME/KEY: Modified-site
        (B) LOCATION:group(3, 4, 8, 10)
        (D) OTHER INFORMATION:/product= "D-amino acid residues"

(ix) FEATURE:
        (A) NAME/KEY: Modified-site
        (B) LOCATION:12
        (D) OTHER INFORMATION:/product= "OTHER"
            /note= "the carboxyl group at the C-terminus is replaced
            by an amino group"

(xi) SEQUENCE DESCRIPTION: SEQ ID NO: 22:

Lys Leu Leu Leu Leu Leu Lys Leu Leu Leu Leu Lys
1               5                   10

(2) INFORMATION FOR SEQ ID NO: 23:

(i) SEQUENCE CHARACTERISTICS:
        (A) LENGTH: 12 amino acids
        (B) TYPE: amino acid
        (C) STRANDEDNESS: single

```
            (D) TOPOLOGY: linear (ii) MOLECULE TYPE: peptide (vii) IMMEDIATE SOURCE:
            (B) CLONE: peptide 23

(ix) FEATURE:
            (A) NAME/KEY: Modified-site
            (B) LOCATION:group(3, 4, 8, 10)
            (D) OTHER INFORMATION:/product= "D-amino acid residues"

(ix) FEATURE:
            (A) NAME/KEY: Modified-site
            (B) LOCATION:12
            (D) OTHER INFORMATION:/product= "OTHER"
                /note= "the carboxyl group at the C-terminus is replaced
                by an amino group"

(xi) SEQUENCE DESCRIPTION: SEQ ID NO: 23:

Lys Leu Leu Leu Lys Leu Leu Leu Lys Leu Leu Lys
1               5                   10

(2) INFORMATION FOR SEQ ID NO: 24:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 24

(ix) FEATURE:
            (A) NAME/KEY: Modified-site
            (B) LOCATION:group(3, 4, 8, 10)
            (D) OTHER INFORMATION:/product= "D-amino acid residues"

(ix) FEATURE:
            (A) NAME/KEY: Modified-site
            (B) LOCATION:12
            (D) OTHER INFORMATION:/product= "OTHER"
                /note= "the carboxyl group at the C-terminus is replaced
                by an amino group"

(xi) SEQUENCE DESCRIPTION: SEQ ID NO: 24:

Lys Leu Leu Leu Lys Leu Lys Leu Lys Leu Leu Lys
1               5                   10

(2) INFORMATION FOR SEQ ID NO: 25:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 25

(ix) FEATURE:
            (A) NAME/KEY: Modified-site
            (B) LOCATION:group(3, 4, 8, 10)
            (D) OTHER INFORMATION:/product= "D-amino acid residues"

(ix) FEATURE:
            (A) NAME/KEY: Modified-site
            (B) LOCATION:12
            (D) OTHER INFORMATION:/product= "OTHER"
                /note= "the carboxyl group at the C-terminus is replaced
``` by an amino group"

(xi) SEQUENCE DESCRIPTION: SEQ ID NO: 25:

Lys Lys Leu Leu Lys Leu Lys Leu Lys Leu Lys Lys
1               5                   10

(2) INFORMATION FOR SEQ ID NO: 26:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 26

(ix) FEATURE:
            (A) NAME/KEY: Modified-site
            (B) LOCATION:group(1, 2, 5, 6, 7, 9, 11, 12)
            (D) OTHER INFORMATION:/product= "D-amino acid residues"

(ix) FEATURE:
            (A) NAME/KEY: Modified-site
            (B) LOCATION:12
            (D) OTHER INFORMATION:/product= "OTHER"
                /note= "the carboxyl group at the C-terminus is replaced
                by an amino group"

(xi) SEQUENCE DESCRIPTION: SEQ ID NO: 26:

Lys Leu Leu Leu Lys Leu Leu Leu Lys Leu Leu Lys
1               5                   10

(2) INFORMATION FOR SEQ ID NO: 27:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 27

(ix) FEATURE:
            (A) NAME/KEY: Modified-site
            (B) LOCATION:group(1, 2, 5, 6, 7, 9, 11, 12)
            (D) OTHER INFORMATION:/product= "D-amino acid residues"

(ix) FEATURE:
            (A) NAME/KEY: Modified-site
            (B) LOCATION:12
            (D) OTHER INFORMATION:/product= "OTHER"
                /note= "the carboxyl group at the C-terminus is replaced
                by an amino group"

(xi) SEQUENCE DESCRIPTION: SEQ ID NO: 27:

Lys Leu Leu Leu Lys Leu Lys Leu Lys Leu Leu Lys
1               5                   10

(2) INFORMATION FOR SEQ ID NO: 28:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide

```
       (vii) IMMEDIATE SOURCE:
             (B) CLONE: peptide 28

(ix) FEATURE:
             (A) NAME/KEY: Modified-site
             (B) LOCATION:group(2, 4)
             (D) OTHER INFORMATION:/product= "D-amino acid residues"

(xi) SEQUENCE DESCRIPTION: SEQ ID NO: 28:

Lys Leu Leu Leu Leu Lys
1               5

(2) INFORMATION FOR SEQ ID NO: 29:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (vii) IMMEDIATE SOURCE:
             (B) CLONE: peptide 29

(ix) FEATURE:
             (A) NAME/KEY: Modified-site
             (B) LOCATION:group(2, 4, 6)
             (D) OTHER INFORMATION:/product= "D-amino acid residues"

(xi) SEQUENCE DESCRIPTION: SEQ ID NO: 29:

Lys Leu Leu Leu Lys Leu Leu Lys
1               5

(2) INFORMATION FOR SEQ ID NO: 30:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (vii) IMMEDIATE SOURCE:
             (B) CLONE: peptide 30

(ix) FEATURE:
             (A) NAME/KEY: Modified-site
             (B) LOCATION:group(2, 6, 8, 11)
             (D) OTHER INFORMATION:/product= "D-amino acid residues"

(xi) SEQUENCE DESCRIPTION: SEQ ID NO: 30:

Lys Leu Leu Leu Lys Leu Lys Leu Lys Leu Leu Lys
1               5                  10

(2) INFORMATION FOR SEQ ID NO: 31:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (vii) IMMEDIATE SOURCE:
             (B) CLONE: peptide 31

(ix) FEATURE:
             (A) NAME/KEY: Modified-site
             (B) LOCATION:group(2, 3, 4, 8, 10, 11)
```

(D) OTHER INFORMATION:/product= "D-amino acid residues"

(xi) SEQUENCE DESCRIPTION: SEQ ID NO: 31:

Lys Leu Leu Leu Lys Leu Lys Leu Lys Leu Leu Lys
1               5                   10

(2) INFORMATION FOR SEQ ID NO: 32:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 32

(ix) FEATURE:
        (A) NAME/KEY: Modified-site
        (B) LOCATION:group(3, 5, 8, 9, 11)
        (D) OTHER INFORMATION:/product= "D-amino acid residues"

(xi) SEQUENCE DESCRIPTION: SEQ ID NO: 32:

Lys Leu Leu Leu Lys Leu Lys Leu Lys Leu Leu Lys
1               5                   10

(2) INFORMATION FOR SEQ ID NO: 33:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 33

(ix) FEATURE:
        (A) NAME/KEY: Modified-site
        (B) LOCATION:group(3, 4, 8, 10)
        (D) OTHER INFORMATION:/product= "D-amino acid residues"

(ix) FEATURE:
        (A) NAME/KEY: Modified-site
        (B) LOCATION:12
        (D) OTHER INFORMATION:/product= "OTHER"
            /note= "the carboxyl group at the C-terminus is replaced
            by an amino group"

(xi) SEQUENCE DESCRIPTION: SEQ ID NO: 33:

Lys Ala Ala Ala Lys Ala Ala Ala Lys Ala Ala Lys
1               5                   10

(2) INFORMATION FOR SEQ ID NO: 34:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 34

(ix) FEATURE:
        (A) NAME/KEY: Modified-site
        (B) LOCATION:group(3, 4, 8, 10)

```
            (D) OTHER INFORMATION:/product= "D-amino acid residues"

(ix) FEATURE:
            (A) NAME/KEY: Modified-site
            (B) LOCATION:12
            (D) OTHER INFORMATION:/product= "OTHER"
                /note= "the carboxyl group at the C-terminus is replaced
                by an amino group"

(xi) SEQUENCE DESCRIPTION: SEQ ID NO: 34:

Lys Val Val Val Lys Val Val Val Lys Val Val Lys
1               5                  10

(2) INFORMATION FOR SEQ ID NO: 35:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 35

(ix) FEATURE:
            (A) NAME/KEY: Modified-site
            (B) LOCATION:group(2, 6, 8, 11)
            (D) OTHER INFORMATION:/product= "D-amino acid residues"

(xi) SEQUENCE DESCRIPTION: SEQ ID NO: 35:

Lys Val Val Val Lys Val Lys Val Lys Val Val Lys
1               5                  10

(2) INFORMATION FOR SEQ ID NO: 36:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 36

(ix) FEATURE:
            (A) NAME/KEY: Modified-site
            (B) LOCATION:group(1..4, 8, 10, 11)
            (D) OTHER INFORMATION:/product= "D-amino acid residues"

(xi) SEQUENCE DESCRIPTION: SEQ ID NO: 36:

Lys Val Val Val Lys Val Lys Val Lys Val Val Lys
1               5                  10

(2) INFORMATION FOR SEQ ID NO: 37:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 37

(ix) FEATURE:
            (A) NAME/KEY: Modified-site
            (B) LOCATION:group(3, 5, 8, 9, 11)
```

(D) OTHER INFORMATION:/product= "D-amino acid residues"

(xi) SEQUENCE DESCRIPTION: SEQ ID NO: 37:

Lys Val Val Val Lys Val Lys Val Lys Val Val Lys
1               5                   10

(2) INFORMATION FOR SEQ ID NO: 38:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 38

(ix) FEATURE:
        (A) NAME/KEY: Modified-site
        (B) LOCATION:group(2, 6)
        (D) OTHER INFORMATION:/product= "D-amino acid residues"

(xi) SEQUENCE DESCRIPTION: SEQ ID NO: 38:

Lys Leu Ile Leu Lys Leu
1               5

(2) INFORMATION FOR SEQ ID NO: 39:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 39

(ix) FEATURE:
        (A) NAME/KEY: Modified-site
        (B) LOCATION:group(2, 6)
        (D) OTHER INFORMATION:/product= "D-amino acid residues"

(xi) SEQUENCE DESCRIPTION: SEQ ID NO: 39:

Lys Val Leu His Leu Leu
1               5

(2) INFORMATION FOR SEQ ID NO: 40:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 40

(ix) FEATURE:
        (A) NAME/KEY: Modified-site
        (B) LOCATION:group(2, 6)
        (D) OTHER INFORMATION:/product= "D-amino acid residues"

(xi) SEQUENCE DESCRIPTION: SEQ ID NO: 40:

Leu Lys Leu Arg Leu Leu
1               5

(2) INFORMATION FOR SEQ ID NO: 41:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 41

(ix) FEATURE:
        (A) NAME/KEY: Modified-site
        (B) LOCATION:4
        (D) OTHER INFORMATION:/product= "D-amino acid residue"

(xi) SEQUENCE DESCRIPTION: SEQ ID NO: 41:

Lys Pro Leu His Leu Leu
1           5

(2) INFORMATION FOR SEQ ID NO: 42:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 42

(ix) FEATURE:
        (A) NAME/KEY: Modified-site
        (B) LOCATION:group(2, 3, 4, 6)
        (D) OTHER INFORMATION:/product= "D-amino acid residues"

(xi) SEQUENCE DESCRIPTION: SEQ ID NO: 42:

Lys Leu Ile Leu Lys Leu Val Arg
1           5

(2) INFORMATION FOR SEQ ID NO: 43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 43

(ix) FEATURE:
        (A) NAME/KEY: Modified-site
        (B) LOCATION:group(2, 4, 5, 6)
        (D) OTHER INFORMATION:/product= "D-amino acid residues"

(xi) SEQUENCE DESCRIPTION: SEQ ID NO: 43:

Lys Val Phe His Leu Leu His Leu
1           5

(2) INFORMATION FOR SEQ ID NO: 44:

(i) SEQUENCE CHARACTERISTICS:
        (A) LENGTH: 8 amino acids
        (B) TYPE: amino acid
        (C) STRANDEDNESS: single

```
            (D) TOPOLOGY: linear (ii) MOLECULE TYPE: peptide (vii) IMMEDIATE SOURCE:
            (B) CLONE: peptide 44

(ix) FEATURE:
            (A) NAME/KEY: Modified-site
            (B) LOCATION:group(1, 2, 4, 6, 7)
            (D) OTHER INFORMATION:/product= "D-amino acid residues"

(xi) SEQUENCE DESCRIPTION: SEQ ID NO: 44:

His Lys Phe Arg Ile Leu Lys Leu
1               5

(2) INFORMATION FOR SEQ ID NO: 45:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 45

(ix) FEATURE:
            (A) NAME/KEY: Modified-site
            (B) LOCATION:5
            (D) OTHER INFORMATION:/product= "D-amino acid residue"

(xi) SEQUENCE DESCRIPTION: SEQ ID NO: 45:

Lys Pro Phe His Ile Leu His Leu
1               5

(2) INFORMATION FOR SEQ ID NO: 46:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 46

(ix) FEATURE:
            (A) NAME/KEY: Modified-site
            (B) LOCATION:group(1, 2, 6, 8, 11)
            (D) OTHER INFORMATION:/product= "D-amino acid residues"

(xi) SEQUENCE DESCRIPTION: SEQ ID NO: 46:

Lys Ile Ile Ile Lys Ile Lys Ile Lys Ile Ile Lys
1               5                   10

(2) INFORMATION FOR SEQ ID NO: 47:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 47
```

```
      (ix) FEATURE:
           (A) NAME/KEY: Modified-site
           (B) LOCATION:group(2, 3, 4, 8, 10, 11)
           (D) OTHER INFORMATION:/product= "D-amino acid residues"

(xi) SEQUENCE DESCRIPTION: SEQ ID NO: 47:

Lys Ile Ile Ile Lys Ile Lys Ile Lys Ile Ile Lys
1               5                  10

(2) INFORMATION FOR SEQ ID NO: 48:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (vii) IMMEDIATE SOURCE:
          (B) CLONE: peptide 48

(ix) FEATURE:
          (A) NAME/KEY: Modified-site
          (B) LOCATION:group(1, 3, 5, 8, 9, 11)
          (D) OTHER INFORMATION:/product= "D-amino acid residues"

(xi) SEQUENCE DESCRIPTION: SEQ ID NO: 48:

Lys Ile Ile Ile Lys Ile Lys Ile Lys Ile Ile Lys
1               5                  10

(2) INFORMATION FOR SEQ ID NO: 49:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (vii) IMMEDIATE SOURCE:
          (B) CLONE: peptide 49

(ix) FEATURE:
          (A) NAME/KEY: Modified-site
          (B) LOCATION:7
          (D) OTHER INFORMATION:/product= "D-amino acid recidue"

(xi) SEQUENCE DESCRIPTION: SEQ ID NO: 49:

Lys Ile Pro Ile Lys Ile Lys Ile Lys Ile Pro Lys
1               5                  10

(2) INFORMATION FOR SEQ ID NO: 50:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (vii) IMMEDIATE SOURCE:
          (B) CLONE: peptide 50

(ix) FEATURE:
          (A) NAME/KEY: Modified-site
          (B) LOCATION:group(6, 10)
          (D) OTHER INFORMATION:/product= "D-amino acid residues"

(xi) SEQUENCE DESCRIPTION: SEQ ID NO: 50:
```

```
Lys Ile Pro Ile Lys Ile Lys Ile Lys Ile Val Lys
1               5                   10
```

(2) INFORMATION FOR SEQ ID NO: 51:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 51

(ix) FEATURE:
        (A) NAME/KEY: Modified-site
        (B) LOCATION:group(2, 4, 6, 8, 11)
        (D) OTHER INFORMATION:/product= "D-amino acid residues"

(xi) SEQUENCE DESCRIPTION: SEQ ID NO: 51:

```
Arg Ile Ile Ile Arg Ile Arg Ile Arg Ile Ile Arg
1               5                   10
```

(2) INFORMATION FOR SEQ ID NO: 52:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 52

(ix) FEATURE:
        (A) NAME/KEY: Modified-site
        (B) LOCATION:group(2, 3, 4, 6, 7, 8, 10, 11)
        (D) OTHER INFORMATION:/product= "D-amino acid residues"

(xi) SEQUENCE DESCRIPTION: SEQ ID NO: 52:

```
Arg Ile Ile Ile Arg Ile Arg Ile Arg Ile Ile Arg
1               5                   10
```

(2) INFORMATION FOR SEQ ID NO: 53:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 53

(ix) FEATURE:
        (A) NAME/KEY: Modified-site
        (B) LOCATION:group(1, 3, 5, 8, 9, 11)
        (D) OTHER INFORMATION:/product= "D-amino acid residues"

(xi) SEQUENCE DESCRIPTION: SEQ ID NO: 53:

```
Arg Ile Ile Ile Arg Ile Arg Ile Arg Ile Ile Arg
1               5                   10
```

(2) INFORMATION FOR SEQ ID NO: 54:

(i) SEQUENCE CHARACTERISTICS:

(A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 54

(ix) FEATURE:
            (A) NAME/KEY: Modified-site
            (B) LOCATION:group(2, 6, 8, 11)
            (D) OTHER INFORMATION:/product= "D-amino acid residues"

(xi) SEQUENCE DESCRIPTION: SEQ ID NO: 54:

Arg Ile Val Ile Arg Ile Arg Ile Arg Leu Ile Arg
1               5                   10

(2) INFORMATION FOR SEQ ID NO: 55:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 55

(ix) FEATURE:
            (A) NAME/KEY: Modified-site
            (B) LOCATION:group(2, 3, 4, 8, 10, 11)
            (D) OTHER INFORMATION:/product= "D-amino acid residues"

(xi) SEQUENCE DESCRIPTION: SEQ ID NO: 55:

Arg Ile Ile Val Arg Ile Arg Leu Arg Ile Ile Arg
1               5                   10

(2) INFORMATION FOR SEQ ID NO: 56:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 56

(ix) FEATURE:
            (A) NAME/KEY: Modified-site
            (B) LOCATION:group(3, 5, 8, 9, 11)
            (D) OTHER INFORMATION:/product= "D-amino acid residues"

(xi) SEQUENCE DESCRIPTION: SEQ ID NO: 56:

Arg Ile Gly Ile Arg Leu Arg Val Arg Ile Ile Arg
1               5                   10

(2) INFORMATION FOR SEQ ID NO: 57:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide

```
    (vii) IMMEDIATE SOURCE:
          (B) CLONE: peptide 57

(ix) FEATURE:
         (A) NAME/KEY: Modified-site
         (B) LOCATION:group(2, 6, 8, 11)
         (D) OTHER INFORMATION:/product= "D-amino acid residues"

(xi) SEQUENCE DESCRIPTION: SEQ ID NO: 57:

Lys Ile Val Ile Arg Ile Arg Ile Arg Leu Ile Arg
1               5                   10

(2) INFORMATION FOR SEQ ID NO: 58:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
          (B) CLONE: peptide 58

(ix) FEATURE:
         (A) NAME/KEY: Modified-site
         (B) LOCATION:group(2, 3, 4, 8, 10, 11)
         (D) OTHER INFORMATION:/product= "D-amino acid residues"

(xi) SEQUENCE DESCRIPTION: SEQ ID NO: 58:

Arg Ile Ala Val Lys Trp Arg Leu Arg Phe Ile Lys
1               5                   10

(2) INFORMATION FOR SEQ ID NO: 59:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
          (B) CLONE: peptide 59

(ix) FEATURE:
         (A) NAME/KEY: Modified-site
         (B) LOCATION:group(3, 5, 8, 9, 11)
         (D) OTHER INFORMATION:/product= "D-amino acid residues"

(xi) SEQUENCE DESCRIPTION: SEQ ID NO: 59:

Lys Ile Gly Trp Lys Leu Arg Val Arg Ile Ile Arg
1               5                   10

(2) INFORMATION FOR SEQ ID NO: 60:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vii) IMMEDIATE SOURCE:
          (B) CLONE: peptide 60

(ix) FEATURE:
         (A) NAME/KEY: Modified-site
         (B) LOCATION:group(2, 4, 7, 10, 11)
         (D) OTHER INFORMATION:/product= "D-amino acid residues"
```

(xi) SEQUENCE DESCRIPTION: SEQ ID NO: 60:

Lys Lys Ile Gly Trp Leu Ile Ile Arg Val Arg Arg
1               5                   10

(2) INFORMATION FOR SEQ ID NO: 61:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 61

(ix) FEATURE:
        (A) NAME/KEY: Modified-site
        (B) LOCATION:group(2, 6, 8, 11, 13)
        (D) OTHER INFORMATION:/product= "D-amino acid residues"

(xi) SEQUENCE DESCRIPTION: SEQ ID NO: 61:

Arg Ile Val Ile Arg Ile Arg Ile Arg Leu Ile Arg Ile Arg
1               5                   10

(2) INFORMATION FOR SEQ ID NO: 62:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 62

(ix) FEATURE:
        (A) NAME/KEY: Modified-site
        (B) LOCATION:group(1..4, 8, 10, 11, 13, 14)
        (D) OTHER INFORMATION:/product= "D-amino acid residues"

(xi) SEQUENCE DESCRIPTION: SEQ ID NO: 62:

Arg Ile Ile Val Arg Ile Arg Leu Arg Ile Ile Arg Val Arg
1               5                   10

(2) INFORMATION FOR SEQ ID NO: 63:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 63

(ix) FEATURE:
        (A) NAME/KEY: Modified-site
        (B) LOCATION:group(3, 5, 8, 9, 11, 14)
        (D) OTHER INFORMATION:/product= "D-amino acid residues"

(xi) SEQUENCE DESCRIPTION: SEQ ID NO: 63:

Arg Ile Gly Ile Arg Leu Arg Val Arg Ile Ile Arg Arg Val
1               5                   10

```
(2) INFORMATION FOR SEQ ID NO: 64:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 64

(ix) FEATURE:
        (A) NAME/KEY: Modified-site
        (B) LOCATION:group(1, 2, 6, 7, 11, 15, 16)

(xi) SEQUENCE DESCRIPTION: SEQ ID NO: 64:

Lys Ile Val Ile Arg Ile Arg Ala Arg Leu Ile Arg Ile Arg Ile Arg
1               5                   10                  15

(2) INFORMATION FOR SEQ ID NO: 65:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 65

(ix) FEATURE:
        (A) NAME/KEY: Modified-site
        (B) LOCATION:group(2, 3, 4, 7, 8, 10, 11, 13, 14, 16)
        (D) OTHER INFORMATION:/product= "D-amino acid residues"

(xi) SEQUENCE DESCRIPTION: SEQ ID NO: 65:

Arg Ile Ile Val Lys Ile Arg Leu Arg Ile Ile Lys Lys Ile Arg Leu
1               5                   10                  15

(2) INFORMATION FOR SEQ ID NO: 66:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 66

(ix) FEATURE:
        (A) NAME/KEY: Modified-site
        (B) LOCATION:group(1, 3, 5, 8, 9, 11, 13, 14, 16)
        (D) OTHER INFORMATION:/product= "D-amino acid residues"

(xi) SEQUENCE DESCRIPTION: SEQ ID NO: 66:

Lys Ile Gly Ile Lys Ala Arg Val Arg Ile Ile Arg Val Lys Ile Ile
1               5                   10                  15

(2) INFORMATION FOR SEQ ID NO: 67:

(i) SEQUENCE CHARACTERISTICS:
        (A) LENGTH: 16 amino acids
        (B) TYPE: amino acid
        (C) STRANDEDNESS: single
        (D) TOPOLOGY: linear
```

```
    (ii) MOLECULE TYPE: peptide (vii) IMMEDIATE SOURCE:
         (B) CLONE: peptide 67

(ix) FEATURE:
         (A) NAME/KEY: Modified-site
         (B) LOCATION:group(2, 3, 4, 7, 8, 10, 11, 13, 14, 16)
         (D) OTHER INFORMATION:/product= "D-amino acid residues"

(xi) SEQUENCE DESCRIPTION: SEQ ID NO: 67:

Arg Ile Ile Val His Ile Arg Leu Arg Ile Ile His His Ile Arg Leu
1               5                   10                  15

(2) INFORMATION FOR SEQ ID NO: 68:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: peptide 68

(ix) FEATURE:
         (A) NAME/KEY: Modified-site
         (B) LOCATION:group(1, 3, 5, 8, 9, 11, 13, 14, 16)
         (D) OTHER INFORMATION:/product= "D-amino acid residues"

(xi) SEQUENCE DESCRIPTION: SEQ ID NO: 68:

His Ile Gly Ile Lys Ala His Val Arg Ile Ile Arg Val His Ile Ile
1               5                   10                  15

(2) INFORMATION FOR SEQ ID NO: 69:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: peptide 69

(ix) FEATURE:
         (A) NAME/KEY: Modified-site
         (B) LOCATION:group(2, 4, 7, 9, 10, 11, 13, 14, 16)
         (D) OTHER INFORMATION:/product= "D-amino acid residues"

(xi) SEQUENCE DESCRIPTION: SEQ ID NO: 69:

Arg Ile Tyr Val Lys Ile His Leu Arg Tyr Ile Lys Lys Ile Arg Leu
1               5                   10                  15

(2) INFORMATION FOR SEQ ID NO: 70:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: peptide 70

(ix) FEATURE:
         (A) NAME/KEY: Modified-site
```

(B) LOCATION:group(1, 3, 5, 8, 9, 11, 13, 14, 16)
            (D) OTHER INFORMATION:/product= "D-amino acid residues"

(xi) SEQUENCE DESCRIPTION: SEQ ID NO: 70:

Lys Ile Gly His Lys Ala Arg Val His Ile Ile Arg Tyr Lys Ile Ile
1               5                   10                  15

(2) INFORMATION FOR SEQ ID NO: 71:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 71

(ix) FEATURE:
        (A) NAME/KEY: Modified-site
        (B) LOCATION:group(2, 3, 4, 7, 8, 10, 11, 13, 14, 16)
        (D) OTHER INFORMATION:/product= "D-amino acid residues"

(xi) SEQUENCE DESCRIPTION: SEQ ID NO: 71:

Arg Ile Tyr Val Lys Pro His Pro Arg Tyr Ile Lys Lys Ile Arg Leu
1               5                   10                  15

(2) INFORMATION FOR SEQ ID NO: 72:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 72

(ix) FEATURE:
        (A) NAME/KEY: Modified-site
        (B) LOCATION:group(3, 5, 8, 9, 11, 13, 14, 16)
        (D) OTHER INFORMATION:/product= "D-amino acid residues"

(xi) SEQUENCE DESCRIPTION: SEQ ID NO: 72:

Lys Pro Gly His Lys Ala Arg Pro His Ile Ile Arg Tyr Lys Ile Ile
1               5                   10                  15

(2) INFORMATION FOR SEQ ID NO: 73:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 73

(ix) FEATURE:
        (A) NAME/KEY: Modified-site
        (B) LOCATION:group(2, 6, 7, 11, 15, 16, 18)
        (D) OTHER INFORMATION:/product= "D-amino acid residues"

(xi) SEQUENCE DESCRIPTION: SEQ ID NO: 73:

Lys Ile Val Ile Arg Ile Arg Ile Arg Leu Ile Arg Ile Arg Ile Arg
1               5                   10                  15

Lys Ile Val (2) INFORMATION FOR SEQ ID NO: 74:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 74

(ix) FEATURE:
        (A) NAME/KEY: Modified-site
        (B) LOCATION:group(2, 3, 4, 6, 7, 8, 10, 11, 13, 14, 16, 17,
            19)
        (D) OTHER INFORMATION:/product= "D-amino acid residues"

(xi) SEQUENCE DESCRIPTION: SEQ ID NO: 74:

Arg Ile Ile Val Lys Ile Arg Leu Arg Ile Ile Lys Lys Ile Arg Leu
1               5                   10                  15

Ile Lys Lys (2) INFORMATION FOR SEQ ID NO: 75:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 75

(ix) FEATURE:
        (A) NAME/KEY: Modified-site
        (B) LOCATION:group(3, 4, 5, 8, 9, 11, 13, 14, 16, 17, 18)
        (D) OTHER INFORMATION:/product= "D-amino acid residues"

(xi) SEQUENCE DESCRIPTION: SEQ ID NO: 75:

Lys Ile Gly Trp Lys Leu Arg Val Arg Ile Ile Arg Val Lys Ile Gly
1               5                   10                  15

Arg Leu Arg (2) INFORMATION FOR SEQ ID NO: 76:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 76

(ix) FEATURE:
        (A) NAME/KEY: Modified-site
        (B) LOCATION:group(2, 6, 7, 11, 15, 16, 18, 20, 24, 25)
        (D) OTHER INFORMATION:/product= "D-amino acid residues"

(xi) SEQUENCE DESCRIPTION: SEQ ID NO: 76:

Lys Ile Val Ile Arg Ile Arg Ile Arg Leu Ile Arg Ile Arg Ile Arg
1               5                   10                  15

```
Lys Ile Val Lys Val Lys Arg Ile Arg
            20                  25
```

(2) INFORMATION FOR SEQ ID NO: 77:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 77

(ix) FEATURE:
        (A) NAME/KEY: Modified-site
        (B) LOCATION:group(2, 3, 4, 6, 7, 8, 10, 11, 13, 14, 16, 17,
            19..22, 24, 25)
        (D) OTHER INFORMATION:/product= "D-amino acid residues"

(xi) SEQUENCE DESCRIPTION: SEQ ID NO: 77:

```
Arg Phe Ala Val Lys Ile Arg Leu Arg Ile Ile Lys Lys Ile Arg Leu
1               5                  10                  15

Ile Lys Lys Ile Arg Lys Arg Val Ile Lys
            20                  25
```

(2) INFORMATION FOR SEQ ID NO: 78:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 78

(ix) FEATURE:
        (A) NAME/KEY: Modified-site
        (B) LOCATION:group(3, 4, 5, 8, 9, 11, 13, 14, 16, 17, 18, 22,
            23, 24, 27, 28, 30)
        (D) OTHER INFORMATION:/product= "D-amino acid residues"

(xi) SEQUENCE DESCRIPTION: SEQ ID NO: 78:

```
Lys Ala Gly Trp Lys Leu Arg Val Arg Ile Ile Arg Val Lys Ile Gly
1               5                  10                  15

Arg Leu Arg Lys Ile Gly Trp Lys Lys Arg Val Arg Ile Lys
            20                  25                  30
```

(2) INFORMATION FOR SEQ ID NO: 79:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 79

(ix) FEATURE:
        (A) NAME/KEY: Modified-site
        (B) LOCATION:group(2..5, 7, 8, 10, 11, 13, 14, 16)
        (D) OTHER INFORMATION:/product= "D-amino acid residues"

(xi) SEQUENCE DESCRIPTION: SEQ ID NO: 79:

Arg Ile Tyr Val Lys Pro His Pro Arg Tyr Ile Lys Lys Ile Arg Leu
1               5                  10                  15

(2) INFORMATION FOR SEQ ID NO: 80:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 80

(ix) FEATURE:
        (A) NAME/KEY: Modified-site
        (B) LOCATION:group(1, 2, 3, 5, 7..11, 13, 14, 16)
        (D) OTHER INFORMATION:/product= "D-amino acid residues"

(xi) SEQUENCE DESCRIPTION: SEQ ID NO: 80:

Lys Pro Gly His Lys Ala Arg Pro His Ile Ile Arg Tyr Lys Ile Ile
1               5                  10                  15

(2) INFORMATION FOR SEQ ID NO: 81:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 81

(ix) FEATURE:
        (A) NAME/KEY: Modified-site
        (B) LOCATION:group(2, 4..8, 10..13, 15, 16, 18)
        (D) OTHER INFORMATION:/product= "D-amino acid residues"

(xi) SEQUENCE DESCRIPTION: SEQ ID NO: 81:

Lys Ile Val Ile Arg Ile Arg Ile Arg Leu Ile Arg Ile Arg Ile Arg
1               5                  10                  15

Lys Ile Val (2) INFORMATION FOR SEQ ID NO: 82:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 82

(ix) FEATURE:
        (A) NAME/KEY: Modified-site
        (B) LOCATION:group(2, 3, 4, 6..11, 13, 14, 16, 17, 19)
        (D) OTHER INFORMATION:/product= "D-amino acid residues"

(xi) SEQUENCE DESCRIPTION: SEQ ID NO: 82:

Arg Ile Ile Val Lys Ile Arg Leu Arg Ile Ile Lys Lys Ile Arg Leu
1               5                  10                  15

Ile Lys Lys (2) INFORMATION FOR SEQ ID NO: 83:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 83

(ix) FEATURE:
        (A) NAME/KEY: Modified-site
        (B) LOCATION:group(2..5, 7, 8, 10, 11, 13, 14, 16)
        (D) OTHER INFORMATION:/product= "D-amino acid residues"

(xi) SEQUENCE DESCRIPTION: SEQ ID NO: 83:

```
Arg Ile Tyr Val Ser Lys Ile Ser Ile Tyr Ile Lys Lys Ile Arg Leu
1               5                   10                  15
```

(2) INFORMATION FOR SEQ ID NO: 84:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 84

(ix) FEATURE:
        (A) NAME/KEY: Modified-site
        (B) LOCATION:group(2, 4..8, 10..13, 15, 16, 18)
        (D) OTHER INFORMATION:/product= "D-amino acid residues"

(xi) SEQUENCE DESCRIPTION: SEQ ID NO: 84:

```
Lys Ile Val Ile Phe Thr Arg Ile Arg Leu Thr Ser Ile Arg Ile Arg
1               5                   10                  15

Ser Ile Val
```

(2) INFORMATION FOR SEQ ID NO: 85:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide 85

(ix) FEATURE:
        (A) NAME/KEY: Modified-site
        (B) LOCATION:group(1, 2, 3, 5, 7..11, 13, 14, 16)

(xi) SEQUENCE DESCRIPTION: SEQ ID NO: 85:

```
Lys Pro Ile His Lys Ala Arg Pro Thr Ile Ile Arg Tyr Lys Met Ile
1               5                   10                  15
```

(2) INFORMATION FOR SEQ ID NO: 86:

(i) SEQUENCE CHARACTERISTICS:

(A) LENGTH: 25 amino acids
            (B) TYPE: amino acid
            (C) STRANDEDNESS: single
            (D) TOPOLOGY: circular (ii) MOLECULE TYPE: peptide (vii) IMMEDIATE SOURCE:
            (B) CLONE: peptide 86

(ix) FEATURE:
            (A) NAME/KEY: Modified-site
            (B) LOCATION:group(9, 20, 21)
            (D) OTHER INFORMATION:/product= "D-amino acid residues"

(ix) FEATURE:
            (D) OTHER INFORMATION:/product= "OTHER"
                  /note= "the N-terminal Cys forms a disulfide bond with
                  the C-terminal Cys"

(xi) SEQUENCE DESCRIPTION: SEQ ID NO: 86:

Cys Lys Gly Phe Phe Ala Leu Ile Pro Lys Ile Ile Ser Ser Pro Leu
1               5                   10                  15

Phe Lys Thr Leu Leu Ser Ala Val Cys
            20                  25

(2) INFORMATION FOR SEQ ID NO: 87:

(i) SEQUENCE CHARACTERISTICS:
            (A) LENGTH: 26 amino acids
            (B) TYPE: amino acid
            (C) STRANDEDNESS: single
            (D) TOPOLOGY: circular (ii) MOLECULE TYPE: peptide (vii) IMMEDIATE SOURCE:
            (B) CLONE: peptide 87

(ix) FEATURE:
            (A) NAME/KEY: Modified-site
            (B) LOCATION:group(10, 21, 22)
            (D) OTHER INFORMATION:/product= "D-amino acid residues"

(ix) FEATURE:
            (D) OTHER INFORMATION:/product= "OTHER"
                  /note= "the N-terminal Cys forms a disulfide bond with
                  the C-terminal Cys"

(xi) SEQUENCE DESCRIPTION: SEQ ID NO: 87:

Cys Lys Lys Gly Phe Phe Ala Leu Ile Pro Lys Ile Ile Ser Ser Pro
1               5                   10                  15

Leu Phe Lys Thr Leu Leu Ser Ala Val Cys
            20                  25

(2) INFORMATION FOR SEQ ID NO: 88:

(i) SEQUENCE CHARACTERISTICS:
            (A) LENGTH: 27 amino acids
            (B) TYPE: amino acid
            (C) STRANDEDNESS: single
            (D) TOPOLOGY: circular (ii) MOLECULE TYPE: peptide (vii) IMMEDIATE SOURCE:
            (B) CLONE: peptide 88

(ix) FEATURE:
            (A) NAME/KEY: Modified-site
            (B) LOCATION:group(11, 22, 23)
            (D) OTHER INFORMATION:/product= "D-amino acid residues"

(ix) FEATURE:
        (D) OTHER INFORMATION:/product= "OTHER"
            /note= "the N-terminal Cys forms a disulfide bond with
            the C-terminal Cys"

(xi) SEQUENCE DESCRIPTION: SEQ ID NO: 88:

Cys Lys Lys Lys Gly Phe Phe Ala Leu Ile Pro Lys Ile Ile Ser Ser
1               5                   10                  15

Pro Leu Phe Lys Thr Leu Leu Ser Ala Val Cys
            20                  25

(2) INFORMATION FOR SEQ ID NO: 89:

(i) SEQUENCE CHARACTERISTICS:
        (A) LENGTH: 16 amino acids
        (B) TYPE: amino acid
        (C) STRANDEDNESS: single
        (D) TOPOLOGY: circular (ii) MOLECULE TYPE: peptide (vii) IMMEDIATE SOURCE:
        (B) CLONE: peptide 89

(ix) FEATURE:
        (A) NAME/KEY: Modified-site
        (B) LOCATION:group(3, 7, 9, 12, 14)
        (D) OTHER INFORMATION:/product= "D-amino acid residues"

(ix) FEATURE:
        (D) OTHER INFORMATION:/product= "OTHER"
            /note= "the N-terminal Cys forms a disulfide bond with
            the C-terminal Cys"

(xi) SEQUENCE DESCRIPTION: SEQ ID NO: 89:

Cys Arg Ile Val Ile Arg Ile Arg Ile Arg Leu Ile Arg Ile Arg Cys
1               5                   10                  15

(2) INFORMATION FOR SEQ ID NO: 90:

(i) SEQUENCE CHARACTERISTICS:
        (A) LENGTH: 18 amino acids
        (B) TYPE: amino acid
        (C) STRANDEDNESS: single
        (D) TOPOLOGY: circular (ii) MOLECULE TYPE: peptide (vii) IMMEDIATE SOURCE:
        (B) CLONE: peptide 90

(ix) FEATURE:
        (A) NAME/KEY: Modified-site
        (B) LOCATION:group(2, 3, 4, 6, 8..12, 14, 15, 17)
        (D) OTHER INFORMATION:/product= "D-amino acid recidues"

(ix) FEATURE:
        (D) OTHER INFORMATION:/product= "OTHER"
            /note= "the N-terminal Cys forms a disulfide bond with
            the C-terminal Cys"

(xi) SEQUENCE DESCRIPTION: SEQ ID NO: 90:

Cys Lys Pro Gly His Lys Ala Arg Pro His Ile Ile Arg Tyr Lys Ile
1               5                   10                  15

Ile Cys (2) INFORMATION FOR SEQ ID NO: 91:

(i) SEQUENCE CHARACTERISTICS:
        (A) LENGTH: 28 amino acids
        (B) TYPE: amino acid

```
            (C) STRANDEDNESS: single
            (D) TOPOLOGY: circular (ii) MOLECULE TYPE: peptide (vii) IMMEDIATE SOURCE:
            (B) CLONE: peptide 91

(ix) FEATURE:
            (A) NAME/KEY: Modified-site
            (B) LOCATION:group(3, 4, 5, 7, 8, 9, 11, 12, 14, 15, 17, 18,
                20..23, 25, 26)
            (D) OTHER INFORMATION:/product= "D-amino acid residues"

(ix) FEATURE:
            (D) OTHER INFORMATION:/product= "OTHER"
                /note= "the N-terminal Cys forms a disulfide bond with
                the C-terminal Cys"

(xi) SEQUENCE DESCRIPTION: SEQ ID NO: 91:

Cys Arg Phe Ala Val Lys Ile Arg Leu Arg Ile Ile Lys Lys Ile Arg
1               5                   10                  15

Leu Ile Lys Lys Ile Arg Lys Arg Val Ile Lys Cys
            20                  25

(2) INFORMATION FOR SEQ ID NO: 92:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 92

(ix) FEATURE:
            (A) NAME/KEY: Modified-site
            (B) LOCATION:group(4, 5, 9, 11)
            (D) OTHER INFORMATION:/product= "D-amino acid residues"

(ix) FEATURE:
            (D) OTHER INFORMATION:/product= "OTHER"
                /note= "the N-terminal Cys forms a disulfide bond with
                the C-terminal Cys"

(xi) SEQUENCE DESCRIPTION: SEQ ID NO: 92:

Cys Lys Leu Leu Leu Lys Leu Leu Leu Lys Leu Leu Lys Cys
1               5                   10

(2) INFORMATION FOR SEQ ID NO: 93:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 93

(ix) FEATURE:
            (A) NAME/KEY: Modified-site
            (B) LOCATION:group(4, 5, 9, 11)
            (D) OTHER INFORMATION:/product= "D-amino acid residues"

(ix) FEATURE:
            (D) OTHER INFORMATION:/product= "OTHER"
                /note= "the N-terminal Cys forms a disulfide bond with
                the C-terminal Cys"
```

(xi) SEQUENCE DESCRIPTION: SEQ ID NO: 93:

Cys Lys Leu Leu Leu Lys Leu Lys Leu Lys Leu Leu Lys Cys
1               5                   10

(2) INFORMATION FOR SEQ ID NO: 94:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 94

(ix) FEATURE:
            (A) NAME/KEY: Modified-site
            (B) LOCATION:group(3, 4, 8, 10)
            (D) OTHER INFORMATION:/product= "D-amino acid residues"

(ix) FEATURE:
            (D) OTHER INFORMATION:/product= "OTHER"
                /note= "cyclic peptide"

(xi) SEQUENCE DESCRIPTION: SEQ ID NO: 94:

Lys Leu Leu Leu Lys Leu Leu Leu Lys Leu Leu Lys
1               5                   10

(2) INFORMATION FOR SEQ ID NO: 95:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 95

(ix) FEATURE:
            (A) NAME/KEY: Modified-site
            (B) LOCATION:group(3, 4, 8, 10)
            (D) OTHER INFORMATION:/product= "D-amino acid residues"

(ix) FEATURE:
            (D) OTHER INFORMATION:/product= "cyclic pepetide"

(xi) SEQUENCE DESCRIPTION: SEQ ID NO: 95:

Lys Leu Leu Leu Lys Leu Lys Leu Lys Leu Leu Lys
1               5                   10

(2) INFORMATION FOR SEQ ID NO: 96:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (B) CLONE: peptide 96 (monomer peptide 23C)

(ix) FEATURE:
            (A) NAME/KEY: Modified-site
            (B) LOCATION:group(3, 4, 8, 10)
            (D) OTHER INFORMATION:/product= "D-amino acid residues"

```
    (ix) FEATURE:
         (A) NAME/KEY: Modified-site
         (B) LOCATION:13
         (D) OTHER INFORMATION:/product= "OTHER"
             /note= "the carboxyl group at the C-terminus is replaced
             by an amino group"

(xi) SEQUENCE DESCRIPTION: SEQ ID NO: 96:

Lys Leu Leu Leu Lys Leu Leu Leu Lys Leu Leu Lys Cys
1               5                   10

(2) INFORMATION FOR SEQ ID NO: 97:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: peptide 97 (monomer peptide 24C)

(ix) FEATURE:
         (A) NAME/KEY: Modified-site
         (B) LOCATION:group(3, 4, 8, 10)
         (D) OTHER INFORMATION:/product= "D-amino acid residues"

(ix) FEATURE:
         (A) NAME/KEY: Modified-site
         (B) LOCATION:13
         (D) OTHER INFORMATION:/product= "OTHER"
             /note= "the carboxyl group at the C-terminus is replaced
             by an amino group"

(xi) SEQUENCE DESCRIPTION: SEQ ID NO: 97:

Lys Leu Leu Leu Lys Leu Lys Leu Lys Leu Leu Lys Cys
1               5                   10

(2) INFORMATION FOR SEQ ID NO: 98:

(i) SEQUENCE CHARACTERISTICS:
         (A) LENGTH: 33 amino acids
         (B) TYPE: amino acid
         (C) STRANDEDNESS: single
         (D) TOPOLOGY: linear (ii) MOLECULE TYPE: peptide (vii) IMMEDIATE SOURCE:
         (B) CLONE: PARDAXIN (xi) SEQUENCE DESCRIPTION: SEQ ID NO: 98:

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu (2) INFORMATION FOR SEQ ID NO: 99:

(i) SEQUENCE CHARACTERISTICS:
         (A) LENGTH: 26 amino acids
         (B) TYPE: amino acid
         (C) STRANDEDNESS: single
         (D) TOPOLOGY: linear (ii) MOLECULE TYPE: peptide
```

-continued

```
    (vii) IMMEDIATE SOURCE:
          (B) CLONE: Melittin (ix) FEATURE:
         (A) NAME/KEY: Modified-site
         (B) LOCATION:26
         (D) OTHER INFORMATION:/product= "OTHER"
             /note= "the carboxyl group at the C-terminus is replaced
             by an amino group"

(xi) SEQUENCE DESCRIPTION: SEQ ID NO: 99:

Gly Ile Gly Ala Val Leu Lys Val Leu Thr Thr Gly Leu Pro Ala Leu
1               5                  10                 15

Ile Ser Trp Ile Lys Arg Lys Arg Gln Gln
            20                  25
```

ANTIPATHOGENIC SYNTHETIC PEPTIDES AND COMPOSITIONS COMPRISING THEM

CROSS REFERENCE TO RELATED APPLICATION

The present application is the national stage under 35 U.S.C. 371 of PCT/IL98/00081, filed Feb. 19, 1998 which claims priority to application PCT/IL97/00066, FILED Feb. 20, 1997.

FIELD OF THE INVENTION

The present invention concerns novel non-hemolytic cytolytic agents, compositions comprising them and their use in the treatment of diseases or disorders and in agriculture.

BACKGROUND OF THE INVENTION

In the text below, reference is being made to prior art documents, the complete particulars of which can be found in the "References" section at the end of the specification before the claims.

The increasing resistance of microorganisms to the available antimicrobial drugs has resulted in extensive studies focused on developing alternative antimicrobial compounds.

In addition, or complementary, to the highly specific cell-mediated immune response, vertebrates and other organisms have a defense system made up of distinct groups of broad spectrum cytolytic, e.g., antibacterial, peptides.

Studies on lipid-peptide interactions of such cytolytic peptides, also known as cytolysins, tend to emphasize the importance of the amphipathic α-helical structure for their cytolytic activity. This conclusion is based mainly on studies with cytolysins that act on either mammalian cells or bacteria alone or on both types of cells. A major group of cytolytic peptides in this family are host-defense short linear peptides ($\leq 40$ amino acids), which are devoid of disulfide bridges (Boman, 1995). The peptides vary considerably in chain length, hydrophobicity and overall distribution of charges, but share a common structure upon association with lipid bilayers, namely, an amphipathic α-helix structure (Segrest et al., 1990).

Examples of known cytolysins include: (i) antibacterial peptides that are cytolytic to bacteria only, e.g. cecropins, isolated from the cecropia moth (Steiner et al., 1981), magainins (Zasloff, 1987) and dermaseptins (Mor et al., 1991) isolated from the skin of frogs; (ii) cytolysins that are selectively cytotoxic to mammalian cells, such as δ-hemolysin isolated from *Staphylococcus aureus* (Dhople and Nagaraj, 1993); and (iii) cytolysins that are not cell-selective, such as the bee venom melittin (Habermann and Jentsch, 1967) and the neurotoxin pardaxin (Shai et al., 1988) that lyse both mammalian cells and bacteria.

Antibacterial peptides were initially discovered in invertebrates, and subsequently in vertebrates, including humans. As a complementary or additional defense system, this secondary, chemical immune system provides organisms with a repertoire of small peptides that are synthesized promptly upon induction, and which act against invasion by occasional and obligate pathogens as well as against the uncontrolled proliferation of commensal microorganisms (Boman, 1995). So far, more than 100 different antibacterial peptides have been isolated and characterized. The largest family, and probably the most studied, includes those peptides that are positively charged and adopt an amphipathic α-helical structure. Numerous studies conducted on various native antibacterial peptides tend to emphasize the importance of an amphipathic α-helical structure and a net positive charge for cytolytic activity. The positive charge facilitates interaction of the peptides with the negatively-charged membranes (Andreu et al., 1985) found in higher concentrations in the pathogenic cell membrane as compared to normal eukaryotic cells, and the amphipathic α-helical structure is essential for lytic activity (Chen et al., 1998). Such interactions have been proposed to destroy the energy rhetabolism of the target organism by increasing the permeability of energy-transducing membranes (Okada and Natori, 1984). Because of their amphipathic structure, it has been suggested that these antibacterial peptides permeate the membrane by forming ion channels/pores via a "barrel-stave" mechanism (Rizzo et al., 1987). According to this model transmembrane amiphiphilic α-helices form bundles in which outwardly-directed hydrophobic surfaces interact with the lipid constituents of the membrane, while inwardly facing hydrophilic surfaces produce a pore. Alternatively, the peptides bind parallel to the surface of the membrane, cover the surface of the membrane in a "carpet"-like manner and dissolve it like a detergent (Shai, 1995).

Despite extensive studies, the exact mode of action of short linear non cell-selective peptides, such as pardaxin and melittin, is not known yet, and it is not clear whether similar structural features are required for their cytotoxicity towards mammalian cells and bacteria.

Pardaxin, a 33-mer peptide, is an excitatory neurotoxin that has been purified from the Red Sea Moses Sole *Pardachirus marmoratus* (Shai et al., 1988) and from the Peacock Sole of the western Pacific *Pardachirus pavoninus* (Thompson et al., 1986). Pardaxin possesses a variety of biological activities depending upon its concentration (reviewed in Shai, 1994). At concentrations below $10^{-7}$ M, pardaxin induces the release of neurotransmitters in a calcium-dependent manner. At higher concentrations of $10^{-7}$ M to $10^{-5}$ M, the process is calcium-independent, and above $10^{-5}$ M cytolysis is induced. Pardaxin also affects the activities of various physiological preparations in vitro. Its biological roles have been attributed to its interference with the ionic transport of the osmoregulatory system in epithelium and to presynaptic activity by forming ion channels that are voltage dependent and slightly selective to cations. A "barrel-stave" mechanism for insertion of pardaxin into membranes was proposed on the basis of its structure and various biophysical studies (reviewed in Shai, 1994). Pardaxin has a helix-hinge-helix structure: the N-helix includes residues 1–11 and the C-helix includes residues 14–26. The helices are separated by a proline residue situated at position 13. This structural motif is found both in antibacterial peptides that can act specifically on bacteria (e.g., cecropin), and in cytotoxic peptides that can lyse a variety of cells (e.g., melittin).

Melittin, a 26-mer amphipathic peptide, is the major component of the venom of the honey bee *Apis mellifera* (Habermann and Jentsch, 1967) and is one of the most studied membrane-seeking peptides (Dempsey, 1990). Melittin is highly cytotoxic for mammalian cells, but is also a highly potent antibacterial agent (Steiner et al., 981). Numerous studies have been undertaken to determine the nature of the interaction of melittin with membranes, both with the aim of understanding the molecular mechanism of melittin-induced hemolysis and as a model for studying the general features of structures of membrane proteins and interactions of such proteins with phospholipid membranes. Much of the currently described evidence indicates that different molecular mechanisms may underlie different actions of melittin. Nevertheless, the amphipathic α-helical structure has been shown to be a prerequisite for its various activities (Perez et al., 1994).

The structure of melittin has been investigated using various techniques. The results of X-ray crystallography and NMR in methanolic solutions indicate that the molecule consists of two α-helical segments (residues 1–10 and 13–26) that intersect at an angle of 120°. These segments are connected by a hinge (11–12) to form a bent α-helical rod with the hydrophilic and hydrophobic sides facing opposite directions. Four such monomeric melittin molecules cluster together, through hydrophobic interactions, to form a tetramer (Anderson et al., 1980; Bazzo et al., 1998; Terwilliger and Eisenberg, 1982; Terwilliger and Eisenberg, 1982). Upon initial interaction with membrane surfaces, it has been found that the tetramer dissociates to monomers, which retain α-helical conformation prior to insertion into the membrane (Altenbach and Hubbell, 1988).

Melittin shares some similarities with pardaxin. Both pardaxin and melittin are composed of two helices with a proline hinge between them. Furthermore, they exhibit significant homology in their N-helices, which are mostly hydrophobic (Thompson et al., 1986). However, pardaxin (net charge +1) contains an additional seven amino acids residue at its C-terminal side with a charge of −2, while melittin (net charge α6) terminates with an amide group and contains the positively-charged tetrapeptide sequence Lys-Arg-Lys-Arg. There are several functional differences between pardaxin and melittin. Pardaxin binds similarly to both zwitterionic and negatively charged phospholipids (Rapaport and Shai, 1991), while melittin binds better to negatively charged than to zwitterionic phospholipids (Batenburg et al., 1987; Batenburg et al., 1987). Also, pardaxin binds to phospholipids with positive cooperativity (Rapaport and Shai, 1991) while melittin binds with negative cooperativity (Batenburg et al., 1987; Batenburg et al., 1987). Although both pardaxin and melittin are potent antibacterial peptides against Gram-positive and Gram-negative bacteria, pardaxin is 40–100 fold less hemolytic than melittin towards human erythrocytes (Oren and Shai, 1996).

Analogues of pardaxin with L- to D-substitutions were shown to be capable of lysing human erythrocytes (Pouny and Shai, 1992). It was later shown (see results reported below) that two of the peptides disclosed in Pouny and Shai, 1992, namely, D-Pro[7]-pardaxin and D-Leu[18]Leu[19]-pardaxin, while being hemolytic, have a very low antibacterial activity. Analogues of magainin with L- to D-substitutions were also found to lack antibacterial activity (Chen et al., 1988).

GLOSSARY

In the following, use will be made of several coined terms for the purpose of streamlining reading of the text and facilitating better understanding of the invention. it should be noted, however, that for complete understanding of these terms, reference will at times be made to the complete description below. These terms and their meaning herein are the following:

"Heterogeneous peptide" as used herein refers to a peptide comprising both D- and L-amino acid residues.

"Homogeneous peptide" as used herein refers to a peptide comprising either only the natural L-amino acid residues, or only D-amino acid residues.

"Homogeneous L-peptide" and "homogeneous D-peptide" as used herein refers the homogeneous polypeptide consisting entirely of either L- or D-amino acid residues, respectively.

"Heterogeneous L-based peptide" and "heterogeneous D-based peptide" as used herein refers to a heterogeneous peptide comprising primarily L-amino acid residues, e.g., a peptide derived from homogeneous L-peptide in which one or more of the L-amino acid residues has been replaced by counterpart D-enantiomers, and a heterogeneous peptide comprising primarily D-amino acid residues in which one or more of the D-amino acid residues has been replaced by counterpart L-enantiomers, respectively.

"Helical peptide" as used herein refers to a peptide having a continuous α-helix stretch throughout the major portion of its length. The helical portion of a helical peptide consists entirely of either L-amino acid residues or D-amino acid residues.

"Non-helical peptide" as used herein refers to a peptide which has no α-helix structure or has non-continuous α-helix structures dispersed along its length. A non-helical peptide according to the invention may have an α-helix stretch which, in case it is terminal, has a length spanning less than half a width of a cell's membrane, e.g., less than about 10–15 amino acid residues, and if it is a non-terminal α-helix, has a length which is less than the full width of the cell's membrane, e.g., less than about 20–25 amino acid residues. A non-helical peptide may be a homogeneous peptide with α-helix breaker moieties (see below) or may be a heterogeneous peptide.

"α-helix breaker moiety" as used herein refers to a moiety which if inserted into an α-helix structure disrupts its continuity. Such a moiety may for example be the amino acid residue proline or glycine, α-methyl-substituted α-amino acids, non-α-amino acids both cyclic and acyclic such as 6-amino-hexanoic acid, 3-amino-1-cyclohexanoic acid, 4-amino-1-cyclohexanoic acid or may be an L- or D-enantiomer inserted into an α-helix stretch consisting of a stretch of amino acid residues of the opposite enantiomer.

"Pathogenic cells" as used herein refers to cells which are non-naturally occurring within the body, including cancer cells and pathogenic organisms such as bacteria, fungi, protozoa, virus and mycoplasma, as well as mammalian cells infected with pathogenic organisms such as parasitic protozoans, e.g Leishmania and Plasmodium.

"Selective cytolytic activity" as used herein refers to activity of an agent in inducing cytolysis of a pathogenic cell, the selectivity being manifested in that the agent induces cytolysis of the pathogenic cells at a much lower concentration to that required for the cytolysis of normal non-pathogenic cells such as red blood cells.

"Non-hemolytic" as used herein refers to agents which cause hemolysis of red blood cells at much higher concentrations than the concentration required to cause cytolysis of other cells, such as pathogenic cells such as microorganism cells, cancer cells, and the like.

"Diastereomers" is used herein as a synonym of "heterogeneous peptide".

SUMMARY OF THE INVENTION

The present invention provides a non-hemolytic cytolytic agent selected from a peptide, a complex of bundled peptides, a mixture of peptides or a random peptide copolymer, said agent having a selective cytolytic activity manifested in that it has a cytolytic activity on pathogenic cells; being cells which are non-naturally occurring within the body consisting of microbial pathogenic organisms and malignant cells; and it is non-hemolytic, namely it has no cytolytic effect on red blood cells or has a cytolytic effect on red blood cells at concentrations which are substantially higher than that in which it manifests said cytolytic activity, said non-hemolytic cytolytic agent being selected from the group consisting of:

(1) a cyclic derivative of a peptide having a net positive charge which is greater than +1, and comprising both L-amino acid residues and D-amino acid residues, or comprising one or both of L-amino acid residues and D-amino acid residues, and comprising an α-helix breaker moiety;

(2) a peptide comprising both L-amino acid residues and D-amino acid residues, having a net positive charge which is greater than +1, and having a sequence of amino acids such that a corresponding amino acid sequence comprising only L-amino acid residues is not found in nature, and cyclic derivatives thereof;

(3) a complex consisting of a plurality of 2 or more non-hemolytic cytolytic peptides, each peptide having a net positive charge which is greater than +1, and comprising both L-amino acid residues and D-amino acid residues, or comprising one or both of L-amino acid residues and D-amino acid residues and comprising an α-helix breaker moiety, or cyclic derivatives of the foregoing, said peptides being bundled together by the use of a linker molecule covalently bound to each of the peptides;

(4) a mixture consisting of a plurality of 2 or more non-hemolytic cytolytic peptides, each peptide having a net positive charge which is greater than +1, and comprising both L-amino acid residues and D-amino acid residues, or comprising one or both of L-amino acid residues and D-amino acid residues and comprising an α-helix breaker moiety, or cyclic derivatives of the foregoing; and (5) a random copolymer consisting of different ratios of a hydrophobic, a positively charged and a D-amino acid.

In one embodiment, the cyclic derivatives of (1) above are derived from a non-selective cytolytic natural peptide such as for example pardaxin and mellitin or from a fragment thereof. These cyclic diastereomers are obtained by conventional cyclization methods for peptides. In one embodiment, the cyclic diastereomer is derived from the fragment 1–22 of pardaxin to which 1 to 3 Lys residues have been added to the N-terminus and cysteine residues have been added to both N- and C-terminus for cyclization.

The net positive charge of the peptides may be due to the native amino acid composition, to neutralization of free carboxyl groups, and/or to the addition of positively charged amino acid residues or positively charged chemical groups.

In another embodiment, the invention provides a non-hemolytic cytolytic peptide and cyclic derivatives thereof as defined in (2) above, having the following characteristics:

(a) it is a non-natural synthetic peptide composed of varying ratios of at least one hydrophobic amino acid and at least one positively charged amino acid, and in which sequence at least one of the amino acid residues is a D-amino acid;

(b) the peptide has a net positive charge which is greater than +1; and (c) the ratio of hydrophobic to positively charged amino acids is such that the peptide is cytolytic to pathogenic cells but does not cause cytolysis of red blood cells.

Examples of positively charged amino acids are lysine, arginine and histidine, and of hydrophobic amino acids are leucine, isoleucine, glycine, alanine, valine, phenylalanine, proline, tyrosine and tryptophan. The net positive charge is due to the amino acid composition, but the addition of positively charged chemical groups may also be considered. In addition, polar amino acids such as serine, threonine, methionine, asparagine, glutamine and cysteine, may be added in order to decrease the hydrophobicity and/or the toxicity of the molecule. In one preferred embodiment, the peptide is composed of one hydrophobic amino acid such as leucine, alanine or valine, and one positively charged amino acid such as lysine or arginine. The synthetic non-natural peptide may have at least 6, particularly ten or more amino amino acid residues. In one preferred embodiment, the synthetic diastereomer is a 12-mer peptide composed of leucine, alanine or valine and lysine, and at least one third of the sequence is composed of D-amino acids.

In still another embodiment, the invention provides a non-hemolytic cytolytic complex as defined in (3) above, consisting of a plurality of 2 or more non-hemolytic cytolytic peptides complexed or "bundled" together, e.g. by the use of a linker or "template" molecule covalently bound to each of the peptides. The bundle may be composed of 2 or more, preferably 5, molecules of the same peptide or of different peptides. The linker/template may be a peptide or a commonly used linker, e.g. polymers such as polyesters, polyamides, polypeptides, polyaminoacids (e.g. polylysine) carrying active groups such as OH, SH, COOH, $NH_2$, $CH_2Br$.

In still a further embodiment, the invention provides a non-hemolytic cytolytic mixture as defined in (4) above, obtained by adding a mixture composed of 1 eq each of the desired hydrophobic, positively charged and D-amino acid at each coupling step of the solid phase method for peptide synthesis. In this way, a mixture of $3^{12}$ different peptides were obtained with a mixture of lysine, leucine and D-leucine, and the mixture was obtained therefrom after HF cleavage, extraction with water and lyophilization.

In a further embodiment, the invention provides a non-hemolytic cytolytic random copolymer as defined in (5) above consisting of different ratios of a hydrophobic, a positively charged and a D-amino acid, e.g. 1:1:1, 2:1:1 and 3:1:1 (Mol) copolymers of Lys:Leu:D-Leu.

Preferably, the non-hemolytic cytolytic peptide has either no α-helix structure or has an α-helix structure which length is insufficient to span the width of a cell membrane. The peptide thus does not contain an uninterrupted stretch of either all D- or all L-amino acid residues of a length capable of forming part of a transmembrane pore. Such a length is typically about 20–22 amino acids, where the stretch is in the non-terminal portion of the peptide and about half, i.e., 10–11 amino acids, where the stretch is in the terminus of the peptides, since in such a case two peptides may join their terminus together and span the cell's membrane.

The disruption of a stretch of D- or L-amino acids residues may be carried out by replacement of one or more amino acids in the stretch by the amino acid of the opposite enantiomer or by placing in the continuous stretch an α-helix breaker moiety such as proline, glycine, an α-methyl-α-amino acid or a non-α-amino acid.

The peptides of the invention and the peptides comprised within the complexes, mixtures and copolymers of the invention have a net positive charge greater than +1. The net positive charge may be due to the native amino acid composition of the invention, to neutralization of free COOH groups, for example by amidation, or may be due to addition of positively charged amino acids or chemical groups. It was found that the selective cytolytic activity can at times be enhanced by increasing the net positive charge, for example, by attaching at any position in the molecule a positively charged amino acid and/or a positively charged group. For example, a polyamine group, an alkylamino group or amino alkylamino group, etc., may be attached at one of its terminals, typically at its carboxyl terminal. A preferred such group is the aminoethylamino group —NH—CH$_2$—CH$_2$—NH$_2$, designated hereinafter "TA".

The peptides that are derived from non-selective cytolytic natural peptides, e.g. pardaxin and melittin, are amphipathic, meaning that they have one surface which is mainly composed of hydrophobic amino acid residues and an opposite surface which is mainly composed of hydrophilic amino acid residues. The amphipathic nature of peptides may be verified according to methods known in the art. An example of such a method is the use of a Shiffer and Edmondson wheel projection wherein the amino acid residues are written, according to their sequence in a circle so that each amino acid in the sequence is angularly displaced by 100° from its neighboring amino acid residues (3.6 amino acids per circle). If most hydrophilic amino acids concentrate on one side of the wheel and hydrophobic amino acids concentrate on the opposite side of the wheel then the peptide may be considered amphipathic.

The peptides of the invention that are not derived from non-selective cytolytic natural peptides, e.g. the synthetic diastereomers composed of hydrophobic, positively charged and D-amino acids, are not amphipathic. They have a net positive charge greater than +1 and a suitable hydrophobic to positively charged amino acid ratio such that the resulting peptide is cytolytic to pathogenic cells but not hemolytic. These peptides can be screened very easily according to the invention by using the antibacterial and hemolytic tests described herein. In one embodiment, for a peptide composed of leucine and lysine, an appropriate Leu:Lys ratio may be 64%:36% for a diastereomer of 6 amino acid residues, and 66%:34% for a diastereomer of 12 amino acid residues.

Without wishing to be bound by theory, it is believed however that the cytolytic activity may be the result of aggregation of a number of peptides on the surface of the membrane and together such peptides cause lesion of the cell membrane. Accordingly, as described above, it is contemplated in accordance with the invention also to use a plurality of peptides either as a mixture or complexed (or bundled) together, e.g., by the use of a linker molecule covalently bound to each of the peptides.

The individual peptide typically consists of at least six, and preferably ten or more amino acid residues. In a complex of the invention, each individual peptide may typically have a length of above 5 amino acid residues.

The present invention also provides a pharmaceutical composition comprising a non-hemolytic cytolytic agent of the invention as the active ingredient, and a pharmaceutically acceptable carrier. The compositions are for use in the treatment of diseases or disorders caused by different pathogenic organisms such as Gram-positive and Gram-negative bacteria, virus, fungi, mycoplasma, and parasitic protozoa, e.g Leishmania that causes leishmaniasis and Plasmodium that causes malaria. In a preferred embodiment, the antipathogenic composition is an antimicrobial, particularly antibacterial compositions. In addition, the compositions of the invention are useful against malignant cells and can be used in the treatment of cancer.

Also provided by the present invention is a method of treatment comprising administering said hemolytic non-cytolytic agent to a subject in need. The method of the invention as well as the above composition are applicable in both human and veterinary medicine.

Further provided in accordance with the invention is also the use of said non-hemolytic cytolytic agent in the preparation of a pharmaceutical composition for the treatment of a disease or a disorder in human or a non-human animal, in particular antibacterial compositions.

In a further embodiment, the selective agents of the invention can be used as disinfectants for the destruction of microorganisms, i.e., in solution for wetting contact lenses, may be used as preservatives, for example in the cosmetic or food industry, and as pesticides, e.g. fungicides, bactericides, in agriculture, or for preservation of agricultural products, e.g. fruits and legumes.

BRIEF DESCRIPTION OF THE DRAWINGS

FIG. 14A, control; FIG. 14B, *E. coli* treated with [D]-L$^{3,4,8,10}$-K$_3$L$_9$; FIG. 14C, *E. coli* treated with [D]-L$^{3,4,8,10}$-K$_4$L$_8$; FIG. 14D, *E. coli* treated with [D]-L$^{3,4,8,10}$-K$_5$L$_7$; FIG. 14E, *E. coli* treated with [D]-L$^{3,4,8,10}$-K$_7$L$_5$; FIG. 14F, control; FIG. 14G, *E. coli* treated with [D]-L$^{3,4,8,10}$-K$_4$L$_8$; FIG. 14H, *E. coli* treated with [D]-L$^{3,4,8,10}$-K$_5$L$_7$.

DETAILED DESCRIPTION OF THE INVENTION

Figure 1:
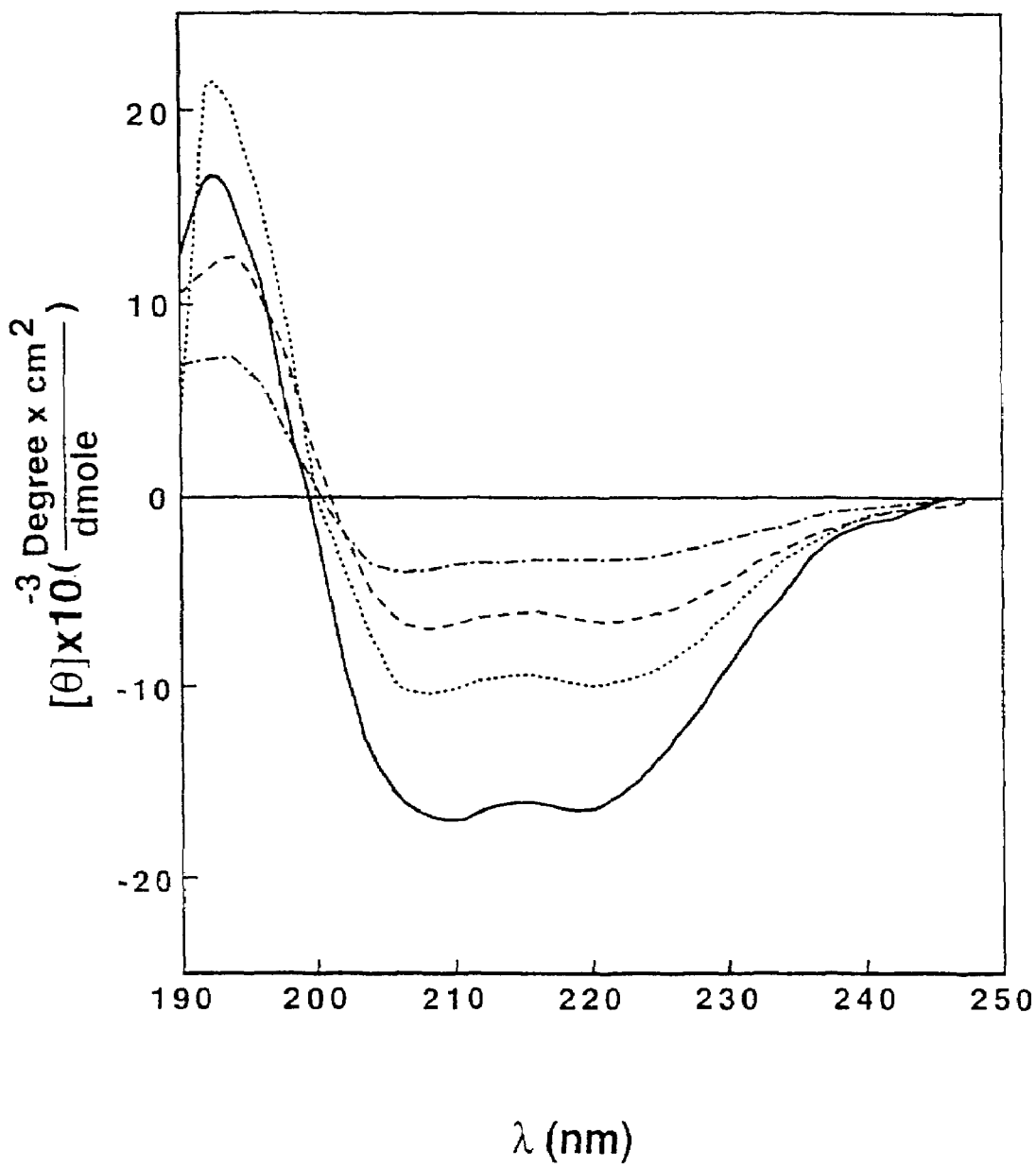
FIG. 1 shows circular dichroism (CD) spectra of aminoethylaminopardaxin (TApar)-derived peptides. Spectra were taken at peptide concentrations of $0.8–2.0 \times 10^{-5}$ M in 40% 2,2,2-trifluoroethanol (TFE)/water. Symbols: TApar (–); [D]P$^7$-TApar (.....); [D]L$^{18}$L$^{19}$-TApar (–) and [D]P$^7$L$^{18}$L$^{19}$-TApar (—·—)

Heterogeneous L-based peptides have been found by the present inventors to possess selective cytolytic activity manifested by a selective destruction of pathogenic cells, e.g., bacteria, with little or no effect on non-pathogenic cells, i.e., red blood cells. This finding is very surprising in view of the prevalent belief in the art that the cytolytic activity of cytolytic peptides in cells, whether pathogenic cells such as bacteria or normal mammalian cells, arises from a single underlying mechanism associated with the α-helix configuration.

Functional and structural studies with D-amino acid incorporated analogues (diastereomers) of pardaxin and melittin, two known non-cell selective cytolysins, carried in order to understand the molecular mechanism underlying cell selectively, revealed that the resulting diastereomers did not retain their α-helical structure, which caused abrogation of their cytotoxic effects on mammalian cells. However, the diastereomers retained a high antibacterial activity, which was expressed by complete lysis of both Gram-positive and Gram-negative bacteria. Thus, the α-helical structure of pardaxin and melittin was shown to be important for cytotoxicity against mammalian cells, but not to be a prerequisite for antibacterial activity. However, in another study, a single D-amino acid incorporated into the non-hemolytic antibacterial peptide magainin abolished almost totally its antibacterial activity (Chen et al., 1988). The results with pardaxin and melittin diastereomers suggest that hydrophobicity and a net positive charge confer selective antibacterial activity to non-selective cytolytic peptides and that amphipathic α-helical structure is not required. However, the diastereomers of pardaxin and melittin contained long stretches of L-amino acids (14–17 aa long) which raises the possibility that the low residual helicity could be sufficient for membrane binding and destabilization.

To examine whether modulating hydrophobicity and the net positive charge of linear cytotoxic peptides is sufficient to confer selective antibacterial activity, we chose to investigate diastereomers of short model peptides (12 aa. long), composed of varying ratios of leucine and lysine and one third of their sequence composed of D-amino acids. Peptide length and the position of D-amino acids were such that short peptides with very short consecutive stretches of 1–3 L-amino acids that cannot form an α-helical structure were constructed. The diastereomers were evaluated with regard to (1) their cytotoxicity against bacteria and human erythrocytes, (2) their structure, and (3) their ability to interact and perturb the morphology of the bacterial wall and model phospholipid membranes. The data show that modulating hydrophobicity and positive charge is sufficient to confer antibacterial activity and cytolytic selectivity. Furthermore, the resulting antibacterial peptides act synergistically at non lethal concentrations with available antibacterial drugs such as tetracycline, and they are totally resistant to human serum inactivation which dramatically reduces the activity of native antibacterial peptides. Further shorter diastereomers (66 aa and 8 aa long) were prepared and tested and found to be non-hemolytic cytolytic.

The finding that certain cytolytic non-helical peptides have an anti-pathogenic activity, paves the way for the preparation of anti-pathogenic agents, which comprise such non-helical polypeptides. Where the non-helical peptides are heterogeneous peptides composed of both L-amino acids and D-amino acids, the anti-pathogenic agents have the additional advantage of being more resistant to degradation, for example by proteases, than homologous L-peptides, on the one hand, and on the other hand, are not completely degradation-resistant as the full homologous D-peptides. Resistance to degradation may be disadvantageous in view of slow clearance from the body with possible associated toxic side effects. The non-α-helical antipathogenic peptides may be used in a variety of therapeutic procedures.

Since it is known that homologous D-peptides possess essentially identical cytolytic activity to the corresponding homologous L-peptides (Bessalle et al., 1990) then accordingly it is clear that heterogeneous D-based peptides possess the same antipathogenic properties as heterogeneous L-based peptides.

The finding that certain non-α-helical peptides have a cytolytic activity against bacteria without a cytolytic activity against red blood cells, is a result of the fact that bacterial cells differ from red blood cells in the composition of their cell membrane. Differences in the compositions of the cell membrane can also be found among a variety of pathogenic cells, such as cancer cells, and normal cells. Thus, based on this finding, the agents of the present invention pave the way for development of a variety of drugs having a selective cytolytic activity against one class of cells within the body such as bacteria cells, cells of a parasite, fungus cells, protozoa cells, or cancer cells, with little or no activity against non-pathogenic normal body cells.

The non-hemolytic cytolytic agents the invention having a selective cytolytic activity against pathogenic cells, while having a much lower, or no cytolytic activity against normal, non-pathogenic cells, may be used for a variety of therapeutic applications with no or little toxic side effects.

One group of cyclic peptides in accordance with the invention are derived from non-α-helical heterogeneous peptides derived from homogeneous peptides with an α-helical structure possessing a broad range cytolytic activity. The present invention thus provides in accordance with one embodiment, a heterogeneous peptide cyclic derivative comprising both D- and L-amino acid residues having a sequence such that a homogeneous open chain peptide comprising only L- or only D-amino acid residues and having the same amino acid sequence as said heterogeneous peptide, has an α-helix configuration and has a broad spectrum cytolytic activity manifested on a variety of cells; said heteroegeneous cyclic peptide having a cytolytic activity on only some of the cells on which said homogeneous peptide is cytolytically active. For example, a cytolytic activity of the heterogeneous cyclic peptide is manifested only on pathogenic cells while having no cytolytic activity on normal cells such as red blood cells.

Examples of non-hemolytic cytolytic cyclic peptides in accordance with the invention are such which are derived from natural peptides which have an α-helical structure and possess a cytolytic activity. The non-α-helical cyclic peptides of the invention have a sequence essentially corresponding to the entire or partial sequence of the natural peptide in which D-amino acids are incorporated along the N- and C-helices of the molecule and a net positive charge is attained either by addition of a positively charged amino acid residue, e.g., lysine, arginine, histidine, for example at the N-terminus and/or of a positively charged group, e.g. aminoalkylamino group such as aminoethylamino, for example at the C-terminus of the molecule, or by neutralization of free carboxyl groups e.g. by converting them to amide groups. Examples of such natural peptides are melittin and pardaxin, and fragments thereof.

For example, the non-α-helical cyclic peptide may be derived from pardaxin which is a 33-mer peptide or from melittin, which is a 26-mer peptide, the non-α-helical cyclic peptide may be a 33-mer or a 26-mer peptide comprising a sequence corresponding to the entire sequence of pardaxin or of melittin, respectively, or may be a non-helical cyclic peptide having a sequence corresponding to a partial sequence of pardaxin or melittin, e.g., 8–23 mer melittin sequence. In the case of a heterogeneous cyclic peptide derived from pardaxin, the heterogeneous cyclic peptide in accordance with the invention may comprise a partial sequence corresponding to that of pardaxin, comprising as little as 10 amino acid residues and ranging between 10 and 24 amino acid residues.

Another group of peptides in accordance with the invention are non-helical peptides which have a sequence having no natural homologs and are composed of at least one hydrophobic and at least one positively charged amino acid and in which sequence at least one amino acid residue is a D-amino acid.

Previous studies with model peptides used to elucidate the structure-function study of antibacterial peptides focused on three parameters; helical structure, hydrophobicity and charge (Anzai et al., 1991; Agawa et al., 1991). Each change in one of these parameters simultaneously resulted in changes in the other two, making it difficult to clarify the unique contribution of each parameter to the overall antibacterial activity. According to the present invention, the effect of the helical structure was eliminated which therefore permitted the study of only two parameters, namely, hydrophobicity and net positive charge, by varying the ratio of leucine and lysine. For this purpose, diastereomers of short model peptides (12 aa. long) containing stretches of only 1—3 consecutive L-amino acids which are too short to form an a-helical structure, where chosen for investigation.

CD spectroscopy revealed that these Leu/Lys diastereomers are indeed totally devoid of α-helical structure (data not shown), unlike the diastereomers of melittin and pardaxin of the invention which retain low α-helical structure. Nevertheless, the Leu/Lys diastereomers exhibit potent antibacterial activity similar to or greater than that of native antibacterial peptides such as dermaseptin S, or the antibiotic drug tetracycline. Moreover, the most potent peptides $[D]-L^{3,4,8,10}-K_4L_8$ and $[D]-L^{3,4,8,10}-K_5L_7$ (peptides 23 and 24, respectively, of Example 3 herein) were devoid of hemolytic activity against the highly cytolytically-susceptible human erythrocytes. It should be noted that $[D]-L^{3,4,8,10}-K_3L_9$ (peptides 22) is devoid of α-helical structure but has considerable hemolytic activity which approaches that of the native cytolytic peptide, pardaxin. This could indicate that the balance between hydrophobicity and positive charge compensates for the amphipathic α-helical structure. However, increasing the positive charge drastically reduced the hemolytic activity while antibacterial activity was preserved, demonstrating that the amphipathic α-helical structure is not required for antibacterial activity.

The interaction of the Leu/Lys diastereomers with both negatively-charged and zwitterionic phospholipid membranes was examined in order to elucidate the basis of their selective cytotoxicity against bacteria. Negatively-charged PE/PG vesicles were used to mimic the lipid composition of *E. coli* (Shaw, 1974), and the zwitterionic PC vesicles to mimic the outer leaflet of human erythrocytes (Verkleij et al., 1973). The biological activity of the Leu/Lys peptides on erythrocytes (FIG. 12) and *E. coli* (Table 5) correlates well with their ability to permeate model membranes. The only peptide which permeated PC vesicles was the only peptide with significant hemolytic activity. These results suggest that the phospholipid composition of the bacterial membrane plays a role in permeation by this family of antibacterial peptides. The ability of antibacterial and non-hemolytic peptides to bind and permeate negatively-charged but not zwitterionic phospholipid vesicles is characteristic of native antibacterial peptides (Gazit et al., 1994), and has been attributed to the fact that the bacterial surface contains lipopolysaccharides (LPS, in Gram-negative bacteria), and polysaccharides (teichoic acids, in Gram-positive bacteria), and their inner membranes contain phosphatidyl glycerol (PG), all of which are negatively charged, while normal eukaryotic cells such as erythrocytes, predominantly express the zwitterionic phospholipid PC on their outer leaflet.

The antibacterial peptide magainin is a non-hemolytic peptide, while melittin, pardaxin, and a model peptide with a sequence similar to that of $[D]-L^{3,4,8,10}-K_4L_8$, but composed of entirely L-amino acids, are hemolytic, mainly due to their high hydrophobicity. When the α-helical structure of magainin was disrupted by the introduction of three D-amino acids, the resulting diastereomer had no antibacterial activity (Chen et al., 1988), even though its net positive charge is similar to that of native magainin. Thus, an optimal balance that already exists between the α-helical structure, hydrophobicity and net positive charge of native magainin, allows selective antibacterial activity, and any change in one of these properties could cause a loss in magainin's antibacterial activity. Contrastingly, hydrophobicity appears to play a major role in compensating for the loss of α-helical structure in melittin, pardaxin and the Leu/Lys diastereomers of the invention.

The results according to the invention suggest a new strategy for the design of a repertoire of short, simple, and easily manipulated antibacterial peptides. Each of the diastereomeric model Leu/Lys peptides has a unique spectrum of activity (Table 5). The existence of a repertoire of diastereomeric antibacterial peptides will enable one to choose the most efficacious peptide with regard to the target cell. Furthermore, simultaneous administration of multiple forms of diastereomers peptides, acting separately or in concert, also has a selective survival value, and provides a better shielding against a wider range of infectious microbes. All the Leu/Lys diastereomers displayed increased antibacterial activity against Gram-positive in comparison to Gram-negative bacteria. These results are important considering the increasing resistance of Gram-positive bacteria such as *Staphylococcus aureus, enterococci,* and *pneumococci* to conventional antibiotics (Russell et al., 1995). In addition, unlike the native antibacterial peptide dermaseptin S, [D]-$L_{3,4,8,10}$-$K_5L_7$ (peptide 24) retained its antibacterial activity in the presence of pooled human serum.

Figure 14:
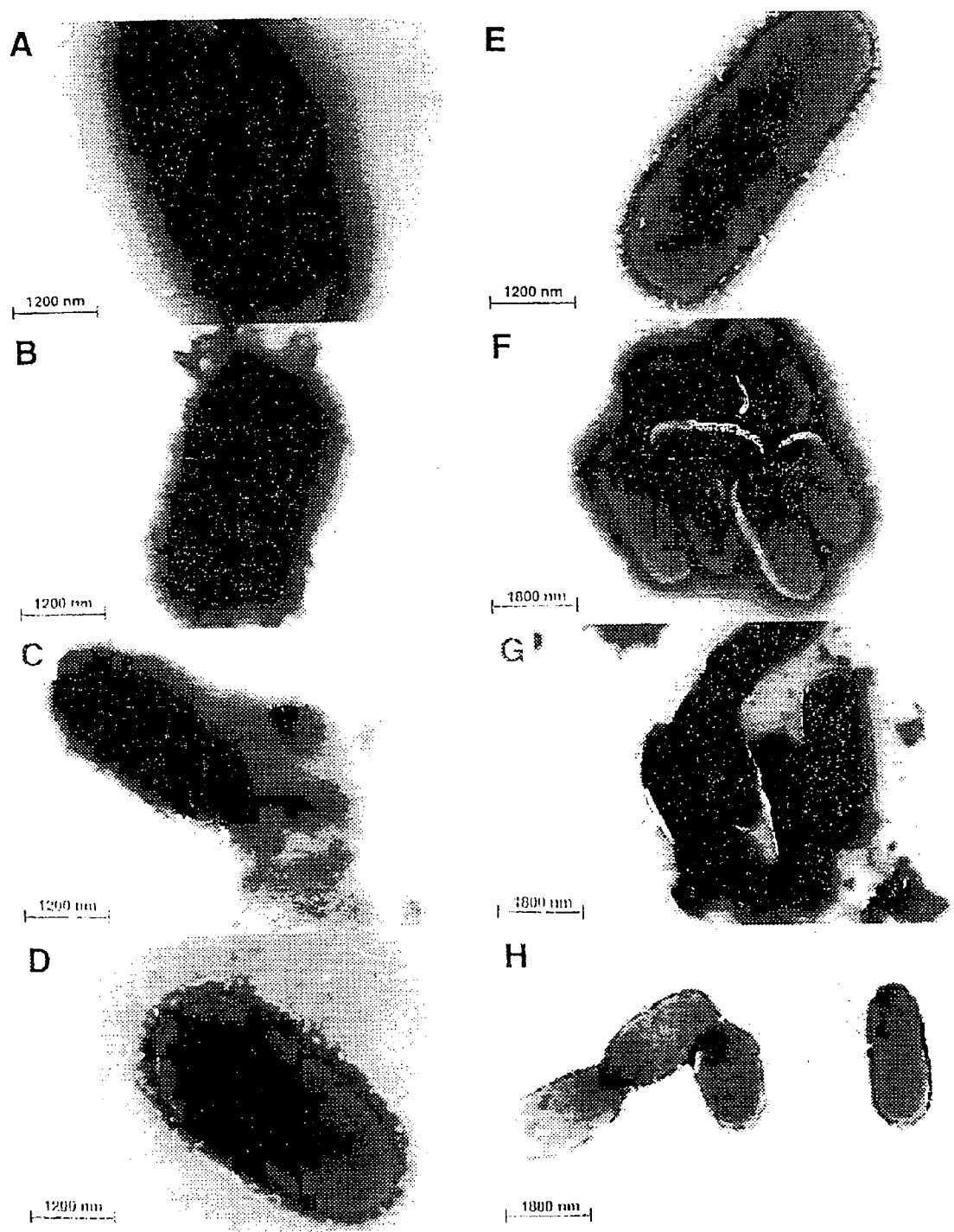
FIGS. 14A–H show electron micrographs of negatively stained *E. coli* untreated and treated with the various Leu/Lys diastereomers at 80% of their MIC.

Diastereomeric peptides should have several advantages over known antibacterial peptides: (1) The peptides should lack the diverse pathological and pharmacological effects induced by α-helical lytic cytolysins. For example, *staphylococcus* δ-toxin, the antibacterial peptide alamethicin, cobra direct lytic factor and pardaxin exert several histopathological effects on various cells due to pore formation and activation of the arachidonic acid cascade. However, pardaxin diastereomers do not exert these activities. In addition, many amphipathic α-helical peptides bind to calmodulin and elicit several cell responses, and even all D-amino acid α-helices, including melittin have similar activity (Fisher et al., 1994). Diastereomers with disrupted α-helical structure are not expected to bind to calmodulin; (2) Local D-amino acid substitution would result in controlled clearance of the antibacterial peptides by proteolytic enzymes, as opposed to the total protection acquired by complete D-amino acids substitution (Wade et al., 1990). Total resistance of a lytic peptide to degradation is disadvantageous for therapeutic use. Furthermore, the antigenicity of short fragments containing D,L amino acids is dramatically altered as compared to their wholly L or D-amino acid parent molecules (Benkirane et al., 1993); (3) Total inhibition of bacterial growth induced by the diastereomers, is associated with total lysis of the bacterial wall, as shown by electron microscopy (FIG. 14). Therefore, bacteria might not easily develop resistance to drugs that trigger such a destructive mechanism; (4) [D]-$L^{3,4,8,10}$-$K_5L_7$ (peptide 24) has the ability to perturb the cell wall of bacteria at concentrations lower than their MIC, as seen by electron microscopy (FIG. 14). The simultaneous administration of clinically used antibiotics, which have no activity due to their inability to penetrate the bacterial cell wall, together with peptide 24, may present a solution to this resistance mechanism of bacteria.

The invention will now be described with reference to some non-limiting drawings and examples.

EXPERIMENTAL PROCEDURES (i) Materials. Butyloxycarbonyl-(amino acid)-(phenylacetamido) methyl resin was purchased from Applied Biosystems (Foster City, Calif.) and butyloxycarbonyl (Boc) amino acids were obtained from Peninsula Laboratories (Belmont, Calif.). Other reagents used for peptide synthesis included trifluoroacetic acid (TFA, Sigma), N,N-diisopropylethylamine (DIEA, Aldrich, distilled over ninhydrin), dicyclohexylcarbodiimide (DCC, Fluka), 1-hydroxybenzotriazole (HOBT, Pierce) and dimethylformamide (peptide synthesis grade, Biolab). Egg phosphatidylcholine (PC) and phosphatidylserine (PS) from bovine spinal cord (sodium salt-grade I) were purchased from Lipid Products (South Nutfield, U.K). Egg phosphatidylglycerol (PG) and phosphatidylethanolamine (PE) (Type V, from *Escherichia coli*) were purchased from Sigma. Cholesterol (extra pure) was supplied by Merck (Darmstadt, Germany) and recrystallized twice from ethanol. 3,3'-Diethylthio-dicarbocyanine iodide [diS-$C_2$-5] was obtained from Molecular Probes (Eugene, Oreg.). Native melittin was purchased from Sigma. Commercially available melittin usually contains traces of phospholipase $A_2$, which causes rapid hydrolysis of phospholipids. Therefore, special care was taken to remove all the phospholipase $A_2$ from melittin using RP-HPLC. All other reagents were of analytical grade. Buffers were prepared in double glass-distilled water.

(ii) Peptide synthesis and purification. Peptides were synthesized by a solid phase method on butyloxycarbonyl-(amino acid)-(phenylacetamido) methyl resin (0.05 meq) (Merrifield et al., 1982). The resin-bound peptides were cleaved from the resins by hydrogen fluoride (HF), and after HF evaporation extracted with dry ether. These crude peptide preparations contained one major peak, as revealed by RP-HPLC, that was 50–70% pure peptide by weight. The synthesized peptides were further purified by RP-HPLC on a $C_{18}$ reverse phase Bio-Rad semi-preparative column (300 Å pore size). The column was eluted in 40 min, using a linear gradient of 10–60% acetonitrile in water, both containing 0.05% TFA (v/v), at a flow rate of 1.8 ml/min. The purified peptides, which were shown to be homogeneous (~95%) by analytical HPLC, were subjected to amino-acid analysis and to mass spectrometry to confirm their sequences.

(iii) Transamination of the peptides. The resin-bound peptides as in (ii) above were transaminated with 30% ethylene diamine in DMF for 3 days, followed by filtration of the resin, precipitation of the protected peptides, namely aminoethylamino (TA) peptides, with ether and removal of the protecting groups with HF. The synthetic TA-peptides were purified (>95% homogenicity) by reverse-phase HPLC on a $C_{18}$ column using a linear gradient of 25–80% acetonitrile in 0.1% TFA, in 40 min, and then subjected to amino acid analysis to confirm their composition.

(iv) Amidation of the peptides. Resin-bound peptide (20 mg) was treated for 3 days with a mixture composed of 1:1 v/v of saturated ammonia solution (30%) in methanol and DMSO (1:1 v/v) which resulted in amidation of the carboxylate group of the glutamine residue located at the C-terminus of [D]-$V^{5,8},I^{17},K^{21}$-melittin. Thus, peptides were obtained in which all the protecting groups remained attached, but whose C-terminal residues were modified by one amide group. The methanol and ammonia were evaporated under a stream of nitrogen, and the protected peptides were extracted from the resin with DMSO, and precipitated with dry ether. The products were then subjected to HF cleavage and to further purification using RP-HPLC as described above.

(v) Preparation of lipid vesicles. Small unilamellar vesicles (SUV) were prepared by sonication of PC/cholesterol (10:1 w/w) or PC/PS (1:1 w/w) dispersions. Briefly, dry lipid and cholesterol (10:1 w/w) were dissolved in a $CHCl_3$/MeOH mixture (2:1 v/v). The solvents were then evaporated under a stream of nitrogen and the lipids (at a concentration of 7.2 mg/ml) were subjected to a vacuum for 1 h and then resuspended in the appropriate buffer, by vortexing. The resultant lipid dispersions were then sonicated for 5–15 min in a bath type sonicator (G1125SP1 sonicator, Laboratory Supplies Company Inc., NY) until clear. The lipid concentrations of the resulting preparations were determined by phosphorus analysis (Bartlett, 1959). Vesicles were visualized using a JEOL JEM 100B electron microscope (Japan Electron Optics Laboratory Co., Tokyo, Japan) as follows. A drop of vesicles was deposited on a carbon-coated grid and negatively stained with uranyl acetate. Examination of the grids demonstrated that the vesicles were unilamellar with an average diameter of 20–50 nm (Papahadjopoulos and Miller, 1967).

(vi) Preparation of serum. Blood was collected from five volunteers and allowed to clot at room temperature for 4 h. The blood was then centrifuged for 15 min at 1500 g, and the serum was removed and pooled. The serum complement was inactivated by heating at 56° C. for 30 min.

(vii) CD Spectroscopy. The CD spectra of the peptides were measured with a Jasco J-500A spectropolarimeter after calibrating the instrument with (+)-10-camphorsulfonic acid. The spectra were scanned at 23° C. in a capped, quartz optical cell with a 0.5 mm path length. Spectra were obtained at wavelengths of 250 to 190 nm. Eight scans were taken for each peptide at a scan rate of 20 nm/min. The peptides were scanned at concentrations of $1.5\times10^{-5}$–$2.0\times10^{-5}$ M in 40% trifluoroethanol (TFE), a solvent that strongly promotes α-helical structure. Fractional helicities (Greenfield and Fasman, 1969; Wu et al., 1981) were calculated as follows:

$$f_h = \frac{[\theta]_{222} - [\theta]^0_{222}}{[\theta]^{100}_{222} - [\theta]^0_{222}}$$

where $[\theta]_{222}$ is the experimentally-observed mean residue ellipticity at 222 nm, and the values for $[\theta]^0_{222}$ and $[\theta]^{100}_{222}$, which correspond to 0% and 100% helix content at 222 nm, are estimated to be 2000 and 32000 deg·cm²/dmole, (viii) Antibacterial activity of the peptides. The antibacterial activity of the diastereomers was examined in sterile 96-well plates (Nunc F96 microtiter plates) in a final volume of 100 µL as follows: Aliquots (50 µl) of a suspension containing bacteria at a concentration of $10^6$ Colony-Forming Units (CFU)/ml LB (Lauria broth) medium were added to 50 µL of water or 66% pooled normal human serum in PBS, containing the peptide in 2-fold serial dilutions. Growth inhibition was determined by measuring the absorbance at 492 nm with a Microplate autoreader E1309 (Bio-tek Instruments), following incubation for 18–20 h at 37° C. Antibacterial activity is expressed as the minimal inhibitory concentration (MIC), the concentration at which 100% inhibition of growth was observed after 18–20 h of incubation. The bacteria used were: *Escherichia coli* D21, *Pseudomonas aeruginosa* ATCC 27853, *Acinetobacter calcoaceticus* Ac11, *Salmonella typhimurium* LT2, *Bacillus megaterium* Bm11, *Micrococcus luteus* ATCC 9341, *Bacillus subtilis* ATCC 6051.

(ix) Hemolysis of human red blood cells. The peptides were tested for their hemolytic activities against human red blood cells (hRBC). Fresh hRBC with EDTA were rinsed 3 times with PBS (35 mM phosphate buffer/0.15 M NaCl, pH 7.3) by centrifugation for 10 min at 800 g and resuspended in PBS. Peptides dissolved in PBS were then added to 50 µL of a solution of the stock hRBC in PBS to reach a final volume of 100 µL (final erythrocyte concentration, 5% v/v). The resulting suspension was incubated under agitation for 30 min at 37° C. The samples were then centrifuged at 800 g for 10 min. Release of hemoglobin was monitored by measuring the absorbance of the supernatant at 540 nm. Controls for zero hemolysis (blank) and 100% hemolysis consisted of hRBC suspended in PBS and Triton 1%, respectively.

(x) Visualization of the effects of the peptides on bacteria by electron microscopy. Samples containing *E. coli* ($10^6$ CFU/ml) in LB medium were incubated with the various peptides at their MIC, and one dilution less than the MIC, for 16 h, and then centrifuged for 10 min at 3000 g. The pellets were resuspended and a drop containing the bacteria was deposited onto a carbon-coated grid which was then negatively-stained with 2% phosphotungstic acid (PTA), pH 6.8. The grids were examined using a JEOL JEM 100B electron microscope.

(xi) Membrane permeation induced by the peptides. Membrane permeation was assessed utilizing the diffusion potential assay (Loew et al., 1983; Sims et al., 1974) as previously described (Shai et al., 1991). In a typical experiment, in a glass tube, 4 µl of a liposomes suspension (final phospholipids concentration of 33 µM), in a $K^+$ containing buffer (50 mM $K_2SO_4$, 25 mM $HEPES-SO_4^{-2}$, pH 6.8), was diluted in 1 ml of an isotonic $K^+$ free buffer (50 mM $Na_2SO_4$, 25 mM $HEPES-SO_4^{-2}$, pH 6.8), and the fluorescent, potential-sensitive dye $diS-C_2$-5 was then added. Valinomycin (1 µl of $10^{-7}$ M) was added to the suspension in order to slowly create a negative diffusion potential inside the vesicles, which led to a quenching of the dye's fluorescence. Once the fluorescence had stabilized, which took 3–10 minutes, peptides were added. The subsequent dissipation of the diffusion potential, as reflected by an increase in fluorescence, was monitored on a Perkin Elmer LS-50B spectrofluorometer, with the excitation set at 620 nm, the emission at 670 nm, and the gain adjusted to 100%. The percentage of fluorescence recovery, $F_t$, was defined as:

$$F_t = (I_t - I_0 / I_f - I_0) \times 100$$

where $I_0$=the initial fluorescence, $I_f$=the total fluorescence observed before the addition of valinomycin, and $I_t$=the fluorescence observed after adding the peptide at time t.

(xii) Binding of peptides to vesicles. The interaction of [D]-$V^{5,8}$,$I^{17}$,$K^{21}$-melittin with vesicles consisting of zwitterionic (PC) or negatively charged phospholipids (PC/PS) was characterized by measuring changes in the emission intensity of the peptides' intrinsic tryptophan in SUV titration experiments. Briefly, SUV were added to a fixed amount of peptide (0.5 µM) dissolved in buffer containing 50 mM $Na_2SO_4$, 25 mM $HEPES-SO_4^{-2}$, pH 6.8, at 24° C. A 1-cm pathlength quartz cuvette that contained a final reaction volume of 2 ml was used in all experiments. The fluorescence intensity was measured as a function of the lipid/peptide molar ratio (4 separate experiments) on a Perkin-Elmer LS-5 Spectrofluorometer, with excitation set at 280 nm, using a 5 nm slit, and emission set at 340 nm, using a 2.5 nm slit. The binding isotherms were analysed as a partition equilibrium, using the following formula:

$$X_b = K_P C_f$$

where $X_b$ is defined as the molar ratio of bound peptide ($C_b$) per total lipid ($C_L$), $K_P$ corresponds to the partition coefficient, and $C_f$ represents the equilibrium concentration of the free peptide in solution. For practical purposes, it was assumed that the peptides initially were partitioned only over the outer leaflet (60%) of the SUV. Therefore, the partition equation becomes:

$$X_b^* = K_P^* C_f$$

where $X_b^*$ is defined as the molar ratio of bound peptide per 60% of total lipid and $K_P^*$ is the estimated surface partition constant. The curve resulting from plotting $X_b^*$ vs. free peptide, $C_f$ is referred to as the conventional binding isotherm.

(xiii) Tryptophan quenching experiments. Tryptophan which is sensitive to its environment has been utilized previously in combination with brominated phospholipids (Br-PC) to evaluate peptide localization in the membrane (Bolen and Holloway, 1990; De Kroon et al., 1990). Br-PC employed as quenchers of tryptophan fluorescence are suitable for probing the membrane insertion of peptides, since they act over a short distance and do not drastically perturb the membrane. Melittin and its diastereomer, each of which contains one tryptophan residue, were added (final concentration of 0.5 $\mu$M) to 2 ml of buffer (50 mM $Na_2SO_4$, 25 mM $HEPES-SO_4^{-2}$, pH 6.8) containing 20 $\mu$l (50 $\mu$M) of Br-PC/PS (1:1 w/w) SUV, thus establishing a lipid/peptide ratio of 100:1. After a 2 min incubation at room temperature, an emission spectrum of the tryptophan was recorded using a Perkin-Elmer LS-50B Spectrofluorometer, with excitation set at 280 nm (8 nm slit). SUV composed of PC/PS (1:1 w/w) and which contained 25% of either 6,7 Br-PC, or 9,10 Br-PC, or 10,11 Br-PC, were used. Three separate experiments were conducted for each peptide. In control experiments, PC/PS (1:1 w/w) SUV without Br-PC were used.

EXAMPLE 1

Synthesis and Biological Activity of Pardaxin-Derived Diastereomers 1.1 Synthesis. To examine the role of the α-helical structure of a polycationic cytolysin in its cytotoxicity towards mammalian cells and bacteria, a series of pardaxin-derived peptides were synthesized as described in sections (ii) and (iii) of the Experimental Procedures, and characterized for their structure, hemolytic activity on hRBCs, antibacterial activity and effect on the morphology of bacteria.

Pardaxin (par) is a 33-mer peptide of the following sequence:

Gly-Phe-Phe-Ala-Leu-Ile-Pro-Lys-Ile-Ile-Ser-Ser-Pro-Leu-Phe-Lys-Thr-Leu-Leu-Ser-Ala-Val-Gly-Ser-Ala-Leu-Ser-Ser-Ser-Gly-Gly-Gln-Glu (SEQ ID NO:98)

Modification of the pardaxin molecule in order to introduce a positive charge was made by either deleting the acidic C-terminus of pardaxin or converting the acidic C-terminus of pardaxin or of a fragment thereof to a positive one by reaction of both carboxyl groups of the Glu residue at the C-terminus with ethylene diamine (TA), and/or adding positively charged amino acid residues such as Lys to the N-terminus, in pardaxin diastereomers in which the N-helix and/or the C-helix were altered by either replacing the residue Pro at position 7 of TApar or of a pardaxin fragment by D-Pro (herein indicated by [D]P$^7$), or the two Leu residues at positions 18 and 19 of TApar or of a pardaxin fragment by D-Leu (herein [D]L$^{18}$L$^{19}$), or both (herein [D]P$^7$L$^{18}$L$^{19}$). The D-amino acids were introduced in the centers of the N- and C-helices.

The following pardaxin-derived diastereomers were found to be non-hemolytic and to exhibit selective cytolytic activity (the bold and underlined residues are D-amino acids). The peptides will be represented hereinafter by numerals in bold.

1. [D]P$^7$L$^{18}$L$^{19}$-TApar of the sequence: Gly-Phe-Phe-Ala-Leu-Ile-<u>Pro</u>-Lys-Ile-Ile-Ser-Ser-Pro-Leu-Phe-Lys-Thr-<u>Leu-Leu</u>-Ser-Ala-Val-Gly-Ser-Ala-Leu-Ser-Ser-Ser-Gly-Gly-Gln-Glu-(NH—$CH_2$—$CH_2$—$NH_2$)$_2$ (SEQ ID NO:1)
2. [D]P$^7$L$^{18}$L$^{19}$[1-22]-TApar of the sequence: Gly-Phe-Phe-Ala-Leu-Ile-<u>Pro</u>-Lys-Ile-Ile-Ser-Ser-Pro-Leu-Phe-Lys-Thr-<u>Leu-Leu</u>-Ser-Ala-Val-NH—$CH_2$—$CH_2$—$NH_2$ (SEQ ID NO:2)
3. [D]P$^7$L$^{18}$L$^{19}$[1-22]-par of the sequence: Gly-Phe-Phe-Ala-Leu-Ile-<u>Pro</u>-Lys-Ile-Ile-Ser-Ser-Pro-Leu-Phe-Lys-Thr-<u>Leu-Leu</u>-Ser-Ala-Val (SEQ ID NO:3)
4. K$^1$[D]P$^7$L$^{18}$L$^{19}$[1-22]-TApar of the sequence: Lys-Gly-Phe-Phe-Ala-Leu-Ile-<u>Pro</u>-Lys-Ile-Ile-Ser-Ser-Pro-Leu-Phe-Lys-Thr-<u>Leu-Leu</u>-Ser-Ala-Val-NH—$CH_2$—$CH_2$—$NH_2$ (SEQ ID NO:4)
5. K$^1$K$^2$[D]P$^7$L$^{18}$L$^{19}$[1-22]-TApar of the sequence: Lys-Lys-Gly-Phe-Phe-Ala-Leu-Ile-<u>Pro</u>-Lys-Ile-Ile-Ser-Ser-Pro-Leu-Phe-Lys-Thr-<u>Leu-Leu</u>-Ser-Ala-Val-NH—$CH_2$—$CH_2$—$NH_2$ (SEQ ID NO:5)
6. K$^1$K$^2$[D]P$^7$L$^{18}$L$^{19}$[1-22]-par of the sequence: Lys-Lys-Gly-Phe-Phe-Ala-Leu-Ile-<u>Pro</u>-Lys-Ile-Ile-Ser-Ser-Pro-Leu-Phe-Lys-Thr-<u>Leu-Leu</u>-Ser-Ala-Val (SEQ ID NO:6)
7. [D]P$^7$-[1-11]-TApar of the sequence: Gly-Phe-Phe-Ala-Leu-Ile-<u>Pro</u>-Lys-Ile-Ile-Ser-NH—$CH_2$—$CH_2$—$NH_2$ (SEQ ID NO:6)

The following pardaxin derivatives were synthesized and found to be hemolytic as shown in Table 1 hereinafter:

8. TApar (SEQ ID NO:8)
9. [D]P$^{13}$-TApar (SEQ ID NO:9)
10. [D]L$^5$L$^{19}$-TApar (SEQ ID NO:10)
11. [D]P$^7$L$^{19}$-TApar (SEQ ID NO:11)
12. [D]P$^7$-TApar (SEQ ID NO:12)
13. [D]P$^7$-par (SEQ ID NO:13)
14. [D]L$^{18}$L$^{19}$-TApar (SEQ ID NO:14)
15. [D]L$^{18}$L$^{19}$-par (SEQ ID NO:15)
16. [D]P$^7$L$^{18}$L$^{19}$-par (SEQ ID NO:16)
17. [D]P$^7$[1-22]-TApar (SEQ ID NO:17)

1.2 Determination of the secondary structure of the peptides. The secondary structures of the peptides 1, 8, 12, 14, were evaluated from their CD spectra in 40% TFE, a solvent that strongly promotes an α-helical structure, as described in Experimental Procedures, section (vii), and in PBS (35 mM phosphate buffer/0.15 M NaCl, pH 7.0).

The CD spectra of the pardaxin-derived diastereomers are shown in FIG. 1 wherein [8] (_), [12] (.......), [14] (-----), and [1] (-.-- -.-.). As expected, a dramatic decrease in the α-helix content of the peptides was observed as more D-amino acids were incorporated, as reflected by the minima at 208 and 222 nm in 40% TFE. There was a more than 90% decrease in the α-helix content between 8 (TApar) (50% α-helix) and 1 ([D]P$^7$L$^{18}$L$^{19}$-TApar) (4%). The α-helix contents of 12 ([D]P$^7$-TApar) and 14 ([D]L$^{18}$L$^{19}$-TApar) were 25% and 15%, respectively. It should be noted that proline at position 7 does not introduce a kink in the structure but rather participates in the formation of the N-helix as revealed by NMR spectroscopy (Zagorski et al., 1991). In PBS, pardaxin gave a low value of ~12% α-helix content while all the analogues with D-amino acid residues gave very low signals that could not be attributed to specific structures (data not shown).

1.3 Hemolytic and antibacterial activity. The pardaxin-derived peptides 1–17 were then examined for their hemolytic activity towards the highly susceptible human erythrocytes, and for their potential to inhibit the growth of different species of bacteria, as described in Experimental Procedures, sections (ix) and (xviii), respectively. In addition, the cytotoxic bee venom melittin, the antibacterial peptide dermaseptin S, and the antibiotic tetracycline were used as controls.

Figure 2:
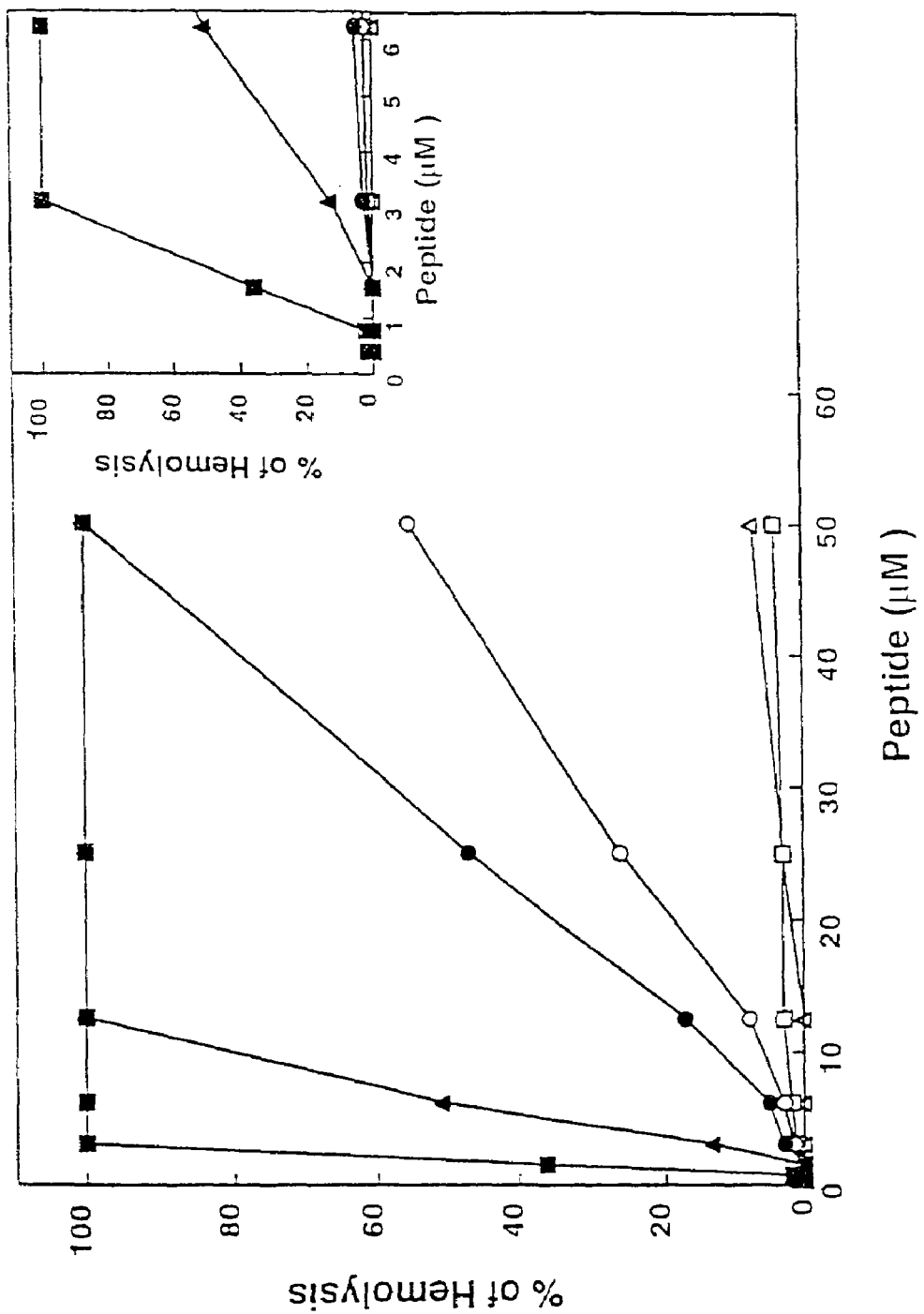
FIG. 2 depicts dose-response curves of the hemolytic activity of TApar-derived peptides towards human red blood cells (hRBC). The inset shows the assay results at low concentration. Symbol: Filled squares, melittin; filled triangles, TApar; filled circles, [D]P$^7$-TApar; empty circles, [D]L$^{18}$L$^{19}$-TApar; empty squares, [D]P$^7$L$^{18}$L$^{19}$-TApar; empty triangles, dermaseptin.

FIG. 2 shows the dose response curves of the hemolytic activity of the peptides 1, 8, 12, 14. It is shown that D-amino acids introduced into TApar dramatically reduced its hemolytic activity, which correlates with the loss of α-helix content in the corresponding analogues. Peptide 8, TApar, with the highest α-helix content is the most hemolytic, while Peptide 1, [D]P$^7$L$^{18}$L$^{19}$-TApar, with the lowest α-helix content, is practically devoid of hemolytic activity up to the maximum concentration tested (50 μM). The inability to lyse RBCs is characteristic of most of the naturally occurring antibacterial peptides such as dermaseptin (see FIG. 2), magainin and cecropins.

Table 1 gives the MIC (in μM) of the peptides 1–17 for a representative set of test bacteria, which includes two Gram-negative species, *Escherichia coli* and *Acinetobacter calcoaceticus*, and two Gram-positive species, *Bacillus megaterium* and *Bacillus subtilis*, as well as the % hemolysis at 50 μM peptide. Table 2 gives the MIC (in μM) of the peptides 1, 8, 12, 14 and of melittin, dermaseptin S and tetracycline for some bacterial species The data reveal that despite the dramatic decrease in the α-helix content and hemolytic activity of the diastereomeric analogues 1–7, they all retained most of the potent antibacterial activity of the parent peptide pardaxin, which is comparable to that of known native antibacterial peptides.

TABLE 1

Minimal Inhibitory Concentration (μM) and hemolytic activity of diastereomers pardaxin analogoues.

Minimal Inhibitory Concentration (μM)

| Peptide | E. coli (D21) | A. calcoaceticus (Ac11) | B. megaterium (Bm11) | M. luteus (ATCC 9341) | S. typhimurium (LT2) | P. aeruginosa (ATCC 27853) | % hemolysis at 50 μM peptide |
|---|---|---|---|---|---|---|---|
| 1. | 6 | 6 | 0.9 | 12.5 | N.D | N.D | 5 |
| 2. | 12.5 | 12.5 | 2.5 | N.D[a] | N.D | N.D | 0 |
| 3. | 130 | >130 | 30 | N.D | >130 | >130 | 0 |
| 4. | 7.5 | 7.5 | 1.5 | N.D | N.D | N.D | 0 |
| 5. | 3.5 | 3.5 | 0.75 | N.D | N.D | N.D | 0 |
| 6. | 15 | 6 | 6 | N.D | 120 | 60 | 0 |
| 7. | >120 | >120 | 30 | N.D | >120 | >120 | 0 |
| 8. | 3 | 3 | 0.8 | 5 | 15 | 8 | 100 |
| 9. | 3 | N.D | 1.5 | N.D | N.D | N.D | 83 |
| 10. | 3 | N.D | 1.3 | N.D | N.D | N.D | 56 |
| 11. | 3 | N.D | 1.5 | N.D | N.D | N.D | 82 |
| 12. | 10 | 5 | 1.2 | 5 | N.D | N.D | 49 |
| 13. | 30 | 15 | 3.5 | N.D | >100 | >100 | 23 |
| 14. | 3.5 | 1.5 | 0.6 | 2.5 | N.D | N.D | 100 |
| 15. | 15 | 3.5 | 1.7 | N.D | 60 | 60 | 44 |
| 16. | 100 | 100 | 50 | N.D | >100 | >100 | 0 |
| 17. | 10 | N.D | 1 | N.D | N.D | N.D | 17 |

[a]N.D, not determined.

TABLE 2

Minimum Inhibitory concentration (μM)[a] of the peptides.

| Bacterial species | Strain | 8 | 12 | 14 | 1 | Melittin | DermaseptinS | Tetracycline |
|---|---|---|---|---|---|---|---|---|
| *Escherichia coli* | D21 | 3 | 10 | 3.5 | 6 | 5 | 6 | 1.5 |
| *Acinetobacter calcoaceticus* | Ac11 | 3 | 5 | 2.5 | 6 | 2 | 3 | 1.5 |
| *Bacillus megaterium* | Bm11 | 0.8 | 1.2 | 0.6 | 0.9 | 0.3 | 0.5 | 1.2 |
| *Bacillus subtilis* | ATCC-6051 | 1.5 | 2 | 1.5 | 3 | 0.6 | 4 | 6.5 |

[a]Results are the mean of 3 independent experiments each performed in duplicates, with standard deviation of 20%.

Figure 3:
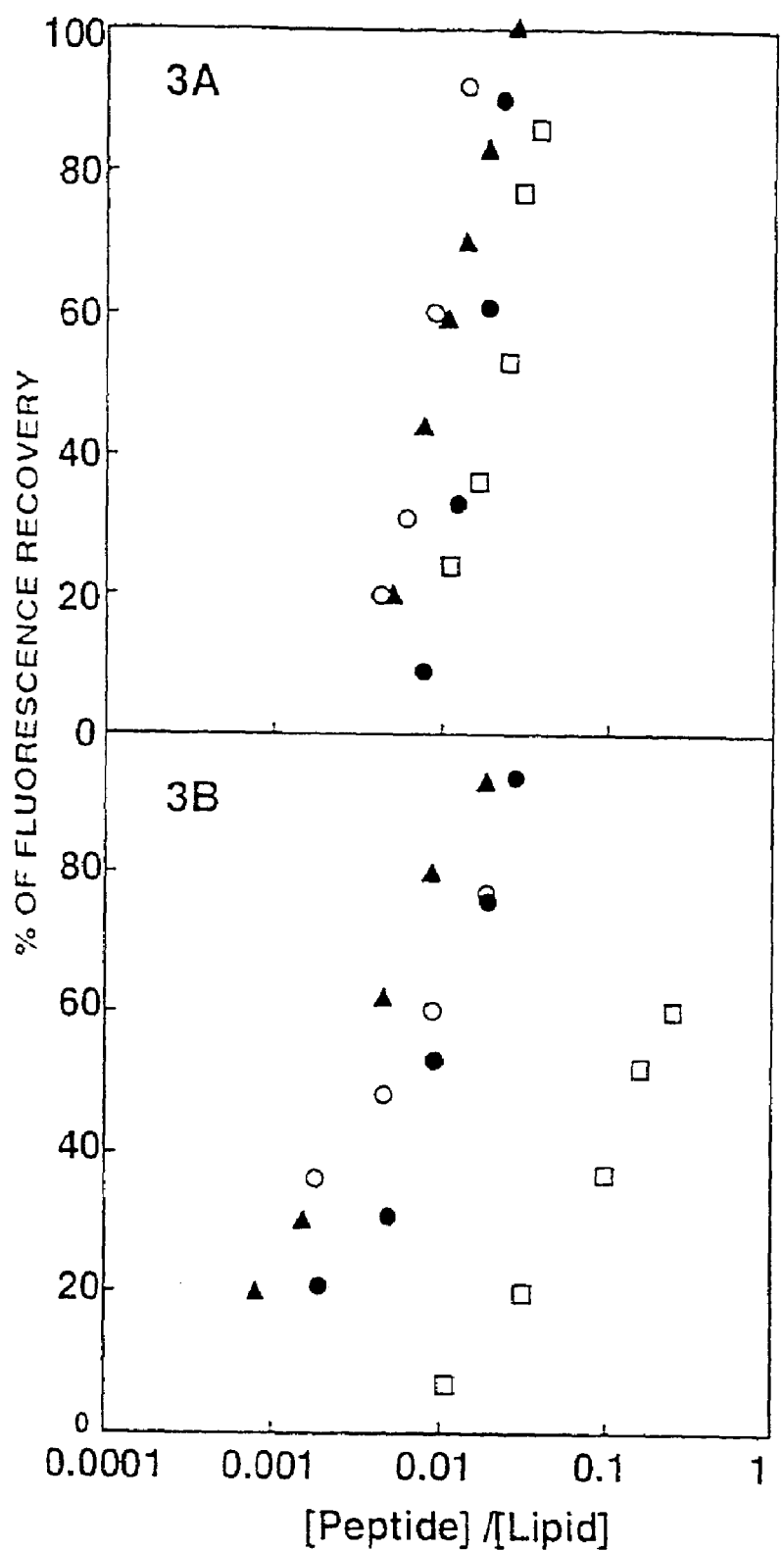
FIGS. 3A–B show the maximal dissipation of the diffusion potential in vesicles induced by the TApar-derived peptides. The peptides were added to isotonic K$^+$ free buffer containing small unilamellar vesicles (SUV) composed of egg phosphatidylcholine/phosphatidylserine (PC/PS) (FIG. 3A) or PC (FIG. 3B), pre-equilibrated with the fluorescent dye diS-C$_2$-5 and valinomycin. Fluorescence recovery was measured 10–20 min after the peptides were mixed with the vesicles. Symbols: Filled triangles, TApar; filled circles, [D]P$^7$-TApar; empty circles, [D]L$^{18}$L$^{19}$-TApar; empty squares, [D]$^7$L$^{18}$L$^{19}$-TApar.

1.4 Membrane destabilization induced by the pardaxin-derived peptides. A common property of all of the α-helical, positively charged, naturally-occurring antibacterial peptides studied so far, is their ability to interact and permeate negatively charged phospholipids better than zwitterionic phospholipids. The relevance of these findings to their biological target membranes has been attributed to the fact that the surface of bacteria contains lipopolysaccharides (LPS, in Gram-negative bacteria), and polysaccharides (teichoic acids, in Gram-positive bacteria), both of which are acidic, while normal mammalian cells (e.g., erythrocytes) express the predominantly zwitterionic phospholipid PC on their outer leaflet. The dissipation of the diffusion potential to assess the membrane permeating activity of the peptides on both PC and PC/PS phospholipid vesicles (prepared according to Experimental Procedures, section v) was assayed as described in Experimental Procedures, section xi. The results shown in FIG. 3 for peptides 1, 8, 12, 14, indicate that D-amino acids introduced into pardaxin did not significantly affect the ability of the peptides to permeate phospholipid membranes. However, peptide 1, the only diastereomer that is devoid of hemolytic activity but retains antibacterial activity, permeates negatively charged phospholipids significantly better than zwitterionic phospholipids. As such it behaves similar to native antibacterial peptides, although it is devoid of α-helical structure. The lack of significant intermediate activities with peptides 12 and 14 might be explained by the fact that they both have either the hydrophobic N-helix or the amphipathic C-helix intact, which is sufficient to promote strong binding to both types of vesicles via hydrophobic interactions.

Figure 4:
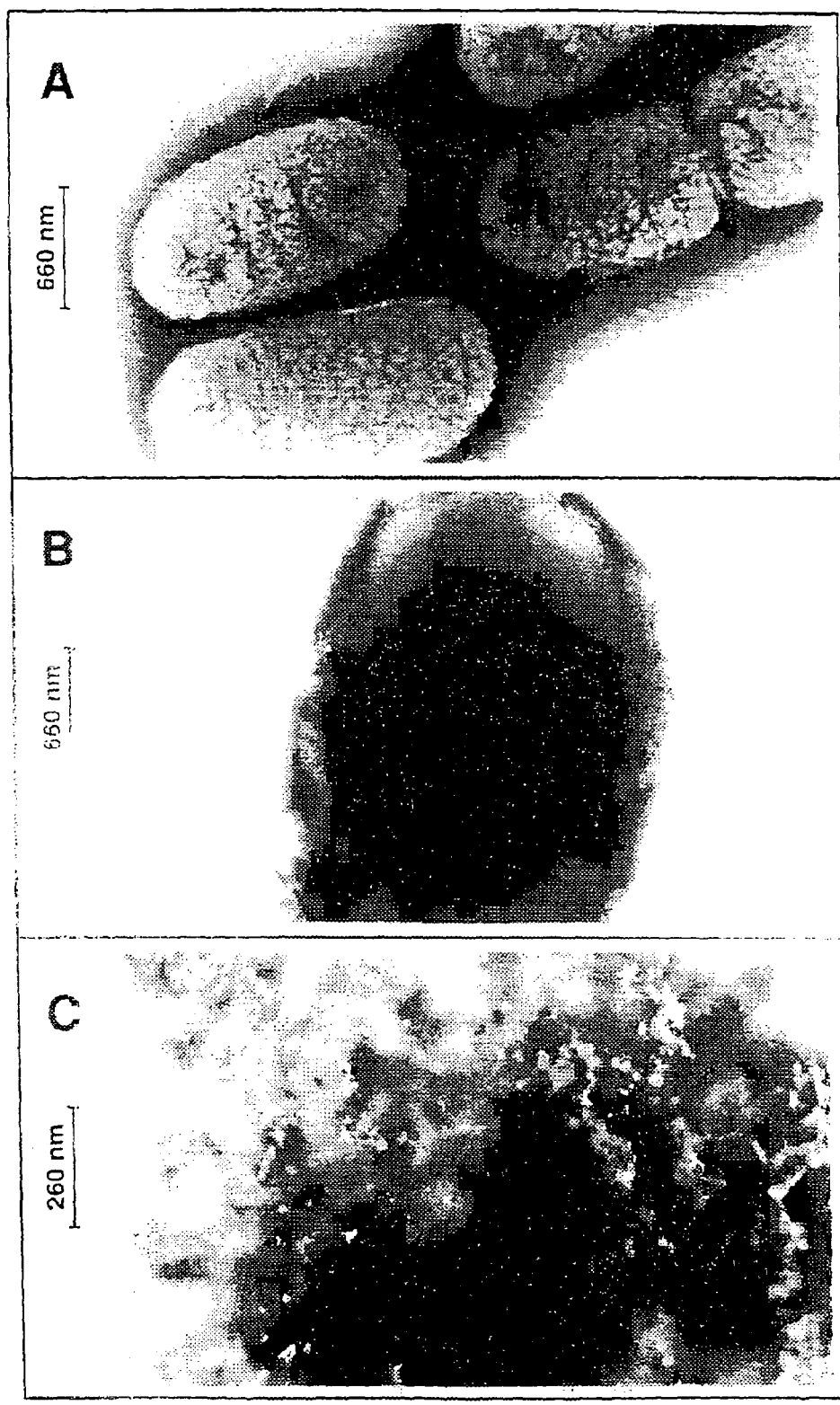
FIGS. 4A–C show electron micrographs of negatively stained E.coli cell untreated (FIG. 4A) or treated with [D]P$^7$L$^{18}$L$^{19}$-TApar at concentration lower than the minimal inhibitory concentration (MIC) (4B) or at MIC concentrations (4C)

1.5 Visualization of bacterial lysis using electron microscopy. The effect of the pardaxin-derived peptides on the morphology of intact and treated bacteria was visualized using negative staining electron microscopy, as described in Experimental Procedures, section xx. The peptides were added to bacteria at or below their MIC concentration under the same conditions used in the antibacterial assay (see example 1.3 above). Samples were pulled out after an 18 h incubation and were immediately fixed and examined by transmission electron microscopy. FIG. 4 shows the photographs obtained with the non-hemolytic analogue 1, [D]$P^7L^{18}L^{19}$-TApar, as an example. It was found that at the MIC peptide 1 lysed the bacteria completely, and only small fragments could be observed (FIG. 4C). However, at concentrations lower than the MIC, patches were observed on the bacterial wall (FIG. 4B). These patches might indicate the initial step involved in the lytic process.

EXAMPLE 2

Synthesis and Biological Activity of Melittin-Derived Diastereomers 2.1 Synthesis. In order to further examine the role of the α-helical structure of cytolysins in their cytotoxicity against mammalian cells and bacteria and to gain insight into the mechanism underlying this effect, four diastereomers of melittin (mel) were synthesized.

Melittin is a 26-mer peptide of the sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-$NH_2$ (SEQ ID NO:99)

Modification of the melittin molecule in order to introduce a positive charge was made by converting the acidic C-terminus of melittin or of a fragment thereof to a positive one by reaction of the carboxyl group at the C-terminus with ethylene diamine, in melittin diastereomers in which the N-helix and the C-helix were altered by replacing the two Val residues at positions 5 and 8 of melittin, the Ile residue at position 17 and the Lys residue at position 21 by D-Val, D-Ile and D-Lys, respectively (herein [D]-$V^5V^8I^{17}K^{21}$).

The following melittin-derived diastereomers were found to be non-hemolytic and to exhibit selective cytolytic activity (the bold and underlined residues are D-amino acids):

18. [D]-$V^5V^8I^{17}K^{21}$-mel of the sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-$NH_2$ (SEQ ID NO:18)

19. [D]-$V^5V^8I^{17}K^{21}$-mel-COOH of the sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-COOH (SEQ ID NO:19)

20. [D]-$V^5V^8I^{17}K^{21}$-[1-22]-TAmel of the sequence: Gly-Ile-Gly-Ala-Val-Leu-Lys-Val-Leu-Thr-Thr-Gly-Leu-Pro-Ala-Leu-Ile-Ser-Trp-Ile-Lys-Arg-NH—$CH_2$—$CH_2$—$NH_2$ (SEQ ID NO:20)

21. [D]-$V^5V^8I^{17}K^{21}$-[4-22]-TAmel of the sequence: Ala-Val-Leu-Lys-Val-Leu-Thr-Thr-Gly-Leu-Pro-Ala-Leu-Ile-Ser-Trp-Ile--Lys-Arg-NH—$CH_2$—$CH_2$—$NH_2$ (SEQ ID NO:21)

The peptides 18–21 were then characterized with regard to their structure, biological function and interaction with bacteria and model membranes composed of either zwitterionic or negatively charged phospholipids.

Figure 5:
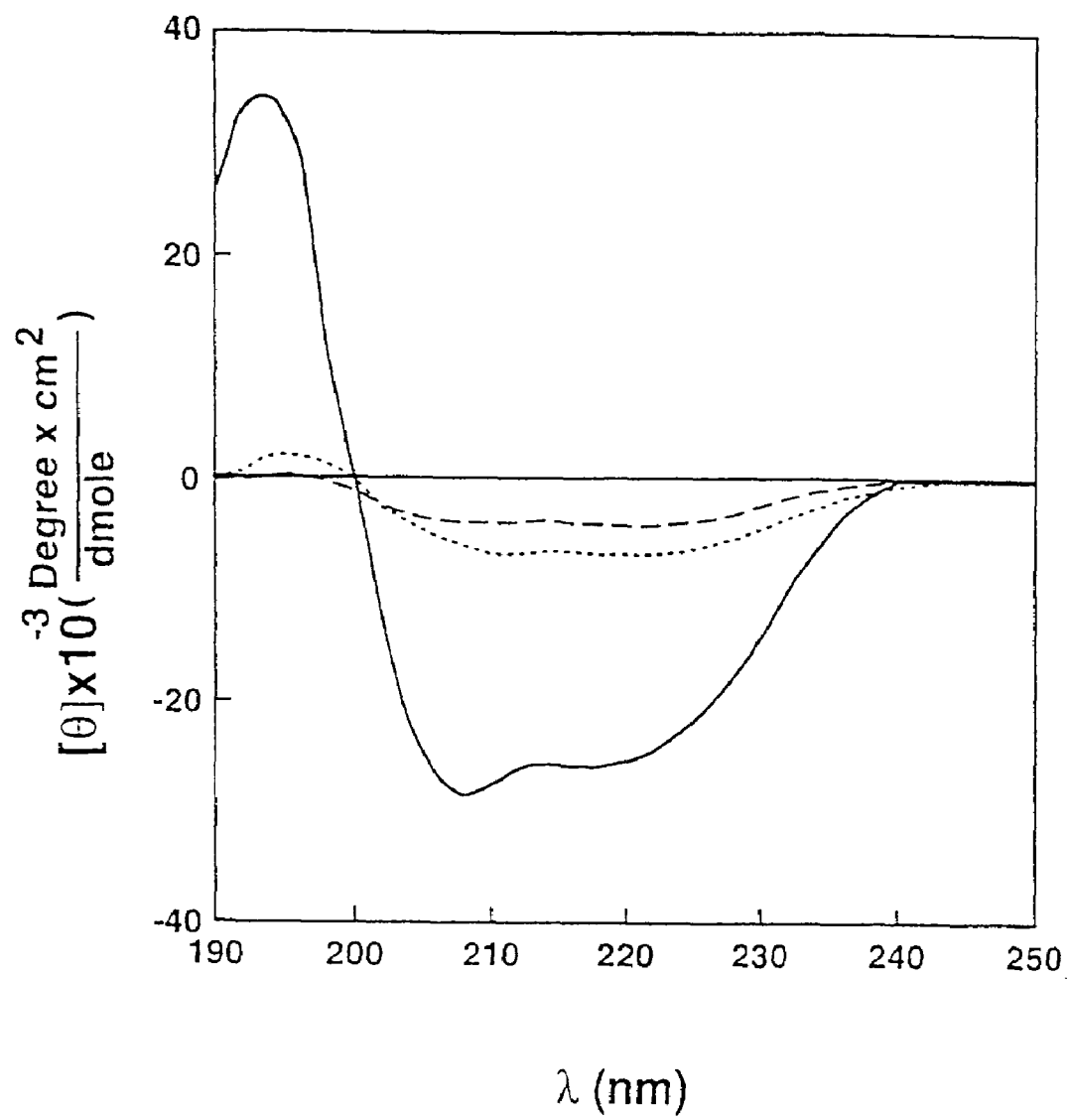
FIG. 5 shows CD spectra of melittin and melittin-derived diastereomers. Spectra were taken at peptide concentrations of $0.8–0.2 \times 10^{-5}$ M in 40% TFE/water. Symbols: melittin, (__); [D]-V$^{5,8}$I$^{17}$,K$^{21}$-melittin, (. . . . .); [D]-V$^{5,8}$,I$^{17}$,K$^{21}$-melittin-COOH, (- - - - -).

2.2 CD spectroscopy. The extent of the α-helical structure of the peptides 18 and 19 was determined from their CD spectra in 40% TFE, a solvent that strongly promotes α-helical structure. As expected, the α-helical content of the diastereomers was much lower (80% decrease) than that of melittin, as reflected by the minima at 208 and 222 nm (FIG. 5). The α-helix content of melittin was 73% compared to 15% and 7% in its diastereomers, 18 and 19, respectively.

Figure 6:
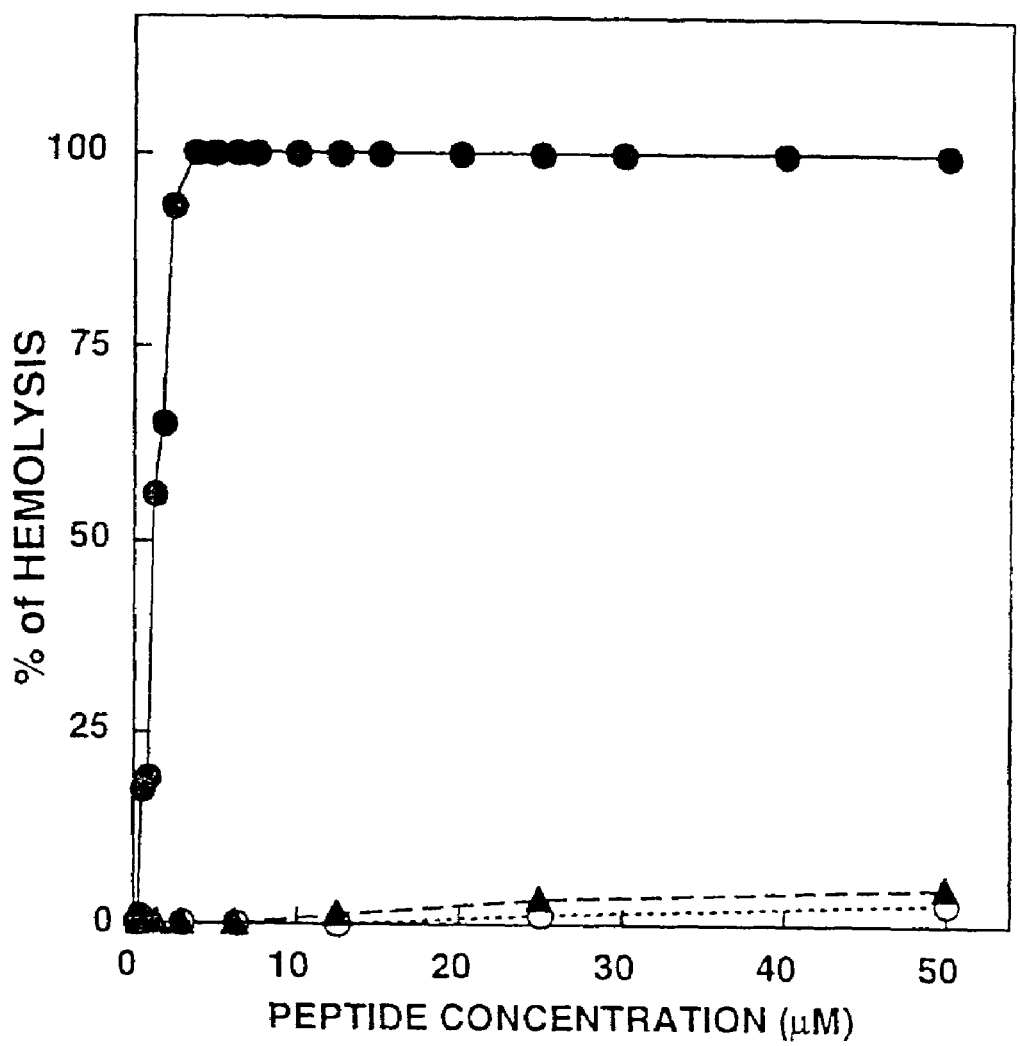
FIG. 6 depicts dose-response curves of the hemolytic activity of the melittin-derived diastereomers towards hRBC. Symbols: filled circles, melittin; empty circles, [D]-V$^{5,8}$,I$^{17}$,K$^{21}$-melittin-COOH; filled triangles, [D]-V$^{5,8}$,I$^{17}$, K$^{21}$-melittin.

2.3 Antibacterial and hemolytic activity of the melittin diastereomers 18–21. The hemolytic activity of the peptides 18–21 against hRBC and their potential to inhibit the growth of different species of bacteria were investigated. The antibiotic tetracycline served as a control in the antibacterial assay. A dose response curve for the hemolytic activity of the peptides was obtained (FIG. 6). Table 3 gives the MIC for a representative set of test bacteria. It can be seen that the introduction of D-amino acids into melittin dramatically reduced its hemolytic activity, which paralleled the loss of the α-helical content in the corresponding analogues. Melittin, with the highest α-helical content was the most hemolytic, while up to the maximum concentration tested (50 μM), peptides 18 and 19, with the lowest α-helical content, were practically devoid of hemolytic activity. However, despite the dramatic decrease in the hemolytic activity of the melittin diastereomers 18 and 19, they both retained most of the potent antibacterial activity of the parent peptide. Furthermore, the antibacterial activity of peptide 19 was only slightly lower than that of 18, which indicates that the amide group at the C-terminus of melittin does not contribute significantly to the antibacterial activity. In contrast, it is known that cecropin with a free carboxylic C-terminal has a significant lower antibacterial activity than that of the native cecropin with an amidated C-terminal (Li et al., 1988).

TABLE 3

Minimal Inhibitory concentration (μM) and Hemolytic activity of diastereomer melittin analogues.

| Peptide designation | Minimal Inhibitory Concentration (μM) | | | | | % hemolysis at 50 μM peptide |
|---|---|---|---|---|---|---|
| | E. coli (D21) | A. calcoaceticus (Ac11) | B. megaterium (Bm11) | M. luteus (ATCC 9341) | B. subtilis (ATCC 6051) | |
| Melittin | 5 | 20 | 0.3 | 0.4 | 0.4 | 100 |
| 18 | 12 | 12 | 0.8 | 25 | 3.5 | 0 |
| 19 | 18 | 18 | 1.2 | 50 | 8 | 0 |
| 20 | 8 | 7 | 0.8 | 29 | N.D | 0 |
| 21 | 21 | 14 | 1.2 | 28 | N.D | 0 |
| Dermaseptin-S | 6 | 3 | 0.5 | N.D | 4 | 9 |
| Tetracycline | 1.5 | 1.5 | 1.2 | N.D | 6.5 | — |

Figure 7:
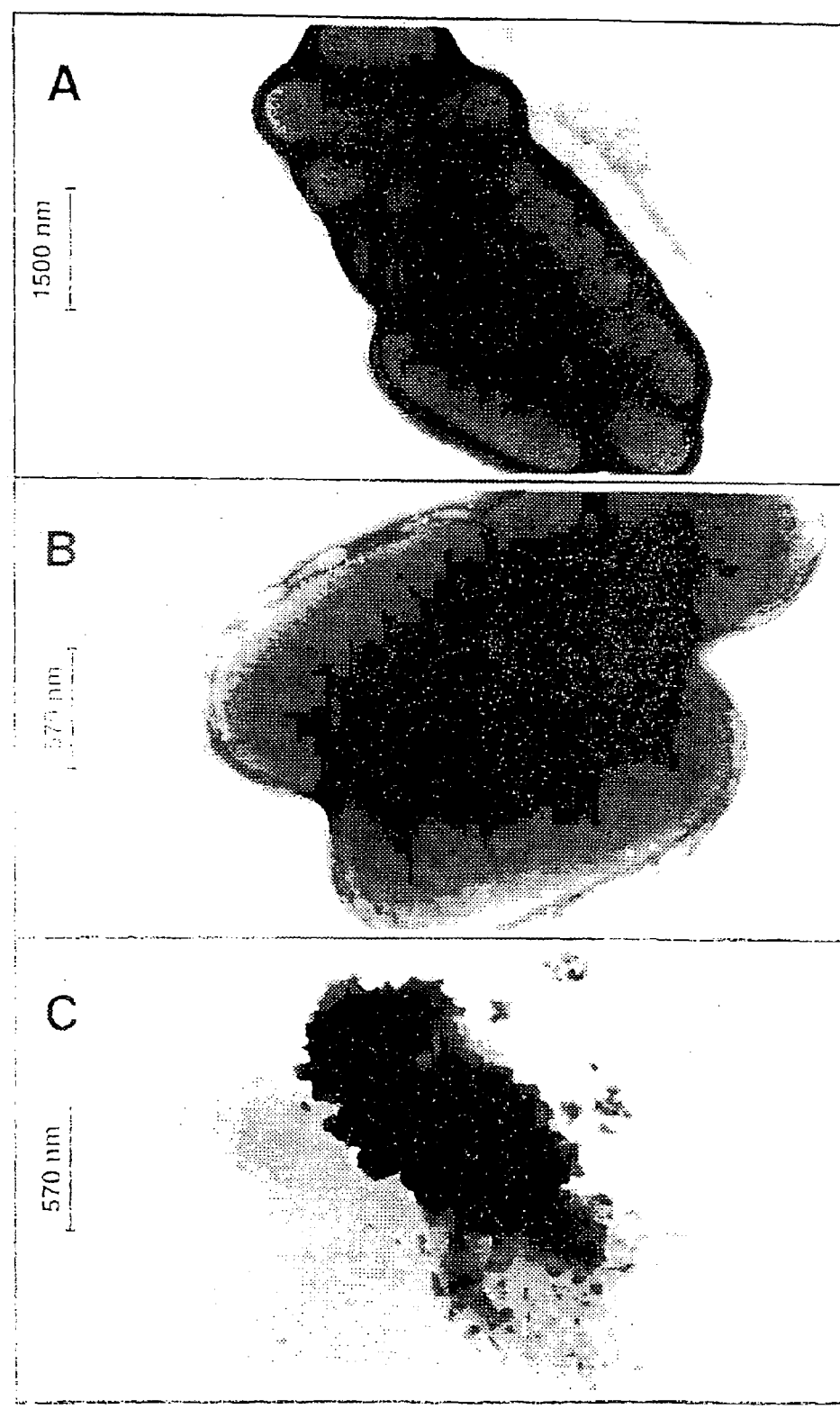
FIGS. 7A–C shows electron micrographs of negatively stained E. coli untreated (FIG. 7A) or treated with [D]-V$^{5,8}$, I$^{17}$,K$^{21}$-melittin at concentrations lower than the MIC (7B) or at the MIC concentrations (7C).

2.4 Electron microscopy study of bacterial lysis. The effect of the peptide 18 on the morphology of intact and treated bacteria was visualized using transmission electron microscopy. As shown in FIG. 7, at the MIC, the peptide 18 caused total lysis of the bacteria (FIG. 7C). However, at concentrations lower then the MIC, patches were observed on the bacterial wall (FIG. 7B). These patches might represent an initial step in the lytic process.

2.5 Mode of interaction with phospholipid membranes. Since the biological activities of the peptides 18 and 19 were similar, only the mode of interaction of peptide 18 with model phospholipid membranes was compared to that of melittin, in order to elucidate the basis of the membrane selectively observed. For that purpose the ability of the peptides to dissipate the diffusion potential created in both PC and PC/PS vesicles were measured, and the partition coefficients of the peptides with both types of vesicles, and the localization of the peptide when bound to membranes, were determined.

Figure 8:
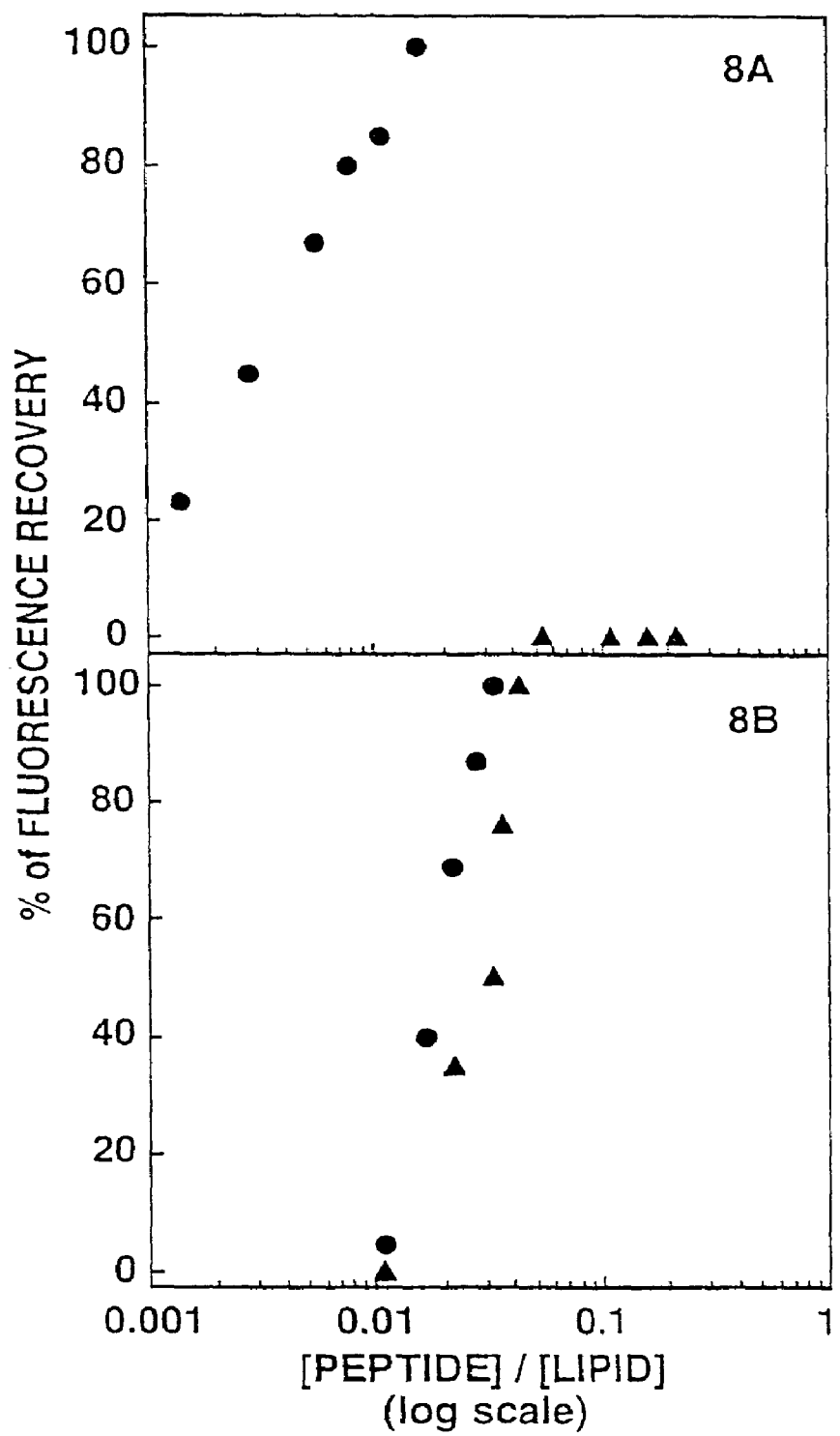
FIGS. 8A–B shows maximal dissipation of the diffusion potential in vesicles induced by melittin and a melittin-derived diastereomer. The peptides were added to isotonic K$^+$ free buffer containing SUV composed of PC (8A) or PC/PS (8B), pre-equilibrated with the fluorescent dye diS-C$_2$-5 and valinomycin. Fluorescence recovery was measured 10–20 min after the peptides were mixed with the vesicles. Symbols: filled circles, melittin; filled triangles, [D]-V$^{5,8}$, I$^{17}$,K$^{21}$-melittin.

2.5.1 Membrane permeability induced by the peptides. Various concentrations of melittin and peptide 18 were mixed with vesicles that had been pre-treated with the fluorescent dye, diS-$C_2$-5, and valinomycin. The kinetics of the fluorescence recovery was monitored with time and the maximum lead reached as a function of peptide concentration was determined. As shown in FIG. 8, both melittin and peptide 18 had similar membrane permeating activity with PC/PS vesicles, which demonstrated that introduction of D-amino acids into melittin does not affect the ability of the resulting diastereomer to permeate negatively charged phospholipid (PS/PC) membranes. However, while melittin was also highly active with PC vesicles, the diastereomer was totally devoid of membrane permeating activity with PC vesicles (up to the maximal concentration tested).

Figure 9:
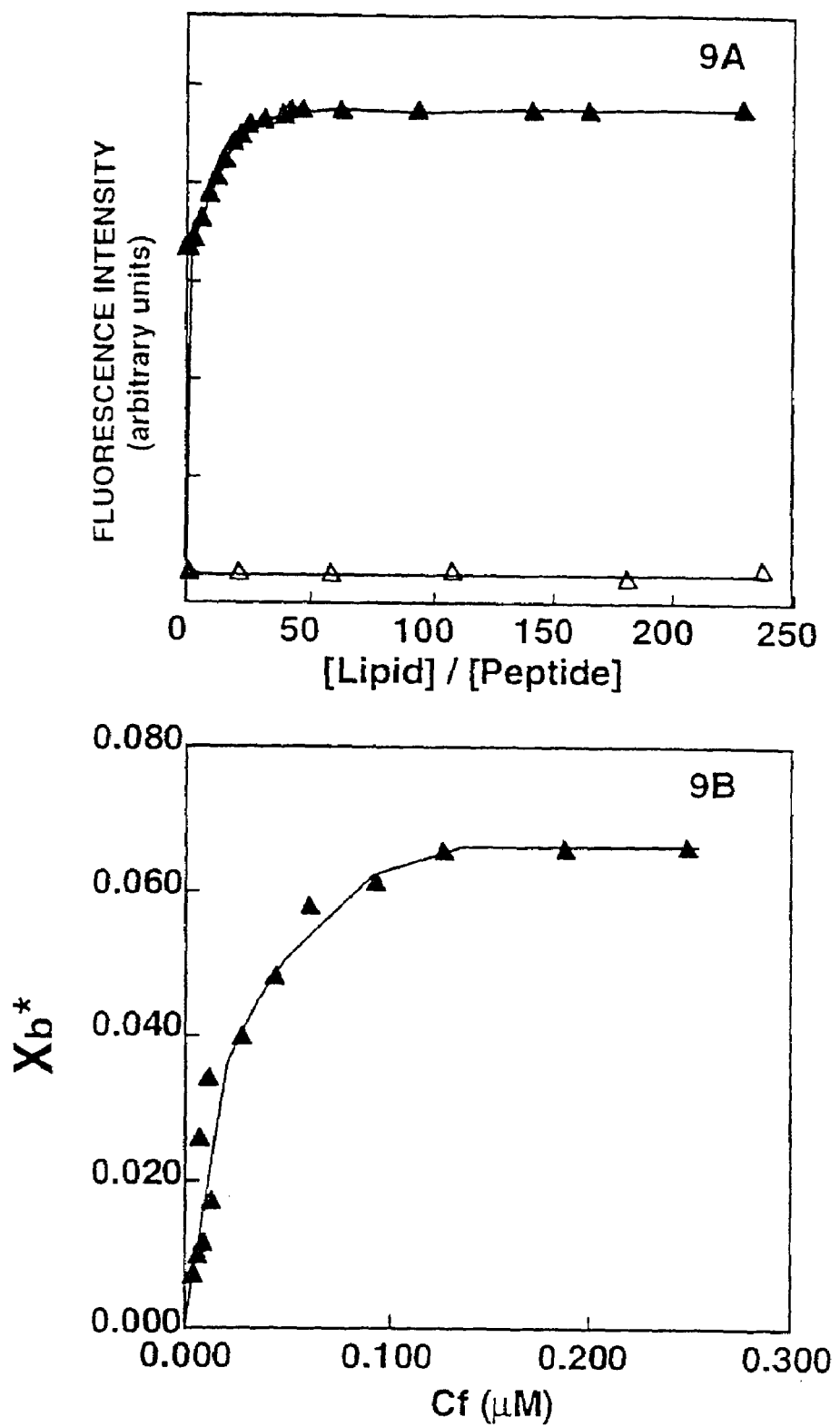
FIGS. 9A–B show increase in the fluorescence of [D]-V$^{5,8}$,I$^{17}$,K$^{21}$-melittin (0.5 µM total concentration) upon titration with PC/PS vesicles (filled triangles) or PC vesicles (empty triangles), with excitation wavelength set at 280 nm and emission at 340 nm. The experiment was performed at 25° C. in 50 mM Na$_2$SO$_4$, 25 mM HEPES-SO$_4^{-2}$ pH 6.8 (FIG. 9A); and binding isotherm derived from FIG. 9A by plotting X$_b$* (molar ratio of bound peptide per 60% of lipid) versus C$_f$ (equilibrium concentration of free peptide in the solution) (FIG. 9B).

2.5.2 Binding Studies. The inability of the diastereomer 18 to permeate PC vesicles may be due to its inability to bind to PC, or alternatively, it may bind to PC vesicles, but once bound cannot organize into structures that induce membrane leakage. In order to differentiate between the two possibilities, a binding study was conducted. The single Trp residue at position 19 of peptide 18 was used as an intrinsic fluorescence probe to follow its binding to PC and PC/PS vesicles. A fixed concentration (~0.5 μM) of the peptide was titrated with the desired vesicles (PC or PC/PS) and an increase in the fluorescence intensity was observed if binding occurred. Plotting of the resulting increases in the fluorescence intensities of Trp as a function of lipid:peptide molar ratios yielded conventional binding curves (FIG. 9A).

The binding curve of peptide 18 with PC/PS reveals that almost all the peptide molecules bound to the vesicles at a lipid:peptide molar ratio of 100:1. However, with PC vesicles a net increase in the fluorescence of the Trp was not observed even with the maximal lipid:peptide molar ratio tested, which indicated that the peptide does not bind to PC vesicles. Binding isotherms were constructed by plotting $X^*_b$ (the molar ratio of bound peptide per 60% of the total lipid) versus $C_f$ (the equilibrium concentration of the free peptide in the solution) (FIG. 5B). The surface partition coefficients were estimated by extrapolating the initial slopes of the curves to $C_f$ values of zero. The estimated surface partition coefficient, Kp*, of peptide 18 was $1.1 \pm 0.2 \times 10^4$ $M^{-1}$ (obtained from 4 measurements). This value is similar to the value reported for melittin binding to phosphatidylglycerol/phosphatidylcholine ($4.5 \pm 0.6 \times 10^4$ $M^{-1}$) (Beschiaschvili and Seelig, 1990).

The shape of the binding isotherm of a peptide can provide information on the organization of the peptide within membranes (Schwarz et al., 1987). The binding isotherm of peptide 18 bend downward indicating a negative cooperativity. A possible explanation for this negative cooperativity is that a low concentration, peptide 18 binding to PS/PC is enhanced by the negative charge of the phospholipid headgroups compared to the partition equilibrium with no charge effect. In addition, upon binding to the membrane the peptide partially neutralizes the negative membrane surface charge. However, once the membrane surface charge is neutralized, further peptide 18 binding is difficult, since repulsion of like charges becomes the dominant factor. Similar results were obtained in studies of melittin binding to negatively charged phospholipid membranes) (Batenburg et al., 1987; Beschiaschvili and Seelig, 1990). Interestingly, unlike melittin which binds strongly also to PC vesicles (Kuchinka and Seelig, 1989), peptide 18 did not bind to PC vesicles.

Figure 10:
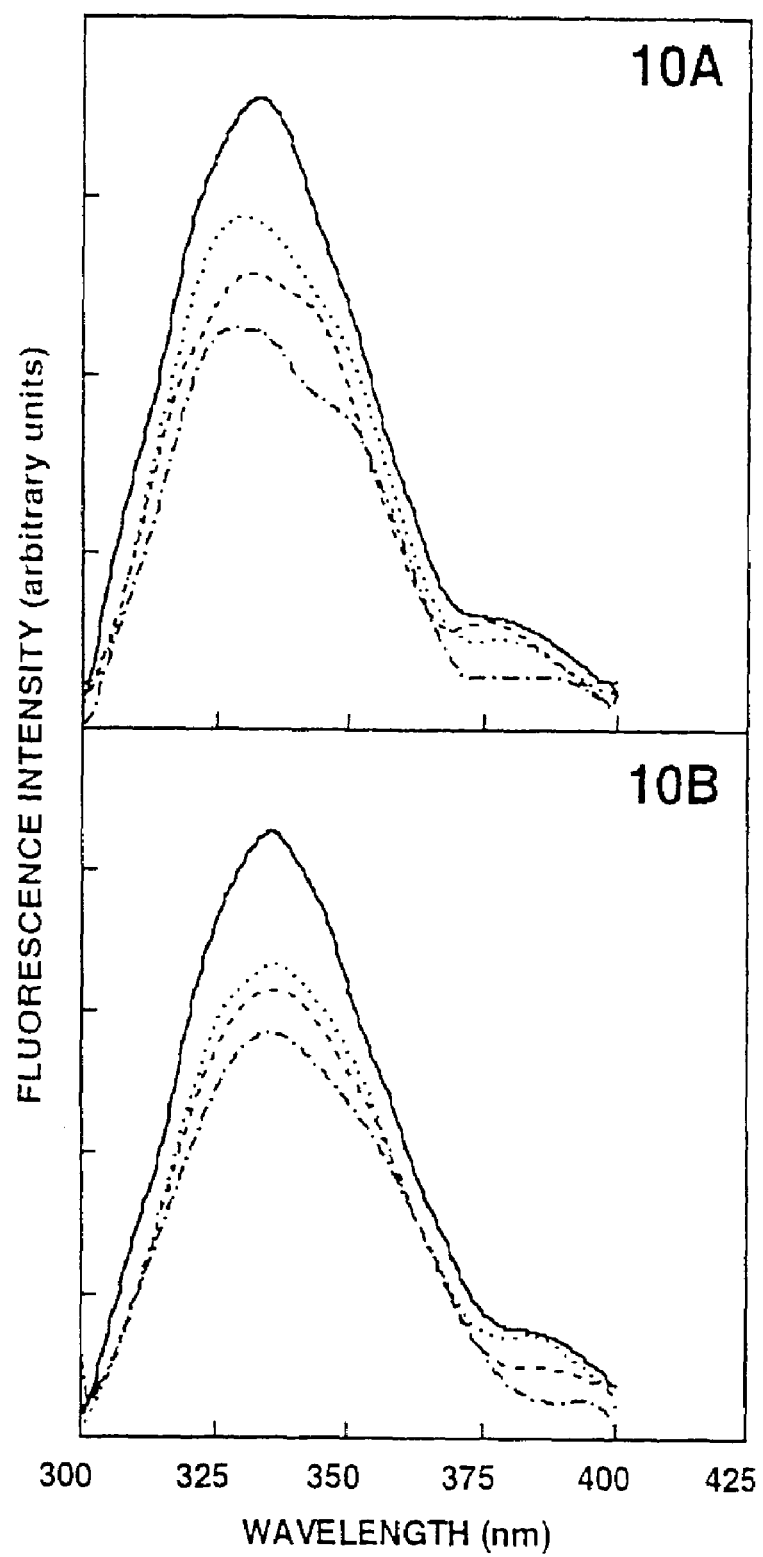
FIGS. 10A–B show quenching of the environmentally sensitive tryptophan by brominated phospholipids. Melittin (FIG. 10A) and [D]-V$^{5,8}$,I$^{17}$,K$^{21}$-melittin (10B) were added to buffer containing PC/PS (1:1 w/w) SUV. The SUV contained 25% of either 6,7 Br-PC (_·_·_·_), or 9,10 Br-PC (- - - - -), or 11,12 (Br-PC) (· · · · ·). After 2 min incubation, an emission spectrum of the tryptophan was recorded using spectrofluorometer with excitation set at 280 nm. For comparison PC/PS (1:1 w/w) SUV with no Br-PC were used (_).

2.6 Tryptophan Quenching Experiments. A tryptophan residue naturally present in the sequence of a protein or a peptide can serve as an intrinsic probe for the localization of the peptide within a membrane. Melittin contains a tryptophan residue at position 19, the N-terminal side of the C-helix. With both melittin and peptide 18, the largest quenching of tryptophan fluorescence was observed with 6,7-Br-PC/PS vesicles (FIG. 10). Less quenching was observed with 9,10-Br-PC/PS, and the least with 11,12-Br-PC/PS. These results indicate that upon binding to vesicles, the peptides were located near the head groups of the phospholipids.

EXAMPLE 3

Synthesis and Biological Activity of Model Lys/Leu Diastereomers 3.1 Lys/Leu diastereomers design. Six diastereomers of short linear model 12-mer peptides composed of varying ratios of lysine and leucine were synthesized in order (1) to examine whether a balance between hydrophobicity and a net positive charge may be a sufficient criteria necessary for selective bacterial lysis, and (2) to gain insight into the mechanism underlying this effect.

In the first series of model Lys/Leu 12-mer peptides 22–25, one third of their sequence was composed of D-amino acid residues. The location of the D-amino acids remained constant in all peptides which was constructed for maximum disruption of α-helical structure. D-amino acids were distributed along the peptide, leaving only very short stretches of 1–3 consecutive L-amino acids. The following peptides were synthesized:

22. $[D]-L^{3,4,8,10}-K_3L_9$ of the sequence: Lys-Leu-Leu-Leu-Leu-Leu-Lys-Leu-Leu-Leu-Leu-Lys-NH$_2$ (SEQ ID NO:22)
23. $[D]-L^{3,4,8,10}-K_4L_8$, of the sequence Lys-Leu-Leu-Leu-Lys-Leu-Leu-Leu-Lys-Leu-Leu-Lys-NH$_2$ (SEQ ID NO:23)
24. $[D]-L^{3,4,8,10}-K_5L_7$, of the sequence Lys-Leu-Leu-Leu-Lys-Leu-Lys-Leu-Lys-Leu-Leu-Lys-NH$_2$ (SEQ ID NO:24)
25. $[D]-L^{3,4,8,10}-K_7L_5$ of the sequence: Lys-Lys-Leu-Leu-Lys-Leu-Lys-Leu-Lys-Leu-Lys-Lys-NH$_2$ (SEQ ID NO:25)

In the second series of model Lys/Leu 12-mer peptides 26–27, two thirds of their sequence were composed of D-amino acid residues, at the exact positions of the L-amino acid residues of peptides 23 and 24 as follows:

26. $[D]-K^{1,5,9,12}L^{2,6,7,11}-K_4L_8$, of the sequence: Lys-Leu-Leu-Leu-Lys-Leu-Leu-Leu-Lys-Leu-Leu-Lys-NH$_2$ (SEQ ID NO:26)
27. $[D]-K^{1,5,7,9,12}L^{2,6,11}-K_5L_7$, of the sequence: Lys-Leu-Leu-Leu-Lys-Leu-Lys-Leu-Lys-Leu-Leu-Lys-NH$_2$ (SEQ ID NO:27)

In a third series of model Lys/Leu peptides, a 6-mer and a 8-mer diastereomers were synthesized (peptides 28 and 29, respectively):

28. $[D]-L^{2,4}-K_2L_4$, of the sequence: Lys-Leu-Leu-Leu-Lys (SEQ ID NO:28)
29. $[D]-L^{2,4,6}-K_3L_5$, of the sequence: Lys-Leu-Leu-Lys-Leu-Leu-Lys (SEQ ID NO:29)

Further Lys/Leu diastereomers according to the invention that were synthesized:

30. Lys Leu Leu Leu Lys Leu Lys Leu Lys LeuLeu Lys (SEQ ID NO:30)
31. Lys Leu LeuLeuLys Leu Lys Leu Lys Leu Leu Lys (SEQ ID NO:31)
32. Lys Leu Leu Leu Lys Leu Lys Leu Lys LeuLeu Lys (SEQ ID NO:32)

3.2 Synthesis of Lys/Leu diastereomers—The peptides were synthesized as described in Experimental Procedures, section (ii). The peptides were then characterized with regard to their structure, biological function and interaction with bacteria and model membranes composed of either zwitterionic or negatively charged phospholipids.

Figure 11:
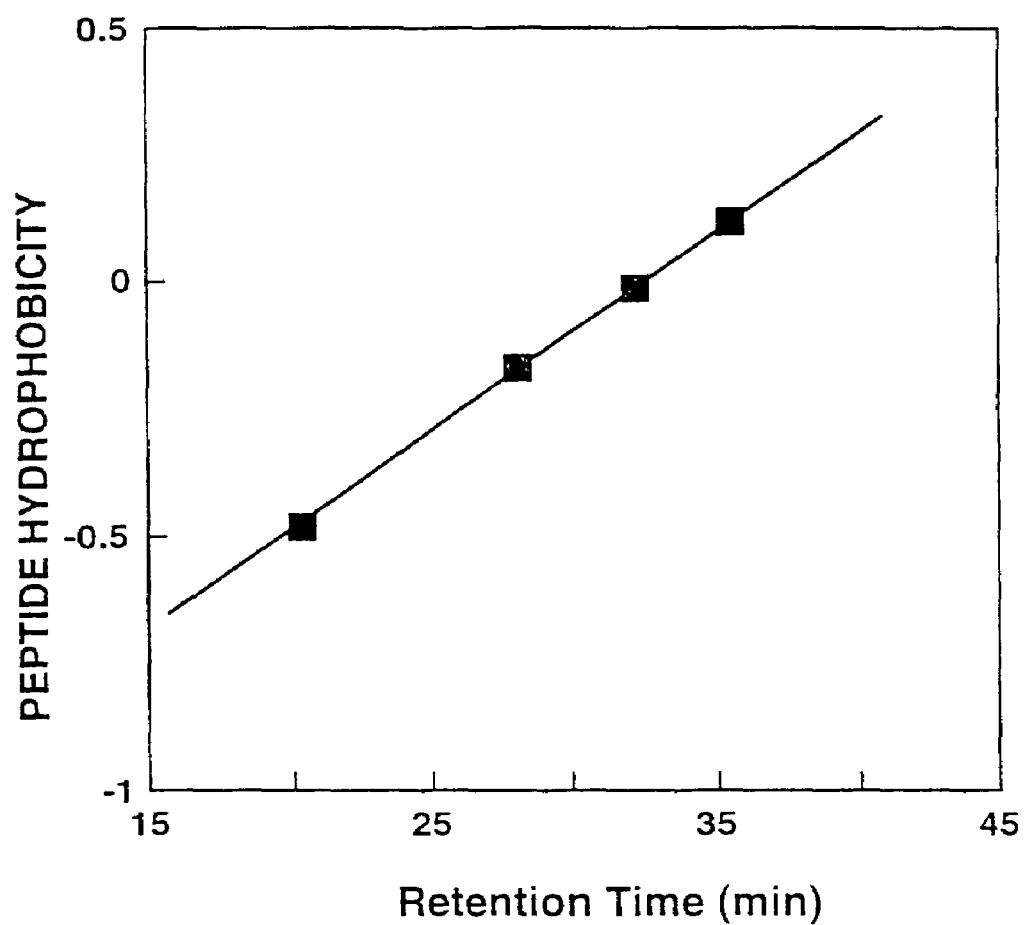
FIG. 11 shows the effect of the hydrophobicity of the Leu/Lys diastereomers on RP-HPLC retention time.

3.3 Hydrophobicity. The hydrophobicities and net positive charges of the peptides 22–25 are listed in Table 4. Mean values of hydrophobicity were calculated using consensus value of hydrophobicity scale (Eisenberg et al., 1984). As shown in FIG. 11, a direct correlation was found between hydrophobicity and the retention time of the peptides, suggesting that structure does not significantly contribute to overall hydrophobic interactions with the stationary phase.

TABLE 4

Hydrophobicity and net charge of the Leu/Lys diastereomers.

| Peptide Designation | Net Charge | Hydrophobicity |
| --- | --- | --- |
| 22. | +4 | 0.12 |
| 23. | +5 | −0.01 |
| 24. | +6 | −0.15 |
| 25. | +8 | −0.42 |

3.4 CD spectroscopy. The extent of the α-helical structure of the diastereomers 22–25 peptide was determined from their CD spectra in 40% TFE. As expected, after incorporation of D-amino acids, no signal was observed for all the diastereomers, demonstrating the lack of any specific secondary structure (data not shown). It is to be noted that in a recent study, a peptide with a sequence identical to that of peptide 23, but composed of only L-amino acids, was found to have about 40% α-helical structure in methanol and in DMPC vesicles (Cornut et al., 1994).

Figure 12:
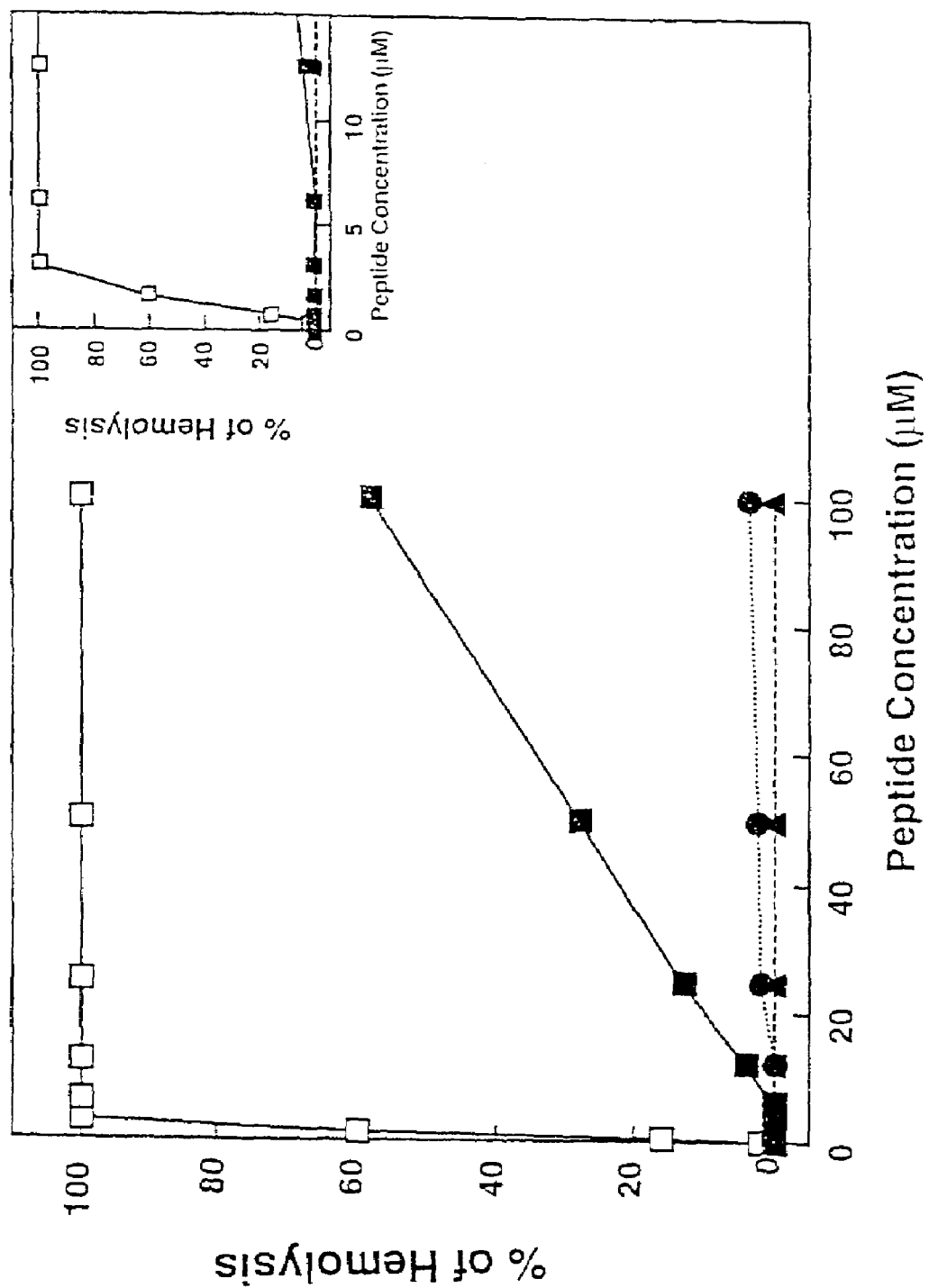
FIG. 12 shows dose-response curves of the hemolytic activity of the Leu/Lys diastereomers towards hRBC. The inset shows the assay results at low concentrations. Symbols: empty squares, melittin; filled squares, [D]-L$^{3,4,8,10}$-K$_3$L$_9$; filled circles, [D]-L$^{3,4,8,10}$-K$_4$L$_8$; empty triangles, [D]-L$^{3,4,8,10}$-K$_5$L$_7$; filled triangles, [D]-L$^{3,4,8,10}$-K$_7$L$_5$.

3.5 Antibacterial and hemolytic activity of the peptides 22–29. The hemolytic activity of the peptides 22–29 against hRBC was tested. A dose response curve for the hemolytic activity of the peptides 22–25 is shown in FIG. 12 wherein the hemolytic activity of melittin served as a control. A direct correlation was found between the hydrophobicity (Table 4) and the hemolytic activity of the diastereomers. Peptide 22, $[D]-L^{3,4,8,10}-K_3L_9$, which has the highest hydrophobicity, was the most hemolytic peptide. However, its hemolytic activity is very low in comparison to melittin (>60 fold less activity). All the other peptides showed no significant hemolytic activity up to the maximum concentration tested (100 μM). The hemolytic activity of peptides 22–29 is shown in Table 5. It should be noted that although peptide 23, $[D]-L^{3,4,8,10}-K_4L_8$, is not hemolytic at concentrations >100 fold of those required for significant hemolysis by melittin, its entirely L-amino acid form has been shown in a recent study to have hemolytic activity similar to that of melittin (~5 fold less) (Cornut et al., 1994).

The peptides 22–29 were also tested for their antibacterial activity against a representative set of bacteria, in which tetracycline, dermaseptin S, and melittin served as controls. The resultant MICs are shown in Table 5. The data show that the antibacterial activity of the diastereomers 22–29 was modulated by the balance between hydrophobicity and positively charged amino acids. Both the most hydrophobic peptide 22 and the most hydrophilic peptide 25 displayed the lowest range in antibacterial activity (Table 5). However, peptides 23 and 24 displayed high antibacterial activity against most of the bacteria tested with the former being slightly more potent. Furthermore, each peptide had a unique spectrum of antibacterial activity, and each was active more against Gram-positive as compared to Gram-negative bacteria.

3.6 Synergistic effects between tetracycline and the Lys/Leu diastereomers in serum. To investigate a possible synergistic relationship between the antibiotic tetracycline and the diastereomers, tetracycline was tested in 2-fold serial dilutions against *Pseudomonas aeruginosa* (ATCC 27853) in the presence of a constant equimolar concentration (1 μM)

of peptide 24, [D]-L$^{3,4,8,10}$-K$_5$L$_7$. Antibacterial activity of the mixtures was determined as described in Experimental procedures, section (xii).

A synergistic effect was observed between tetracycline and the diastereomer 24. Tetracycline shows little activity against *P. aeruginosa*. However, when mixed with 1 μM solution of peptide 24, a concentration which is 10 fold lower than that required for lytic activity against *P. aeruginosa*, an eight fold increase in the activity of tetracycline was observed (Table 6). A possible explanation for the synergistic effect is that the peptide slightly disrupts the bacterial wall which improves partitioning of tetracycline into the bacteria. This is supported by electron microscopy studies which show that below its MIC, peptide 24 causes morphological changes in the bacterial wall (FIG. 14). In addition, the effect of pooled human serum on the antibacterial activity of peptide 24 and the native antibacterial peptide dermaseptin against *P. aeruginosa* and *E. coli* was found to differ considerably (Table 6). While dermaseptin was 8–10 fold less active in the presence of serum, peptide 24 retained its antibacterial activity.

mimic the phospholipid composition of *E. coli* (Shaw, 1974). A direct correlation was found between the potential of the peptides to permeate model phospholipid membranes and their lytic activity against erythrocytes and *E. coli*. Only the hemolytic peptide 22 permeated the zwitterionic phospholipid vesicles. Furthermore, the ability of the peptides to permeate PE/PG vesicles correlates with the antibacterial activity of the peptides against *E. coli* (Table 5). Peptide 24, which has the lowest antibacterial activity, also had significantly decreased ability to permeate PE/PG vesicles compared to the other three peptides 22–24.

3.8 Electron microscopy study of bacterial lysis. The effect of the diastereomers 22–25 on the morphology of treated *E. coli* was visualized using transmission electron microscopy. All the peptides caused total lysis of the bacteria at the MIC (data not shown). However, when the peptides were utilized at concentrations corresponding to 80% of their MIC, some differences in the morphology of the treated bacteria were observed, depending upon the peptide used. The most hydrophobic peptide 22 caused the most damage

TABLE 5

Minimal Inhibitory Concentration (μM) of the peptides.

Minimal Inhibitory Concentration[a] (μM)

| Peptide Designation | E. Coli (D21) | A. calcoaceticus (Ac11) | P. aeruginosa (ATCC-27853) | B. megaterium (Bm11) | B. subtilis (ATCC-6051) | % Hemolysis at 100 μM |
|---|---|---|---|---|---|---|
| 22 | 9 | 20 | 125 | 0.7 | 1.1 | 58 |
| 23 | 3.5 | 4 | 10 | 0.4 | 0.5 | 0 |
| 24 | 7 | 20 | 10 | 0.25 | 2 | 0 |
| 25 | 80 | 200 | >200 | 1 | 100 | 0 |
| 26 | 4 | N.D | N.D | 0.5 | N.D | 0 |
| 27 | 7 | N.D | N.D | 0.2 | N.D | 0 |
| 28 | 200 | N.D | N.D | 50 | N.D | 0 |
| 29 | 3 | N.D | N.D | 3 | N.D | 0 |
| Dermaseptin S | 6 | 3 | 25 | 0.5 | 4 | — |
| Melittin | 5 | 2 | 25 | 0.3 | 0.6 | — |
| Tetracycline | 1.5 | 1.5 | 50 | 1.2 | 6.5 | — |

[a]Results are the mean of 3 independent experiments each performed in duplicates, with standard deviation of 20%

TABLE 6

Minimal Inhibitory Concentration (μM)[a] in the presence of human serum and synergistic activity of peptide 24

Minimal Inhibitory Concentration (μM)

| | P. aeruginosa (ATCC-27853) | | E. coli (D21) | |
|---|---|---|---|---|
| Peptide Designation | 0% Serum | 33% Serum | 0% Serum | 33% Serum |
| 24 | 10 | 10 | 7 | 7 |
| Dermaseptin S | 25 | 200 | 6 | 50 |
| Tc[b] | 50 | | | |
| Tc + 24 (1 μM) | 6 | | | |

Figure 13:
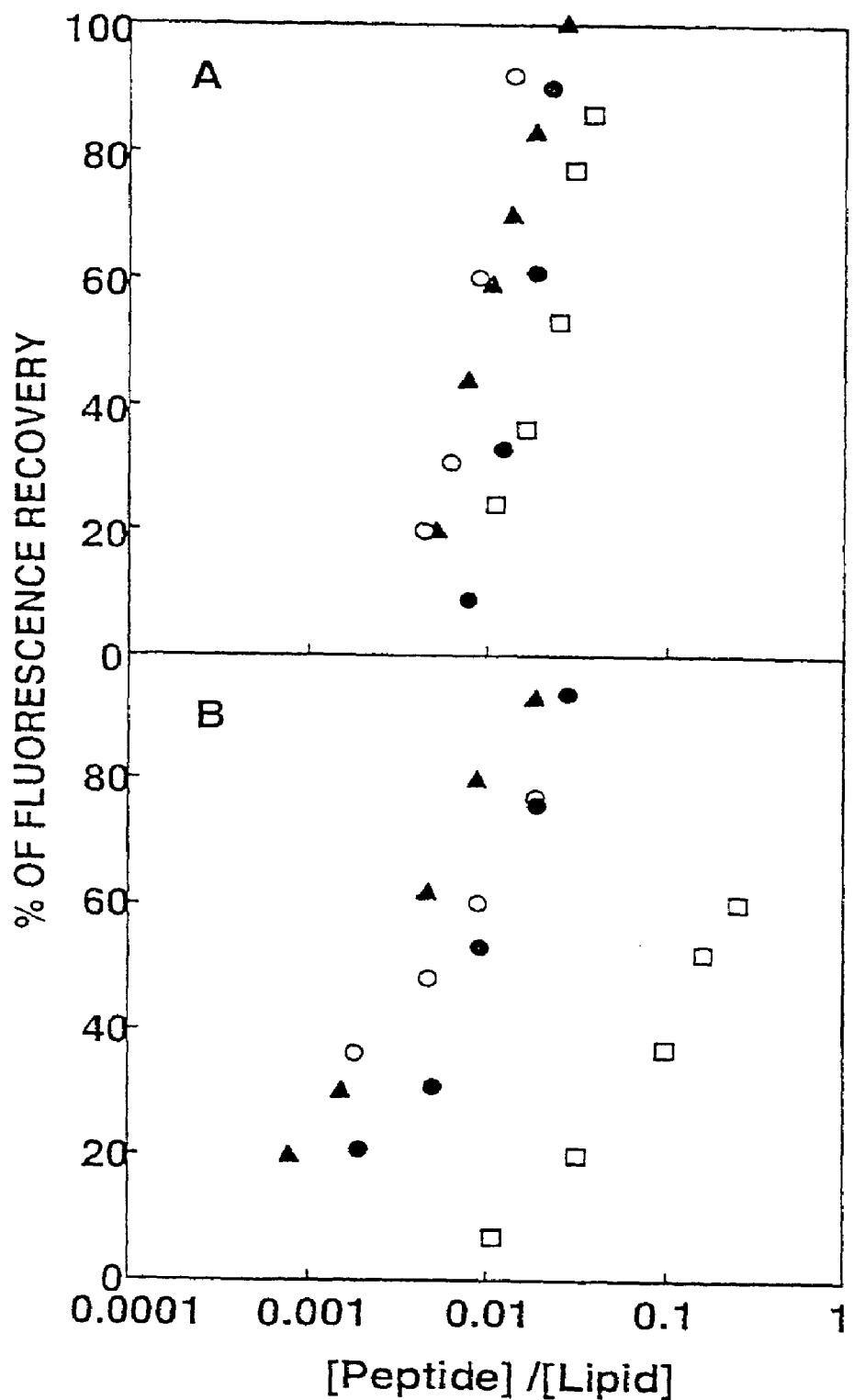
FIGS. 13A–B show maximal dissipation of the diffusion potential in vesicles, induced by the Leu/Lys diastereomers. The peptides were added to isotonic K$^+$ free buffer containing SUV composed of PC (FIG. 13A) or PE/PG (13B); pre-equilibrated with the fluorescent dye diS-C$_2$-5 and valinomycin. Fluorescence recovery was measured 3–10 min after the peptides were mixed with the vesicles. Symbols: filled squares, [D]-L$^{3,4,8,10}$-K$_3$L$_9$; filled circles, [D]-L$^{3,4,8,10}$-K$_4$L$_8$; filled triangles, [D]-L$^{3,4,8,10}$-K$_5$L$_7$; crossed circles, [D]-L$^{3,4,8,10}$-K$_7$L$_5$.

[a]Results are the mean of 2 independent experiments each performed in duplicates, with standard deviation of 20%.
[b]Tc - Tetracycline 3.7 Peptide-induced membrane permeation. Various concentrations of peptides were mixed with vesicles that had been pretreated with the fluorescent dye, diS-C$_2$-5, and valinomycin. The kinetics of the fluorescence recovery was monitored and the maximum fluorescence level was determined as a function of peptide concentration (FIG. 13). PC/cholesterol vesicles (10:1) served as a model of the phospholipid composition of the outer erythrocyte leaflet (Verkleij et al., 1973), and PE/PG vesicles (7:3) was used to to the cell wall and membranes, while the least hydrophobic peptide 25 only caused local perturbations (FIG. 14).

EXAMPLE 4

Synthesis and Biological Activity of Model Lys/Ala and Lys/Val Diastereomers 4.1 Diastereomer design. To further examine whether modulating hydrophobicity and the net positive charge of linear cytotoxic peptides is sufficient to confer selective antibacterial activity, two further model 12-mer peptides 33 and 34–37, composed of Lys/Ala or Lys/Val residues, respectively, with at least one third of their sequences being of D-Ala or D-Val residues, were synthesized:

33. [D]-A$^{3,4,8,10}$-K$_4$A$_8$ of the sequence: Lys-Ala-Ala-Ala-Lys-Ala-Ala-Ala-Lys-Ala-Ala-Lys-NH$_2$ (SEQ ID NO:33)

34. [D]-V$^{3,4,8,10}$-K$_4$V$_8$ of the sequence: Lys-Val-Val-Val-Lys-Val-Val-Val-Lys-Val-Val-Lys-NH$_2$ (SEQ ID NO:34)

35. Lys Val Val Val Lys Val Lys Val Lys Val Val Lys (SEQ ID NO:35)

36. Lys Val Val Val Lys Val Lys Val Lys Val Val Lys (SEQ ID NO:36)

37. Lys Val Val Val Lys Val Lys Val Lys Val Val Lys (SEQ ID NO: 37)

4.2 Synthesis. The Lys/Ala and Lys/Val diastereomers were synthesized as described in Experimental Procedures, section (ii).

4.3 Antibacterial and hemolytic activity. Peptides 33 and 34 were tested against *E. coli* and *B. megaterium* and hRBC. The results in Table 7 show that both model diastereomers are antibacterial and non-hemolytic:

TABLE 7

Minimal Inhibitory Concentration (μM) and hemolytic activity of the peptides 28 and 29

| Peptide Designation | Minimal Inhibitory Concentration (μM) | | % hemolysis at 100 μM |
|---|---|---|---|
| | *E. coli* (D21) | *B. megaterium* (Bm11) | |
| 33 | 12 | 1 | 0 |
| 34 | 3.5 | 0.8 | 0 |

EXAMPLE 5

Synthesis of Further Model Diastereomers

The following model diastereomers according to the invention composed of sequences of 6, 8, 12, 14, 16, 19, 25, 26 and 30 residues of two, three or more different amino acids, were synthesized:

38. Lys Leu Ile Leu Lys Leu (SEQ ID NO: 38)
39. Lys Val Leu His Leu Leu (SEQ ID NO:39)
40. Leu Lys Leu Arg Leu Leu (SEQ ID NO: 40)
41. Lys Pro Leu His Leu Leu (SEQ ID NO:41)
42. Lys Leu IleLeu Lys Leu Val Arg (SEQ ID NO: 42)
43. Lys Val Phe HisLeu Leu His Leu (SEQ ID NO: 43)
44. His Lys Phe Arg Ile LeuLys Leu (SEQ ID NO: 44)
45. Lys Pro Phe His Ile Leu His Leu (SEQ ID NO:45)
46. LysIle Ile Ile Lys Ile Lys Ile Lys Ile Ile Lys (SEQ ID NO:46)
47. Lys Ile IleIle Lys Ile Lys Ile Lys Ile Ile Lys (SEQ ID NO: 47)
48. Lys Ile Ile Ile Lys Ile Lys Ile Lys Ile Ile Lys (SEQ ID NO: 48)
49. Lys Ile Pro Ile Lys Ile Lys Ile Lys Ile Pro Lys (SEQ ID NO: 49)
50. Lys Ile Pro Ile Lys Ile Lys Ile Lys Ile Val Lys (SEQ ID NO:50)
51. Arg Ile Ile Ile Arg Ile Arg Ile Arg Ile Ile Arg (SEQ ID NO:51)
52. Arg Ile IleIle Arg IleArgIle Arg Ile Ile Arg (SEQ ID NO:52)
53. Arg Ile Ile Ile Arg Ile Arg Ile Arg Ile Ile Arg (SEQ ID NO:53)
54. Arg Ile Val Ile Arg Ile Arg Ile Arg Leu Ile Arg (SEQ ID NO:54)
55. Arg Ile IleVal Arg Ile Arg Leu Arg Ile Ile Arg (SEQ ID NO:55)
56. Arg Ile Gly Ile Arg Leu Arg Val Arg Ile Ile Arg (SEQ ID NO:56)
57. Lys Ile Val Ile Arg Ile Arg Ile Arg Leu Ile Arg (SEQ ID NO:57)
58. Arg Ile AlaVal Lys Trp Arg Leu Arg Phe Ile Lys (SEQ ID NO:58)
59. Lys Ile Gly Trp Lys Leu Arg Val Arg Ile Ile Arg (SEQ ID NO:59)
60. Lys Lys Ile Gly Trp Leu Ile Ile Arg Val Arg Arg (SEQ ID NO:60)
61. Arg Ile Val Ile Arg Ile Arg Ile Arg Leu Ile Arg Ile Arg (SEQ ID NO:61)
62. Arg Ile IleVal Arg Ile Arg Leu Arg Ile Ile Arg Val Arg (SEQ ID NO:62)
63. Arg Ile Gly Ile Arg Leu Arg Val Arg Ile Ile Arg Arg Val (SEQ ID NO:63)
64. Lys Ile Val Ile Arg Ile Arg Ala Arg Leu Ile Arg Ile Arg Ile Arg (SEQ ID NO:64)
65. Arg Ile IleVal Lys Ile Arg Leu Arg Ile Ile Lys LysIle Arg Leu (SEQ ID NO:65)
66. Lys Ile Gly Ile Lys Ala Arg Val Arg Ile Ile Arg Val Lys Ile Ile (SEQ ID NO:66)
67. Arg Ile IleVal His Ile Arg Leu Arg Ile Ile His HisIle Arg Leu (SEQ ID NO:67)
68. His Ile Gly Ile Lys Ala His Val Arg Ile Ile Arg Val His Ile Ile (SEQ ID NO:68)
69. Arg Ile Tyr Val Lys Ile His Leu Arg Tyr Ile Lys LysIle Arg Leu (SEQ ID NO:69)
70. Lys Ile Gly His Lys Ala Arg Val His Ile Ile Arg Tyr Lys Ile Ile (SEQ ID NO:70)
71. Arg Ile TyrVal Lys Pro His Pro Arg Tyr Ile Lys LysIle Arg Leu (SEQ ID NO: 71)
72. Lys Pro Gly His Lys Ala Arg Pro His Ile Ile Arg Tyr Lys Ile Ile (SEQ ID NO: 72)
73. Lys Ile Val Ile Arg Ile Arg Ile Arg Leu Ile Arg Ile Arg Ile Arg Lys Ile Val (SEQ ID NO: 73)
74. Arg Ile IleVal Lys IleArg Leu Arg Ile Ile Lys LysIle Arg LeuIle Lys Lys (SEQ ID NO: 74)
75. Lys Ile Gly TrpLys Leu Arg Val Arg Ile Ile Arg Val Lys Ile GlyArg Leu Arg (SEQ ID NO: 75)
76. Lys Ile Val Ile Arg Ile Arg Ile Arg Leu Ile Arg Ile Arg Ile Arg Lys Ile Val Lys Val Lys Arg Ile Arg (SEQ ID NO:76)
77. Arg Phe AlaVal Lys IleArg Leu Arg Ile Ile Lys LysIle Arg LeuIle Lys LysIle Arg Lys Arg Val Ile Lys (SEQ ID NO:77)
78. Lys Ala Gly TrpLys Leu Arg Val Arg Ile Ile Arg Val Lys Ile GlyArg Leu Arg Lys Ile Gly TrpLys Lys Arg Val Arg Ile Lys (SEQ ID NO: 78)
79. Arg Ile TyrVal Lys Pro His Pro Arg Tyr Ile Lys LysIle Arg Leu (SEQ ID NO: 79)
80. Lys ProGly His Lys Ala ArgProHisIleIle Arg Tyr Lys Ile Ile (SEQ ID NO: 80)
81. Lys Ile Val IleArgIle Arg Ile Arg LeuIleArgIle Arg Ile Arg Lys Ile Val (SEQ ID NO:81)
82. Arg Ile IleVal Lys IleArg Leu ArgIle Ile Lys LysIle Arg LeuIle Lys Lys (SEQ ID NO: 82)
83. Arg Ile TyrVal Ser Lys Ile Ser Ile Tyr Ile Lys LysIle Arg Leu (SEQ ID NO: 83)
84. Lys Ile Val IlePheThr Arg Ile Arg LeuThrSerIle Arg Ile Arg Ser Ile Val (SEQ ID NO: 84)
85. Lys ProIle His Lys Ala ArgProThrIleIle Arg Tyr Lys Met Ile (SEQ ID NO: 85)

EXAMPLE 6

Synthesis and Biological Activity of Cyclic Diastereomers 6.1 Design. The following cyclic derivatives of diastereomers of pardaxin fragments with cysteine residues at both the N- and C-termini were synthesized:

86. Cyclic K$^1$[D]P$^7$L$^{18}$L$^{19}$[1-22]-par of the sequence: Cys-Lys-Gly-Phe-Phe-Ala-Leu-Ile- Pro-Lys-Ile-Ile-Ser-Ser-Pro-Leu-Phe-Lys-Thr-Leu-Leu-Ser-Ala-Val-Cys (SEQ ID NO: 86)

87. Cyclic K$^1$K$^2$[D]P$^7$L$^{18}$L$^{19}$[1-22]-par of the sequence: Cys-Lys-Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val-Cys (SEQ ID NO: 87)

88. Cyclic K$^1$K$^2$K$^3$[D]P$^7$L$^{18}$L$^{19}$[1-22]-par of the sequence: Cys-Lys-Lys-Lys-Gly-Phe-Phe-Ala-Leu-Ile-Pro-Lys-Ile-Ile-Ser-Ser-Pro-Leu-Phe-Lys-Thr-Leu-Leu-Ser-Ala-Val-Cys (SEQ ID NO: 88)

The following cyclic derivatives of diastereomers of different amino acid residues with cysteine residues at both the N- and C-termini were synthesized:

89. Cyclic Cys Arg Ile Val Ile Arg Ile Arg Ile Arg Leu Ile Arg Ile Arg Cys (SEQ ID NO: 89)

90. Cyclic Cys Lys ProGly His Lys Ala ArgProHisIleIle Arg Tyr Lys Ile Ile Cys (SEQ ID NO:90)

91. Cyclic Cys Arg Phe AlaVal Lys IleArg Leu Arg Ile Ile Lys LysIle Arg LeuIle Lys LysIleArg Lys Arg Val Ile Lys Cys (SEQ ID NO: 91)

92. Cyclic Cys Lys Leu Leu Leu Lys Leu Leu Leu Lys Leu Leu Lys Cys (SEQ ID NO:92)

93. Cyclic Cys Lys Leu Leu Leu Lys Leu Lys Leu Lys Leu Leu Lys Cys (SEQ ID NO:93)

The following cyclic derivatives of diastereomers of different amino acid residues without cysteine residues at both the N- and C-termini were synthesized:

94. HN-Lys Leu Leu Leu Lys Leu Leu Leu Lys Leu Leu Lys-CO (SEQ ID NO:94)

95. HN-Lys Leu Leu Leu Lys Leu Lys Leu Lys Leu Leu Lys-CO (SEQ ID NO:95)

6.2 Synthesis of the cyclic diastereomers. The cyclic peptides were synthesized by a solid-phase method as described in Experimental Procedures, section (ii), without or with cysteine residues at both the N and C-termini of the peptides. The cyclization without cystein was carried out by protecting the N-terminal, activating the C-terminal, deprotection of the N-terminal and reaction of the C- and N-terminal groups while still bound to the resin. After HF cleavage and RP-HPLC purification the peptides were solubilized at low concentration in PBS (pH 7.3), and cyclization was completed after 12 h. The cyclic peptides were further purified on RP-HPLC and subjected to amino acid analysis to confirm their composition, and SDS-PAGE to confirm their monomeric state.

6.3 Antibacterial and hemolytic activity. Peptides 86–88 were tested against *E. coli* and *B. megaterium* and hRBC. The results in Table 8 show that all three cyclic pardaxin-derived diastereomers are antibacterial and non-hemolytic:

TABLE 8

Minimal Inhibitory Concentration (μM) and hemolytic activity of the cyclic pardaxin-derived diastereomers.

| Peptide Designation | Minimal Inhibitory Concentration (μM) | | % hemolysis at 100 μM |
|---|---|---|---|
| | E. coli (D21) | B. megaterium (Bm11) | |
| 86 | 30 | 10 | 0 |
| 87 | 15 | 6 | 0 |
| 88 | 7.5 | 2 | 0 |

6.4 Antibacterial and hemolytic activity. Peptides 92–95 were tested against *E. coli*, *B. subtilis* and *P. aeruginosa*. The results in Table 8a show that all four cyclic diastereomers are antibacterial and non-hemolytic:

TABLE 8a

Minimal Inhibitory Concentration (μM) and hemolytic activity of the cyclic diastereomers.

| Peptide Designation | Minimal Inhibitory Concentration (μM) | | | % hemolysis at 50 μM |
|---|---|---|---|---|
| | E. coli | B. subtilis | P. aeruginosa | |
| 92 | 12.5 | 1.2 | 25 | 0 |
| 93 | 15 | 5 | 25 | 0 |
| 94 | 12.5 | 1.5 | 30 | 0 |
| 95 | 15 | 6 | 20 | 0 |

EXAMPLE 7

Synthesis and Biological Activity of Bundled Lys/Leu Peptide Diastereomers.

7.1 Design. Using as template peptide 23 and as monomers peptide 23 or 24 with an additional cysteine residue at the C-terminus (23C and 24C, respectively, the following bundle-sequences were produced:

96. ([D]-L$^{3,4,8,10}$-K$_4$L$_8$C)$_5$ [D]-L$^{3,4,8,10}$-K$_4$L$_8$ of the sequence: (Lys-Leu-Leu-Leu-Lys-Leu-Leu-Leu- Lys-Leu-Leu-Lys-Cys-NH$_2$)$_5$ Lys-Leu-Leu-Leu-Lys-Leu-Leu-Leu-Lys-Leu-Leu-Lys-NH$_2$ (SEQ ID NOS:96and 23)

97. ([D]-L$^{3,4,8,10}$-K$_5$L$_7$C)$_5$ [D]-L$^{3,4,8,10}$-K$_4$L$_9$ of the sequence: (Lys-Leu-Leu-Leu-Lys-Leu-Lys-Leu- Lys-Leu-Leu-Lys-Cys-NH$_2$)$_5$ Lys-Leu-Leu-Leu-Lys-Leu-Lys-Leu-Lys-Leu-Leu-Lys-NH$_2$ (SEQ ID NOS:97and 24)

7.2 Synthesis. In order to produce template-bound diastereomers, 1:1 molar ratio of DCC and bromoacetic acid were allowed to react in DMSO at 25° C. for 1 h. The template (peptide 23) was added to the reaction mixture and left under agitation for 12 h after which the DMSO was lyophilized. The remaining bromoacetic acid was extracted with dry ether. The template was then reacted with excess of diastereomers 23C and 24C with cysteine residue at their C-terminus, in PBS pH 7.3 at 25° C. for 1 h. The template-bound diastereomers 96 and 97 were further purified on RP-HPLC, and examined on SDS-PAGE to confirm their aggregation state.

7.3 Antibacterial and hemolytic activity. The template-bound diastereomers diastereomers 96 and 97 were tested against *E. coli* and *B. megaterium* and hRBC. The results in Table 9 show that both bundle sequences are antibacterial and non-hemolytic.

TABLE 9

Minimal Inhibitory Concentration (μM) and hemolytic activity of the bundles.

| Peptide Designation | Minimal Inhibitory Concentration (μM) | | % hemolysis at 100 μM |
|---|---|---|---|
| | E. coli (D21) | B. megaterium (Bm11) | |
| 96 | 0.2 | 0.05 | 0 |
| 97 | 0.1 | 0.02 | 0 |

EXAMPLE 8

Synthesis and Biological Activity of Mixtures of Lys/Leu 12-mer Peptide Diastereomers Peptides are synthesized by a solid phase method as described in Experimental Procedures, section (ii) above. At each coupling step a mixture composed of 1 eq each of lysine, leucine and D-leucine was added to the reaction. The synthesis resulted in a mixture of $3^{12}$ different peptides. After HF cleavage the peptides were extracted with double distilled water (ddw) and lyophilized.

The mixture of the Lys/Leu 12-mer peptide diastereomers was tested against *E. coli* D21 (MIC: 15 µg/ml) and *B. megaterium* Bm11 D21 (MIC: 3 µg/ml) and hRBC (0% hemolysis at 100 µM). As expected, the mixture had antibacterial activity but was non-hemolytic.

EXAMPLE 9

Synthesis and Biological Activity of Lys/Leu/D-Leu Random Copolymers

In order to produce diastereomers of polymers of different sizes, excess of N-carboxyanhydride residues over initiator free amino acids were allowed to polymerize in DMF at 25° C. for 4 h (Katchalski and Sela, 1958). Polymers consisting of different ratios of lysine, leucine and D-leucine were produced using different ratios of lysine-N-carboxyanhydride, leucine-N-carboxyanhydride and D-leucine-N-carboxy anhydride. Three of such polymers and their antibacterial and hemolytic activity are shown in Table 10.

TABLE 10

Minimal Inhibitory Concentration (µM) and hemolytic activity of the Lys/Leu/D-Leu copolymers.
Minimal Inhibitory Concentration (µg/ml)

| Amino Acids Ratio (Molar) Lys:Leu:[D]-Leu | E. coli (D21) | megaterium (Bm11) | % hemolysis at 100 µM |
|---|---|---|---|
| 1:1:1 | 90 | 15 | 0 |
| 2:1:1 | 35 | 8 | 0 |
| 3:1:1 | 80 | 20 | 0 |

EXAMPLE 10

Antifungal Activity of the Diastereomers

The antifungal activity of the pardaxin-derived peptides 1 and 16 (see Example 1 above) was examined in sterile 96-well plates (Nunc F96 microtiter plates) in a final volume of 100 µL as follows: Fifty microliters of a suspension containing fungi at concentration of 1×10⁶ Colony-Forming Units (CFU)/ml in culture medium (Sabouraud's glucose broth medium) was added to 50 µL of water containing the peptide in serial 2-fold dilutions in water. Inhibition of growth was determined by measuring the absorbance at 492 nm with a Microplate autoreader E1309 (Bio-tek Instruments), after an incubation time of 48 h at 30° C. Antifungal activities were expressed as the minimal inhibitory concentration (MIC), the concentration at which 100% inhibition of growth was observed after 48 h of incubation. The fungi used were: *Candida albicans* (IP886-65) and *Cryptococcus neoformans* (IP960-67). As shown in Table 11, both peptides 1 and 16 showed antifungal activity.

TABLE 11

Minimal Inhibitory Concentration (µM) of the diastereomers 1 and 16 against fungi.
Minimal Inhibitory Concentration (µM)

| Peptide Designation | Candida albicans (IP886-65) | Cryptococcusneoformans (IP960-67) |
|---|---|---|
| 1 | 35 | 50 |
| 16 | 120 | 150 |

EXAMPLE 11

Anticancer Activity of the Diastereomers

The anticancer activity of the Lys/Leu diastereomers 23 and 24 (see Example 3 above) was examined against mouse adenocarcinomas. Cells were seeded at 5–10 000/well in 96-well microtiter plates in Dulbecco's modified Eagle's medium. After the cells had attached, 20 µl of diluted peptide solution in normal saline were transfected to the well to give final concentrations ranging from 20 to 150 µM. Following 1 h incubation with the peptides, the viability of the cancer cell was measured by Trypan blue (0.1% w/v) vital staining assay. In control experiments the peptide solvent alone was added to the cells. Anticancer activities were expressed as the minimal inhibitory concentration (MIC), the concentration at which 100% inhibition of growth was observed after 1 h of incubation. The results in Table 12 show that both peptides are active against malignant cells.

TABLE 12

Minimal Inhibitory Concentration (µM) of the diastereomers against mouse adenocarcinoma.
Minimal Inhibitory Concentration (µM)

| Peptide Designation | mouse adenocarcinoma |
|---|---|
| 23 | 50 |
| 24 | 80 |

EXAMPLE 12

Activity of the Diastereomers Against *Leishmania mexicana*

The melittin-derived diastereomer peptide 20 (see Example 2 above) and the Leu/Lys diastereomer peptide 23 (see Example 3 above) were tested against *Leishmania*. Promastigotes of the *Leishmania mexicana* NR strain to be assayed were cultured at 27° C. in RPMI 1640 medium supplemented with 10% fetal bovine serum. Parasite were harvested by centrifugation at 1200×g for 10 min at 4° C. and washed twice with PBS (50 mM sodium phosphate, 150 mM NaCl, pH 7). The washed promastigotes were counted in a hemocytometer and adjusted to 1×10⁶ parasites/ml. Aliquotes of this suspension were assayed in a final volume of 100 µl by counting living (motile) cells after 24 h of incubation at 26° C. in the absence or presence of various concentrations of the diastereomers. Anti-*Leishmania* activities were expressed as the minimal inhibitory concentration (MIC), the concentration at which 100% death was observed after 24 h of incubation. It was found that for peptide 23 the MIC is 17 µM and for peptide 20 the MIC is 32 µM.

EXAMPLE 13

Antiviral Activity of the Diastereomer 23

Sendai virus (Z strain) was grown in the allantoic sac of 10–11 day old embryonated chicken eggs, harvested 48 h after injection and purified. The virus was resuspended in buffer composed of 160 mM NaCl, 20 mM tricine, pH 7.4, and stored at −70° C. Virus haemagglutinating activity was measured in haemagglutinating units (HAU). One microliter contained ~60000 HAU. Fresh human blood was obtained from a blood bank and stored for up to 1 month at 4° C. Prior to use, erythrocytes were washed twice with PBS pH 7.2, and diluted to the desired concentration (% v/v) with the same buffer. Virions, erythrocytes and peptides were mixed in different orders of addition and various amounts. The final incubation was always at 37° C. for 60 min. followed by centrifugation at 5700 g for 10 min to remove intact cells. In all cases duplicate samples were used and two aliquots were taken from the supernatant of each sample to two wells of a 96-well plate. The amount of hemoglobin release was monitored by measuring the absorbance of the wells with the ELISA, plate reader at 540 nm. Antiviral activity was expressed as the minimal inhibitory concentration (MIC), the concentration at which no release of hemoglobin was observed after incubation. It was found that for the Lys/Leu diastereomer peptide 23 the MIC is 80 μM.

REFERENCES

1. Agawa, Y., Less, S., Ono, S., Aoyagi, H., Ohno, M., Taniguchi, T., Anzai, K., and Kirino, Y. 1991. *J. Biol. Chem.* 266: 20218–20222.
2. Altenbach, C., and Hubbell, W. L. 1988. The aggregation state of spin-labeled melittin in solution and bound to phospholipid membranes: evidence that membrane-bound melittin is monomeric. *Proteins.* 3: 230–242.
3. Anderson, D., Terwilliger, T. C., Wickner, W., and Eisenberg, D. 1980. Melittin forms crystals which are suitable for high resolution X-ray structural analysis and which reveal a molecular 2-fold axis of symmetry. *J. Biol. Chem.* 255: 2578–2582.
4. Anzai, K., Hamasuna, M., Kadono, H., Lee, S., Aoyagi, H., and Kirino, Y. 1991. *Biochem. Biophys. Acta.* 1064: 256–266.
5. Bartlett, G. R. 1959. Phosphorus assay in column chromatography, *J. Biol. Chem.* 234: 466–468.
6. Batenburg, A. M., Hibbeln, J. C., and de, K. B. 1987. Lipid specific penetration of melittin into phospholipid model membranes. *Biochim. Biophys. Acta.* 903: 155–165.
7. Batenburg, A. M., van, E. J., and de, K. B. 1988. Melittin-induced changes of the macroscopic structure of phosphatidylethanolamines. *Biochemistry.* 27: 2324–2331.
8. Batenburg, A. M., van, E. J., Leunissen, B. J., Verkleij, A. J., and de, K. B. 1987. Interaction of melittin with negatively charged phospholipids: consequences for lipid organization. *Febs Lett.* 223: 148–154.
9. Bazzo, R., Tappin, M. J., Pastore, A., Harvey, T. S., Carver, J. A., and Campbell, I. D. 1988. The structure of melittin. A 1H-NMR study in methanol. *Eur. J. Biochem.* 173: 139–146.
10. Benkirane, N., Friede, M., Guichard, G., Briand, J. P., Van, R. M., and Muller, S. 1993. *J. Biol. Chem.* 268: 26279–26285.
11. Beschiaschvili, G., and Seelig, J. 1990. Melittin binding to mixed phosphatidylglycerol/phosphatidylcholine membranes. *Biochemistry.* 29: 52–58.
12. Bessalle, R., Kapitkovsky, A., Goria, A., Shalit, I. and Fridkin, M. 1990. *Febs Lett.* 274: 151–155.
13. Bolen, E. J., and Holloway, P. W. 1990. Quenching of tryptophan fluorescence by brominated phospholipid. *Biochemistry.* 29: 9638–9643.
14. Boman, H. G. 1995. Peptide antibiotics and their role in innate immunity. *Annu. Rev. Immun.* 13: 61–92.
15. Chen, H. C., Brown, J. H., Morell, J. L., and Huang, C. M. 1988. Synthetic magainin analogues with improved antimicrobial activity. *Febs Lett.* 236: 462–466.
16. Cornut, I., Buttner, K., Dasseux, J. L., and Dufourcq, J. 1994. The amphipathic alpha-helix concept. Application to the de novo design of ideally amphipathic Leu, Lys peptides with hemolytic activity higher than that of melittin. *Febs Lett.* 349: 29–33.
17. Dempsey, C. E. 1990. The actions of melittin on membranes. *Biochim. Biophys. Acta.* 1031: 143–161.
18. Dhople, V. M., and Nagaraj, R. 1993. d-toxin, unlike melittin, has only hemolytic activity and no antimicrobial activity: rationalization of this specific biological activity. *Biosci. Rep.* 13: 245–250.
19. Eisenberg, D., Schwarz, E., Kornaromy, M., and Wall, R. 1984. Analysis of membrane and surface protein sequences with the hydrophobic moment plot. *J. Mol. Biol.* 179: 125–142.
20. Fisher, P. J., Prendergast, F. G., Ehrhardt, M. R., Urbauer, J. L., Wand, A. J., Sedarous, S. S., M, c. D., and Buckley, P. J. 1994. *Nature.* 368: 651–653.
21. Gazit, E., Lee, W. J., Brey, P. T., and Shai, Y. 1994. *Biochemistry.* 33: 10681–10692.
22. Greenfield, N., and Fasman, G. D. 1969. Computed circular dichroism spectra for the evaluation of protein conformation. *Biochemistry.* 8: 4108–4116.
23. Habermann, E., and Jentsch, J. 1967. *Hoppe Seyler's Z. Physiol. Chem.* 348: 37–50.
24. Katchalski, E., and Sela, M. 1958. *Adv. Protein Chem.* 13: 243–492.
25. Kuchinka, E., and Seelig, J. 1989. Interaction of melittin with phosphatidylcholine membranes. Binding isotherm and lipid head-group conformation. *Biochemistry.* 28: 4216–4221.
26. Li, Z. Q., Merrifield, R. B., Boman, I. A., and Boman, H. G. 1988. Effects on electrophoretic mobility and antibacterial spectrum of removal of two residues from synthetic sarcotoxin IA and addition of the same residues to cecropin B. *FEBS Lett.* 231: 299–302.
27. Loew, L. M., Rosenberg, I., Bridge, M., and Gitler, C. 1983. Diffusion potential cascade. Conventional detection of transferable membrane pores. *Biochemistry.* 22: 837–844.
28. Merrifield, R. B., Vizioli, L. D., and Boman, H. G. 1982. Synthesis of the antibacterial peptide cecropin A (1–33). *Biochemistry.* 21: 5020–5031.
29. Mor, A., Nguyen, V. H., Delfour, A., Migliore, S. D., and Nicolas, P. 1991. Isolation, amino acid sequence, and synthesis of dermaseptin, a novel antimicrobial peptide of amphibian skin. *Biochemistry.* 30: 8824–8830.
30. Okada, M., and Natori, S. 1984. Mode of action of a bactericidal protein induced in the haemolymph of *Sarcophaga peregrina* (flesh-fly) larvae. *Biochem. J.* 222: 119–124.
31. Oren, Z., and Shai, Y. 1996. A class of highly potent antibacterial peptides derived from pardaxin, a pore-forming peptide isolated from Moses sole fish *Pardachirus marmoratus*. *Eur. J. Biochem.* 237: 303–310.
32. Papahadjopoulos, D., and Miller, N. 1967. Phospholipid model membranes. Structural characteristics of hydrated liquid crystals. *Biochim. Biophys. Acta.* 135: 624–638.
33. Perez, P. E., Houghten, R. A., and Blondelle, S. E. 1994. Determination of the secondary structure of selected melittin analogues with different haemolytic activities. *Biochem. J.*
34. Pouny, Y., and Shai, Y., 1992. Interaction of D-amino acid incorporated analogues of pardaxin with membranes. *Biochemistry.* 39: 9482–9490.
35. Rapaport, D., and Shai, Y. 1992. Aggregation and organization of pardaxin in phospholipid membranes. A fluorescence energy transfer study. *J. Biol. Chem.* 267–6502–6509.
36. Rapaport, D., and Shai, Y. 1991. Interaction of fluorescently labeled pardaxin and its analogues with lipid bilayers. *J. Biol. Chem.* 266: 23769–23775.
37. Rizzo, V., Stankowski, S., and Schwarz, G. 1987. Alamethicin incorporation in lipid bilayers: a thermodynamic study. *Biochemistry.* 26: 2751–9.
38. Russell, P. E., Milling, R. J., and Wright, K. 1995. Fifty years of antimicrobials: past perspectives and future trends (Hunter P. A., Darby G. K., and Russell N. J. Ed) pp. 67–85, Cambridge University Press, Cambridge
39. Schwarz, G., Gerke, H., Rizzo, V., and Stankowski, S. 1987. Incorporation kinetics in a membrane, studied with the pore-forming peptide alamethicin. *Biophys. J.* 52: 685–692.
40. Segrest, J. P., De, L. H., Dohlman, J. G., Brouillette, C. G., and Anantharamaiah, G. M. 1990. Amphipathic helix motif: classes and properties [published erratum appears in Proteins 1991;9(1):79]. *Proteins.* 8: 103–117.
41. Shai, Y. 1995. Molecular recognition between membrane-spanning helices. *TIBS.* in press.
42. Shai, Y. 1994. Pardaxin: channel formation by a shark repellant peptide from fish. *Toxicology.* 87: 109–129.
43. Shai, Y., Fox, J., Caratsch, C., Shih, Y. L., Edwards, C., and Lazarovici, P. 1988. Sequencing and synthesis of pardaxin, a polypeptide from the Rea Sea Moses sole with ionophore activity. *FEBS Lett.* 242: 161–166.
44. Shai, Y., Fox, J., Caratsch, C., Shih, Y. L., Edwards, C., and Lazarovici, P. 1988. Sequencing and synthesis of pardaxin, a polypeptide from the Rea Sea Moses sole with ionophore activity. *FEBS Lett.* 242: 161–166.
45. Shai, Y., Hadari, Y. R., and Finkels, A. 1991. pH-dependent pore formation properties of pardaxin analogues. *J. Biol. Chem.* 266: 22346–22354.
46. Shaw, N. 1974. Lipid composition as a guide to the classification of bacteria. *Adv. Appl. Microbiol.* 17: 63–108.
47. Sims, P. J., Waggoner, A. S., Wang, C. H., and Hoffmann, J. R. 1974. Studies on the mechanism by cyanine dyes measure membrane potential in red blood cells and phosphatidylcholine vesicles. *Biochemistry.* 13: 3315–3330.
48. Steiner, H., Hultmark, D., Engstrom, A., Bennich, H., and Boman, H. G. 1981. Sequence and specificity of two antibacterial proteins involved in insect immunity. *Nature.* 292: 246–248.
49. Terwilliger, T. C., and Eisenberg, D. 1982. The structure of melittin. I. Structure determination and partial refinement. *J. Biol. Chem.* 257: 6010–6015.
50. Terwilliger, T. C., and Eisenberg, D. 1982. The structure of melittin. II. Interpretation of the structure. *J. Biol. Chem.* 257: 6016–6022.
51. Thompson, S. A., Tachibana, K., Nakanishi, K., and Kubota, I. 1986. Melittin-Like Peptides from the Shark-Repelling Defense Secretion of the Sole *Pardachirus pavoninus.* *Science.* 233: 341–343.
52. Verkleij, A. J., Zwaal, R. F., Roelofsen, B., Comfurius, P., Kastelijn, D., and Deenen, L. v. 1973. The asymmetric distribution of phospholipids in the human red cell membrane. A combined study using phospholipases and freeze-etch electron microscopy. *Biochim. Biophys. Acta.* 323: 178–193.
53. Wade, D., Boman, A., Wahlin, B., Drain, C. M., Andreu, D., Boman, H. G., and Merrifield, R. B. 1990. *Proc. Natl. Acad. Sci. USA.* 87: 4761–4765.
54. Wu, C. S., Ikeda, K., and Yang, J. T. 1981. Ordered conformation of polypeptides and proteins in acidic dodecyl sulfate solution. *Biochemistry.* 20: 566–570.
55. Zagorski, M. G., Norman, D. G., Barrow, C. J., Iwashita, T., Tachibana, K., and Patel, D. J. 1991. Solution structure of pardaxin P-2. *Biochemistry.* 30: 8009–8017.

The invention claimed is:

1. A peptide selected from the group consisting of:

(A) a non-natural synthetic peptide having from 6 to 12 amino acid residues or a non-natural synthetic cyclic peptide having from 6 to 14 amino acid residues and a net positive charge which is greater than +1, said peptide consisting of hydrophobic amino acid residues excepting glycine and tyrosine, and positively charged amino acid residues, wherein at least one but not all of such amino acid residues is a D-amino acid, said peptide having a ratio of hydrophobic to positively charged amino acids such that the peptide is cytolytic to pathogenic cells but does not cause cytolysis of red blood cells, and having a sequence of amino acids such that the same amino acid sequence in which each residue is in the L-configuration is not found in nature, and cyclic derivatives thereof having from 6 to 14 amino acid residues, with the proviso that said peptide is not that of SEQ ID NO:1, SEQ ID NO:12, SEQ ID NO:14, or SEQ ID NO:23;

(B) a non-natural synthetic peptide having from 6 to 12 amino acid residues or a non-natural synthetic cyclic peptide having from 6 to 14 amino acid residues and a net positive charge which is greater than +1, said peptide consisting of hydrophobic amino acid residues excepting glycine and tyrosine, positively charged amino acid residues, and polar amino acid residues, wherein at least one but not all of such amino acid residues is a D-amino acid, said peptide having a ratio of hydrophobic to positively charged amino acids such that the peptide is cytolytic to pathogenic cells but does not cause cytolysis of red blood cells, and having a sequence of amino acids such that the same amino acid sequence in which each residue is in the L-configuration is not found in nature, and cyclic derivatives thereof having from 6 to 14 amino acid residues, with the proviso that said peptide is not that of SEQ ID NO:1, SEQ ID NO:12, SEQ ID NO:14, or SEQ ID NO:23;

(C) a random copolymer having a net positive charge which is greater than +1, said random copolymer consisting of a hydrophobic L-amino acid, a positively charged L-amino acid and a D-amino acid in a ratio of hydrophobic to positively charged amino acids such that the copolymer is cytolytic to pathogenic cells but does not cause cytolysis of red blood cells; and (D) a mixture of a plurality of peptide diastereomers, each peptide having at least 6 amino acids and having a net positive charge which is greater than +1, said peptide comprising a hydrophobic L-amino acid, a positively charged L-amino acid and a D-amino acid, said mixture being obtained by solid phase synthesis wherein at each coupling step a mixture composed of 1 eq of each of the amino acids is added to the reaction, followed by HF cleavage.

2. A peptide according to claim 1 consisting of a non-natural synthetic peptide having from 6 to 12 amino acid residues or a non-natural synthetic cyclic peptide having from 6 to 14 amino acid residues and a net positive charge which is greater than +1, said peptide consisting of hydrophobic amino acid residues excepting glycine and tyrosine, and positively charged amino acid residues wherein at least one but not all of such amino acid residues is a D-amino acid, said peptide having a ratio of hydrophobic to positively charged amino acids such that the peptide is cytolytic to pathogenic cells but does not cause cytolysis of red blood cells, and having a sequence of amino acids such that the same amino acid sequence in which each residue is in the L-configuration is not found in nature, and cyclic derivatives thereof having from 6 to 14 amino acid residues, with the proviso that said peptide is not that of SEQ ID NO:1, SEQ ID NO:12, SEQ ID NO:14, or SEQ ID NO:23.

3. The peptide according to claim 2, wherein the positively charged amino acid residues are selected from the group consisting of lysine, arginine and histidine, and the hydrophobic amino acid residues are selected from the group consisting of leucine, isoleucine, alanine, valine, phenylalanine, proline, and tryptophan.

4. The peptide according to claim 3, in which each of the hydrophobic amino acid residues is leucine or valine, and each of the positively charged amino acid residues is lysine.

5. The peptide according to claim 4, being a diastereomer of a 12-mer peptide in which the hydrophobic amino acid is valine and the positively charged amino acid is lysine, in which at least one third of the sequence is composed of D-amino acids, or a cyclic derivative thereof.

6. The peptide according to claim 5 consisting of a Val/Lys diastereomer selected from the group of peptides consisting of the amino acid sequences of SEQ ID NO:34, SEQ ID NO:35, SEQ ID NO:36, and SEQ ID NO:37.

7. The peptide according to claim 4, being a diastereomer of a 6-mer, 8-mer or 12-mer peptide in which the hydrophobic amino acid is leucine and the positively charged amino acid is lysine, in which at least one third of the sequence, but not the full sequence, is composed of D-amino acids, or a cyclic derivative thereof, but expecting the peptide herein designated 23: Lys-Leu-Leu-Leu-Lys-Leu-Leu-Leu-Leu-Lys-Leu-Lys-NH$_2$ (SEQ ID NO:23).

8. The peptide according to claim 7 consisting of a Leu/Lys diastereomer selected from the group of peptides consisting of those herein designated 24 to 29 (SEQ ID NO:24–29), of the sequences:
- 24) Lys-Leu-Leu-Leu-Lys-Leu-Lys-Leu-Lys-Leu-Leu-Lys-NH$_2$,
- 25) Lys-Lys-Leu-Leu-Lys-Leu-Lys-Leu-Lys-Leu-Lys-Lys-NH$_2$,
- 26) Lys-Leu-Leu-Leu-Lys-Leu-Leu-Leu-Lys-Leu-Leu-Lys-NH$_2$,
- 27) Lys-Leu-Leu-Leu-Lys-Leu-Lys-Leu-Lys-Leu-Leu-Lys-NH$_2$,
- 28) Lys-Leu-Leu-Leu-Leu-Lys, and
- 29) Lys-Leu-Leu-Leu-Lys-Leu-Leu-Lys.

9. The peptide according to claim 7 selected from the group consisting of a 6-mer diastereomer in which the ratio of leucine to lysine is 64%:36% and a 12-mer diastereomer in which the ratio of leucine to lysine is 66%:34%.

10. The peptide according to claim 7 consisting of a cyclic diastereomer selected from the group of peptides consisting of those herein designated 94 and 95 (SEQ ID NO:94–95, respectively), of the sequences:
- 94) HN-Lys Leu Leu Leu Lys Leu Leu Leu Lys Leu Leu Lys-CO, and
- 95) HN-Lys Leu LeuLeu Lys Leu Lys Leu Lys Leu Leu Lys-CO.

11. The peptide according to claim 2, wherein the net positive charge greater than +1 is due to the amino acid composition or to the addition of positively charged chemical groups, or which hydrophobicity is decreased by the addition of polar amino acids selected from the group consisting of serine, threonine, methionine, asparagine, glutamine and cysteine.

12. A peptide according to claim 1 consisting of a non-natural synthetic peptide having from 6 to 12 amino acid residues or a non-natural synthetic cyclic peptide having from 6 to 14 amino acid residues and a net positive charge which is greater than +1, said peptide comprising solely hydrophobic amino acid residues excepting glycine and tyrosine, and positively charged and polar amino acid residues, wherein at least one but not all of such amino acid residues is a D-amino acid, said peptide having a ratio of hydrophobic to positively charged amino acids such that the peptide is cytolytic to pathogenic cells but does not cause cytolysis or red blood cells, and having a sequence of amino acids such that the same amino acid sequence in which each residue is in the L-configuration is not found in nature, and cyclic derivatives thereof from 6 to 14 amino acid residues, with the proviso that said peptide is not that of SEQ ID NO:1, SEQ ID NO:12, SEQ ID NO:14, or SEQ ID NO:23.

13. The peptide according to claim 12 wherein the positively charged amino acid is selected from the group consisting of lysine, arginine and histidine, the hydrophobic amino acid is selected from the group consisting of leucine, isoleucine, alanine, valine, phenylalanine, proline, and tryptophan, and the polar amino acid is selected from the group consisting of serine, threonine, methionine, asparagine, glutamine and cysteine.

14. The peptide according to claim 13 consisting of a cyclic peptide in which the hydrophobic amino acid is leucine, the positively charged amino acid is lysine, and the polar amino acid is cysteine; and said cyclic peptide is selected from the group of peptides consisting of those herein designated 92–93 (SEQ ID NOS:92–93, respectively), of the sequence:
- 92) Cyclic Cys Lys Leu LeuLeu Lys Leu Leu Leu Lys Leu Leu Lys Cys,
- 93) Cyclic Cys Lys Leu LeuLeu Lys Leu Lys Leu Lys Leu Lys Cys.

15. A peptide according to claim 1 being a mixture of a plurality of peptide diastereomers, each peptide having at least 6 amino acids and having a net positive charge which is greater than +1, said peptide comprising a hydrophobic L-amino acid, a positively charged L-amino acid and a D-amino acid, said mixture being obtained by solid phase synthesis wherein at each coupling step a mixture composed of 1 eq of each of the amino acids is added to the reaction, followed by HF cleavage.

16. A peptide mixture according to claim 15 wherein the amino acids are L-lysine, L-leucine and D-leucine and the resulting mixture contains $3^{12}$ different 12-mer peptide diastereomers composed of L-Lys, L-Leu and D-Leu.

17. A peptide according to claim 1 being a random copolymer having a net positive charge which is greater than 30 1, said random copolymer consisting of a hydrophobic L-amino acid, a positively charged L-amino acid and a D-amino acid in a ratio of hydrophobic to positively charged amino acids such that the copolymer is cytolytic to pathogenic cells but does not cause cytolysis of red blood cells.

18. The random copolymer according to claim 17, consisting of L-lysine, L-leucine and D-leucine in the molar ratio 1:1:1, 2:1:1 or 3:1:1.

* * * * *